(12) United States Patent
Mauch et al.

(10) Patent No.: US 10,646,338 B2
(45) Date of Patent: May 12, 2020

(54) DELIVERY SYSTEMS WITH TELESCOPING CAPSULES FOR DEPLOYING PROSTHETIC HEART VALVE DEVICES AND ASSOCIATED METHODS

(71) Applicant: Twelve, Inc., Redwood City, CA (US)

(72) Inventors: Kevin Mauch, Windsor, CA (US); Joshua Dwork, Santa Rosa, CA (US)

(73) Assignee: Twelve, Inc., Redwood City, CA (US)

( * ) Notice: Subject to any disclaimer, the term of this patent is extended or adjusted under 35 U.S.C. 154(b) by 26 days.

(21) Appl. No.: 15/611,823

(22) Filed: Jun. 2, 2017

(65) Prior Publication Data

US 2018/0344454 A1 Dec. 6, 2018

(51) Int. Cl.
*A61F 2/24* (2006.01)
*A61F 2/844* (2013.01)

(52) U.S. Cl.
CPC ............ *A61F 2/243* (2013.01); *A61F 2/2436* (2013.01); *A61F 2/844* (2013.01); *A61F 2/2427* (2013.01)

(58) Field of Classification Search
CPC ...... A61F 2/243; A61F 2/2436; A61F 2/2439; A61F 2/2433; A61F 2/2427; A61F 2/844; A61F 2/95; A61F 2002/9665; A61F 2002/9534; A61F 2002/9528; A61F 2/962; A61F 2002/9522; A61F 2/966
See application file for complete search history.

(56) References Cited

U.S. PATENT DOCUMENTS

| | | |
|---|---|---|
| 3,526,219 A | 9/1970 | Balamuth |
| 3,565,062 A | 2/1971 | Kuris |
| 3,589,363 A | 6/1971 | Banko et al. |
| 3,667,474 A | 6/1972 | Lapkin et al. |
| 3,823,717 A | 7/1974 | Pohlman et al. |
| 3,861,391 A | 1/1975 | Antonevich et al. |

(Continued)

FOREIGN PATENT DOCUMENTS

| | | |
|---|---|---|
| CN | 1440261 A | 9/2003 |
| CN | 101076290 A | 11/2007 |

(Continued)

OTHER PUBLICATIONS

US 9,265,606 B2, 02/2016, Buchbinder et al. (withdrawn)

(Continued)

*Primary Examiner* — Katrina M Stransky

(74) *Attorney, Agent, or Firm* — Shumaker & Sieffert, P.A.

(57) ABSTRACT

Delivery systems with telescoping capsules for delivering prosthetic heart valve devices and associated methods are disclosed herein. A delivery system configured in accordance with embodiments of the present technology can include, for example, a delivery capsule having a first housing, a second housing slidably disposed within a portion of the first housing, and a prosthetic device constrained within the first and second housings. The delivery capsule can further include first and second chamber defined in part by the first and second housings. During deployment, fluid is delivered to the first chamber to move the first housing distally over the second housing, thereby releasing a portion of the prosthetic device. Subsequently, fluid is delivered to the second chamber such that the first and second housings move together in the distal direction to release a second portion of the prosthetic device.

22 Claims, 22 Drawing Sheets

(56) References Cited

U.S. PATENT DOCUMENTS

| | | |
|---|---|---|
| 3,896,811 A | 7/1975 | Storz |
| 4,042,979 A | 8/1977 | Angell |
| 4,188,952 A | 2/1980 | Loschilov et al. |
| 4,282,882 A | 8/1981 | Langham |
| 4,431,006 A | 2/1984 | Trimmer et al. |
| 4,445,509 A | 5/1984 | Auth |
| 4,484,579 A | 11/1984 | Meno et al. |
| 4,490,859 A | 1/1985 | Black et al. |
| 4,587,958 A | 5/1986 | Noguchi et al. |
| 4,589,419 A | 5/1986 | Laughlin et al. |
| 4,602,911 A | 7/1986 | Ahmadi et al. |
| 4,646,736 A | 3/1987 | Auth |
| 4,649,922 A | 3/1987 | Wiktor |
| 4,692,139 A | 9/1987 | Stiles |
| 4,747,821 A | 5/1988 | Kensey et al. |
| 4,750,902 A | 6/1988 | Wuchinich et al. |
| 4,777,951 A | 10/1988 | Cribier et al. |
| 4,787,388 A | 11/1988 | Hofmann |
| 4,796,629 A | 1/1989 | Grayzel |
| 4,808,153 A | 2/1989 | Parisi |
| 4,819,751 A | 4/1989 | Shimada et al. |
| 4,841,977 A | 6/1989 | Griffith et al. |
| 4,870,953 A | 10/1989 | DonMicheal et al. |
| 4,878,495 A | 11/1989 | Grayzel |
| 4,898,575 A | 2/1990 | Fischell et al. |
| 4,909,252 A | 3/1990 | Goldberger |
| 4,919,133 A | 4/1990 | Chiang |
| 4,920,954 A | 5/1990 | Alliger et al. |
| 4,936,281 A | 6/1990 | Stasz |
| 4,960,411 A | 10/1990 | Buchbinder |
| 4,986,830 A | 1/1991 | Owens et al. |
| 4,990,134 A | 2/1991 | Auth |
| 5,058,570 A | 10/1991 | Idemoto et al. |
| 5,069,664 A | 12/1991 | Guess et al. |
| 5,076,276 A | 12/1991 | Sakurai et al. |
| 5,106,302 A | 4/1992 | Farzin-Nia et al. |
| 5,248,296 A | 9/1993 | Alliger |
| 5,267,954 A | 12/1993 | Nita |
| 5,269,291 A | 12/1993 | Carter |
| 5,295,958 A | 3/1994 | Shturman |
| 5,304,115 A | 4/1994 | Pflueger et al. |
| 5,314,407 A | 5/1994 | Auth et al. |
| 5,318,014 A | 6/1994 | Carter |
| 5,332,402 A | 7/1994 | Teitelbaum |
| 5,344,426 A | 9/1994 | Lau et al. |
| 5,352,199 A | 10/1994 | Tower |
| 5,356,418 A | 10/1994 | Shturman |
| 5,397,293 A | 3/1995 | Alliger et al. |
| 5,411,025 A | 5/1995 | Webster, Jr. |
| 5,411,552 A | 5/1995 | Andersen et al. |
| 5,443,446 A | 8/1995 | Shturman |
| 5,449,373 A | 9/1995 | Pinchasik et al. |
| 5,489,297 A | 2/1996 | Duran |
| 5,584,879 A | 12/1996 | Reimold et al. |
| 5,609,151 A | 3/1997 | Mulier et al. |
| 5,626,603 A | 5/1997 | Venturelli et al. |
| 5,656,036 A | 8/1997 | Palmaz |
| 5,662,671 A | 9/1997 | Barbut et al. |
| 5,681,336 A | 10/1997 | Clement et al. |
| 5,695,507 A | 12/1997 | Auth et al. |
| 5,725,494 A | 3/1998 | Brisken |
| 5,782,931 A | 7/1998 | Yang et al. |
| 5,817,101 A * | 10/1998 | Fiedler ............... A61F 2/95 623/1.11 |
| 5,827,229 A | 10/1998 | Auth et al. |
| 5,827,321 A | 10/1998 | Roubin et al. |
| 5,840,081 A | 11/1998 | Andersen et al. |
| 5,853,422 A | 12/1998 | Huebsch et al. |
| 5,855,601 A | 1/1999 | Bessler et al. |
| 5,868,781 A | 2/1999 | Killion |
| 5,873,811 A | 2/1999 | Wang et al. |
| 5,904,679 A | 5/1999 | Clayman |
| 5,910,129 A | 6/1999 | Koblish et al. |
| 5,957,882 A | 9/1999 | Nita et al. |
| 5,972,004 A | 10/1999 | Williamson, IV et al. |
| 5,989,208 A | 11/1999 | Nita |
| 5,989,280 A * | 11/1999 | Euteneuer ............... A61F 2/95 623/1.1 |
| 6,047,700 A | 4/2000 | Eggers et al. |
| 6,056,759 A | 5/2000 | Fiedler |
| 6,085,754 A | 7/2000 | Alferness et al. |
| 6,113,608 A | 9/2000 | Monroe et al. |
| RE36,939 E | 10/2000 | Tachibana et al. |
| 6,129,734 A | 10/2000 | Shturman et al. |
| 6,132,444 A | 10/2000 | Shturman et al. |
| 6,159,139 A | 12/2000 | Chiu |
| 6,168,579 B1 | 1/2001 | Tsugita |
| 6,217,595 B1 | 4/2001 | Shturman et al. |
| 6,254,635 B1 | 7/2001 | Schroeder et al. |
| 6,295,712 B1 | 10/2001 | Shturman et al. |
| 6,306,414 B1 | 10/2001 | Koike |
| 6,321,109 B2 | 11/2001 | Ben-Haim et al. |
| 6,402,679 B1 | 6/2002 | Mortier et al. |
| 6,423,032 B2 | 7/2002 | Parodi |
| 6,425,916 B1 | 7/2002 | Garrison et al. |
| 6,440,164 B1 | 8/2002 | DiMatteo et al. |
| 6,454,737 B1 | 9/2002 | Nita et al. |
| 6,454,757 B1 | 9/2002 | Nita et al. |
| 6,454,799 B1 | 9/2002 | Schreck |
| 6,458,153 B1 | 10/2002 | Bailey et al. |
| 6,461,382 B1 | 10/2002 | Cao |
| 6,494,890 B1 | 12/2002 | Shturman et al. |
| 6,494,891 B1 | 12/2002 | Cornish et al. |
| 6,505,080 B1 | 1/2003 | Sutton |
| 6,514,261 B1 | 2/2003 | Randall et al. |
| 6,530,952 B2 | 3/2003 | Vesely |
| 6,540,782 B1 | 4/2003 | Snyders |
| 6,562,067 B2 | 5/2003 | Mathis |
| 6,565,588 B1 | 5/2003 | Clement et al. |
| 6,569,196 B1 | 5/2003 | Vesely |
| 6,579,308 B1 | 6/2003 | Jansen et al. |
| 6,582,460 B1 | 6/2003 | Cryer |
| 6,582,462 B1 | 6/2003 | Andersen et al. |
| 6,595,912 B2 | 7/2003 | Lau et al. |
| 6,605,109 B2 | 8/2003 | Fiedler |
| 6,616,689 B1 | 9/2003 | Ainsworth et al. |
| 6,623,452 B2 | 9/2003 | Chien et al. |
| 6,638,288 B1 | 10/2003 | Shturman et al. |
| 6,648,854 B1 | 11/2003 | Patterson et al. |
| 6,689,086 B1 | 2/2004 | Nita et al. |
| 6,702,748 B1 | 3/2004 | Nita et al. |
| 6,730,121 B2 | 5/2004 | Ortiz et al. |
| 6,746,463 B1 | 6/2004 | Schwartz |
| 6,811,801 B1 | 11/2004 | Nguyen et al. |
| 6,818,001 B2 | 11/2004 | Wulfman et al. |
| 6,843,797 B2 | 1/2005 | Nash et al. |
| 6,852,118 B2 | 2/2005 | Shturman et al. |
| 6,855,123 B2 | 2/2005 | Nita |
| 6,869,439 B2 | 3/2005 | White et al. |
| 6,951,571 B1 | 10/2005 | Srivastava |
| 6,986,775 B2 | 1/2006 | Morales et al. |
| 7,018,404 B2 | 3/2006 | Holmberg et al. |
| 7,052,487 B2 | 5/2006 | Cohn et al. |
| 7,077,861 B2 | 7/2006 | Spence |
| 7,125,420 B2 | 10/2006 | Rourke et al. |
| 7,163,552 B2 | 1/2007 | Diaz |
| 7,186,264 B2 | 3/2007 | Liddicoat et al. |
| 7,261,732 B2 | 8/2007 | Justino |
| 7,296,577 B2 | 11/2007 | Lashinski et al. |
| 7,381,218 B2 | 6/2008 | Schreck |
| 7,404,824 B1 | 7/2008 | Webler et al. |
| 7,442,204 B2 | 10/2008 | Schwammenthal et al. |
| 7,473,275 B2 | 1/2009 | Marquez |
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |
| 7,803,168 B2 | 9/2010 | Gifford et al. |
| 7,857,845 B2 | 12/2010 | Stacchino et al. |
| 7,896,915 B2 | 3/2011 | Guyenot et al. |

(56) References Cited

U.S. PATENT DOCUMENTS

| | | |
|---|---|---|
| 7,942,928 B2 | 5/2011 | Webler et al. |
| 7,985,238 B2 | 7/2011 | Balgobin et al. |
| 8,002,826 B2 | 8/2011 | Seguin |
| 8,052,750 B2 | 11/2011 | Tuval et al. |
| 8,062,355 B2 | 11/2011 | Figulla et al. |
| 8,109,996 B2 | 2/2012 | Stacchino et al. |
| 8,114,154 B2 * | 2/2012 | Righini ............... A61F 2/2436 623/1.11 |
| 8,252,051 B2 | 8/2012 | Chau et al. |
| 8,398,704 B2 | 3/2013 | Straubinger et al. |
| 8,403,981 B2 | 3/2013 | Forster et al. |
| 8,403,983 B2 | 3/2013 | Quadri et al. |
| 8,414,643 B2 | 4/2013 | Tuval et al. |
| 8,449,599 B2 | 5/2013 | Chau et al. |
| 8,496,671 B1 | 7/2013 | Hausen |
| 8,512,252 B2 | 8/2013 | Ludomirsky et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,540,767 B2 | 9/2013 | Zhang |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Spenser et al. |
| 8,634,935 B2 | 1/2014 | Gaudiani |
| 8,647,254 B2 | 2/2014 | Callas et al. |
| 8,652,203 B2 | 2/2014 | Quadri et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,685,086 B2 | 4/2014 | Navia et al. |
| 8,688,234 B2 | 4/2014 | Zhu et al. |
| 8,690,858 B2 | 4/2014 | Machold et al. |
| 8,709,074 B2 | 4/2014 | Solem et al. |
| 8,712,133 B2 | 4/2014 | Guhring et al. |
| 8,715,160 B2 | 5/2014 | Raman et al. |
| 8,721,665 B2 | 5/2014 | Oz et al. |
| 8,721,718 B2 | 5/2014 | Kassab |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Randert et al. |
| 8,792,699 B2 | 7/2014 | Guetter et al. |
| 8,795,356 B2 | 8/2014 | Quadri et al. |
| 8,801,779 B2 | 8/2014 | Seguin et al. |
| 8,808,356 B2 | 8/2014 | Braido et al. |
| 8,808,366 B2 | 8/2014 | Braido et al. |
| 8,812,431 B2 | 8/2014 | Voigt et al. |
| 8,828,043 B2 | 9/2014 | Chambers |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,894,702 B2 | 11/2014 | Quadri et al. |
| 8,900,214 B2 | 12/2014 | Nance et al. |
| 8,900,295 B2 | 12/2014 | Migliazza et al. |
| 8,926,694 B2 | 1/2015 | Costello |
| 8,932,348 B2 | 1/2015 | Solem et al. |
| 8,951,285 B2 | 2/2015 | Sugimoto et al. |
| 8,961,597 B2 | 2/2015 | Subramanian et al. |
| 8,968,393 B2 | 3/2015 | Rothstein |
| 8,968,395 B2 | 3/2015 | Hauser et al. |
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,023,101 B2 | 5/2015 | Krahbichler |
| 9,050,188 B2 | 6/2015 | Schweich, Jr. et al. |
| 9,066,800 B2 | 6/2015 | Clague et al. |
| 9,084,676 B2 | 7/2015 | Chau et al. |
| 9,095,433 B2 | 8/2015 | Lutter et al. |
| 9,119,713 B2 | 9/2015 | Board et al. |
| 9,132,009 B2 | 9/2015 | Hacohen et al. |
| 9,138,312 B2 | 9/2015 | Tuval et al. |
| 9,138,313 B2 | 9/2015 | McGuckin, Jr. et al. |
| 9,180,005 B1 | 11/2015 | Lashinski et al. |
| 9,192,466 B2 | 11/2015 | Kovalsky et al. |
| 9,192,471 B2 | 11/2015 | Bolling |
| 9,226,825 B2 | 1/2016 | Starksen et al. |
| 9,232,942 B2 | 1/2016 | Seguin et al. |
| 9,232,998 B2 | 1/2016 | Wilson et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,254,192 B2 | 2/2016 | Lutter et al. |
| 9,259,317 B2 | 2/2016 | Wilson et al. |
| 9,271,833 B2 | 3/2016 | Kim et al. |
| 9,289,291 B2 | 3/2016 | Gorman, III et al. |
| 9,289,297 B2 | 3/2016 | Wilson et al. |
| 9,289,927 B2 | 3/2016 | Weber et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,326,852 B2 | 5/2016 | Spenser |
| 9,333,073 B2 | 5/2016 | Quadri et al. |
| 9,333,074 B2 | 5/2016 | Quadri et al. |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,108 B2 | 6/2016 | Bortlein et al. |
| 9,387,075 B2 | 7/2016 | Bortlein et al. |
| 9,387,078 B2 | 7/2016 | Gross et al. |
| 9,393,111 B2 | 7/2016 | Ma et al. |
| 9,425,916 B2 | 8/2016 | Nakao et al. |
| 9,579,198 B2 | 2/2017 | Deem et al. |
| 9,629,719 B2 | 4/2017 | Rothstein et al. |
| 9,675,454 B2 | 6/2017 | Vidlund et al. |
| 9,681,951 B2 | 6/2017 | Ratz et al. |
| 9,687,342 B2 | 6/2017 | Figulla et al. |
| 9,687,343 B2 | 6/2017 | Bortlein et al. |
| 9,693,859 B2 | 7/2017 | Braido et al. |
| 9,693,862 B2 | 7/2017 | Campbell et al. |
| 9,694,121 B2 | 7/2017 | Alexander et al. |
| 9,700,409 B2 | 7/2017 | Braido et al. |
| 9,700,411 B2 | 7/2017 | Klima et al. |
| 9,730,791 B2 | 8/2017 | Ratz et al. |
| 9,730,794 B2 | 8/2017 | Carpentier et al. |
| 9,750,605 B2 | 9/2017 | Ganesan et al. |
| 9,750,606 B2 | 9/2017 | Ganesan et al. |
| 9,750,607 B2 | 9/2017 | Ganesan et al. |
| 9,763,657 B2 | 9/2017 | Hacohen et al. |

(56) References Cited

U.S. PATENT DOCUMENTS

| | | |
|---|---|---|
| 9,763,658 B2 | 9/2017 | Eigler et al. |
| 9,763,782 B2 | 9/2017 | Solem et al. |
| 9,770,328 B2 | 9/2017 | Macoviak |
| 9,788,931 B2 | 10/2017 | Giordano et al. |
| 9,801,717 B2 | 10/2017 | Edquist et al. |
| 9,827,092 B2 | 11/2017 | Vidlund et al. |
| 9,827,101 B2 | 11/2017 | Solem et al. |
| 9,833,313 B2 | 12/2017 | Board et al. |
| 9,833,315 B2 | 12/2017 | Vidlund et al. |
| 9,839,511 B2 | 12/2017 | Ma et al. |
| 9,844,435 B2 | 12/2017 | Eidenschink |
| 9,848,880 B2 | 12/2017 | Coleman et al. |
| 9,848,983 B2 | 12/2017 | Lashinski et al. |
| 9,861,477 B2 | 1/2018 | Backus et al. |
| 9,861,480 B2 | 1/2018 | Zakai et al. |
| 9,968,453 B2 | 5/2018 | Vola et al. |
| 10,258,468 B2 | 4/2019 | Deem et al. |
| 2001/0021872 A1 | 9/2001 | Bailey et al. |
| 2001/0049492 A1 | 12/2001 | Frazier et al. |
| 2002/0007219 A1 | 1/2002 | Merrill et al. |
| 2002/0013571 A1 | 1/2002 | Goldfarb et al. |
| 2002/0072792 A1 | 6/2002 | Burgermeister et al. |
| 2002/0077627 A1 | 6/2002 | Johnson et al. |
| 2002/0082637 A1 | 6/2002 | Lumauig |
| 2002/0099439 A1 | 7/2002 | Schwartz et al. |
| 2002/0138138 A1 | 9/2002 | Yang |
| 2002/0151970 A1 | 10/2002 | Garrison et al. |
| 2002/0173841 A1 | 11/2002 | Ortiz et al. |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0106989 A1 | 6/2004 | Wilson et al. |
| 2004/0117009 A1 | 6/2004 | Cali et al. |
| 2004/0122510 A1 | 6/2004 | Sarac |
| 2004/0127979 A1 | 7/2004 | Wilson et al. |
| 2004/0127982 A1 | 7/2004 | Machold et al. |
| 2004/0186558 A1 | 9/2004 | Pavcnik et al. |
| 2004/0199191 A1 | 10/2004 | Schwartz |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243162 A1 | 12/2004 | Wulfman et al. |
| 2005/0007219 A1 | 1/2005 | Ma et al. |
| 2005/0075662 A1 | 4/2005 | Pedersen et al. |
| 2005/0075720 A1 | 4/2005 | Nguyen et al. |
| 2005/0075727 A1 | 4/2005 | Wheatley |
| 2005/0096647 A1 | 5/2005 | Steinke et al. |
| 2005/0107661 A1 | 5/2005 | Lau et al. |
| 2005/0137682 A1 | 6/2005 | Justino |
| 2005/0137690 A1 | 6/2005 | Salahieh et al. |
| 2005/0137691 A1* | 6/2005 | Salahieh ............... A61F 2/2418 623/2.11 |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0267523 A1 | 12/2005 | Devellian et al. |
| 2006/0058872 A1 | 3/2006 | Salahieh et al. |
| 2006/0106456 A9 | 5/2006 | Machold et al. |
| 2006/0142833 A1 | 6/2006 | Von Oepen et al. |
| 2006/0149360 A1 | 7/2006 | Schwammenthal et al. |
| 2006/0167543 A1 | 7/2006 | Bailey et al. |
| 2006/0195183 A1 | 8/2006 | Navia et al. |
| 2006/0253191 A1 | 11/2006 | Salahieh et al. |
| 2006/0287719 A1 | 12/2006 | Rowe et al. |
| 2007/0056346 A1 | 3/2007 | Spenser et al. |
| 2007/0061010 A1 | 3/2007 | Hauser et al. |
| 2007/0073391 A1 | 3/2007 | Bourang et al. |
| 2007/0088431 A1 | 4/2007 | Bourang et al. |
| 2007/0142906 A1 | 6/2007 | Figulla et al. |
| 2007/0173932 A1 | 7/2007 | Cali et al. |
| 2007/0203561 A1 | 8/2007 | Forster et al. |
| 2008/0071369 A1 | 3/2008 | Tuval et al. |
| 2008/0082166 A1 | 4/2008 | Styrc et al. |
| 2008/0103586 A1 | 5/2008 | Styrc et al. |
| 2008/0140189 A1 | 6/2008 | Nguyen et al. |
| 2008/0208332 A1 | 8/2008 | Lamphere et al. |
| 2008/0221672 A1 | 9/2008 | Lamphere et al. |
| 2008/0234728 A1 | 9/2008 | Starksen et al. |
| 2008/0243245 A1 | 10/2008 | Thambar et al. |
| 2008/0243246 A1 | 10/2008 | Ryan et al. |
| 2009/0024137 A1 | 1/2009 | Chuter et al. |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0157174 A1 | 6/2009 | Yoganathan et al. |
| 2009/0164006 A1 | 6/2009 | Seguin et al. |
| 2009/0198315 A1 | 8/2009 | Boudjemline |
| 2009/0216312 A1 | 8/2009 | Straubinger et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0281618 A1 | 11/2009 | Hill et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023117 A1 | 1/2010 | Yoganathan et al. |
| 2010/0030330 A1 | 2/2010 | Bobo et al. |
| 2010/0035703 A1 | 2/2010 | Ishikawa et al. |
| 2010/0049313 A1 | 2/2010 | Alon et al. |
| 2010/0076548 A1 | 3/2010 | Konno |
| 2010/0082094 A1 | 4/2010 | Quadri et al. |
| 2010/0094411 A1 | 4/2010 | Tuval et al. |
| 2010/0121436 A1 | 5/2010 | Tuval et al. |
| 2010/0160931 A1 | 6/2010 | Karpiel et al. |
| 2010/0185275 A1 | 7/2010 | Richter et al. |
| 2010/0217382 A1 | 8/2010 | Chau et al. |
| 2010/0249915 A1 | 9/2010 | Zhang |
| 2010/0249923 A1 | 9/2010 | Alkhatib et al. |
| 2010/0286768 A1* | 11/2010 | Alkhatib ............... A61F 2/2418 623/2.11 |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1 | 1/2011 | Lutter et al. |
| 2011/0015722 A1 | 1/2011 | Hauser et al. |
| 2011/0022166 A1 | 1/2011 | Dahlgren et al. |
| 2011/0029071 A1 | 2/2011 | Zlotnick et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0153008 A1 | 6/2011 | Marchand et al. |
| 2011/0172784 A1 | 7/2011 | Richter et al. |
| 2011/0184512 A1 | 7/2011 | Webler et al. |
| 2011/0201874 A1 | 8/2011 | Birk et al. |
| 2011/0208293 A1 | 8/2011 | Tabor |
| 2011/0224785 A1 | 9/2011 | Hacohen |
| 2011/0319988 A1 | 12/2011 | Schankereli et al. |
| 2012/0022639 A1 | 1/2012 | Hacohen et al. |
| 2012/0035703 A1 | 2/2012 | Lutter et al. |
| 2012/0035713 A1 | 2/2012 | Lutter et al. |
| 2012/0053680 A1 | 3/2012 | Bolling et al. |

(56) References Cited

U.S. PATENT DOCUMENTS

| | | |
|---|---|---|
| 2012/0053682 A1 | 3/2012 | Kovalsky et al. |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0179239 A1 | 7/2012 | Quadri |
| 2012/0179244 A1 | 7/2012 | Schankereli et al. |
| 2012/0203336 A1 | 8/2012 | Annest |
| 2012/0283824 A1 | 11/2012 | Lutter et al. |
| 2013/0035628 A1 | 2/2013 | Garrison et al. |
| 2013/0138090 A1 | 5/2013 | Fargahi |
| 2013/0172978 A1 | 7/2013 | Vidlund et al. |
| 2013/0190860 A1 | 7/2013 | Sundt, III |
| 2013/0190861 A1 | 7/2013 | Chau et al. |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0204358 A1 | 8/2013 | Matheny |
| 2013/0226289 A1 | 8/2013 | Shaolian et al. |
| 2013/0226290 A1 | 8/2013 | Yellin et al. |
| 2013/0231735 A1* | 9/2013 | Deem .................... A61F 2/243 623/2.11 |
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guhring et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0274870 A1 | 10/2013 | Lombardi et al. |
| 2013/0282059 A1 | 10/2013 | Ketai et al. |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304180 A1 | 11/2013 | Green et al. |
| 2013/0304181 A1* | 11/2013 | Green .................... A61F 2/966 623/1.11 |
| 2013/0304197 A1 | 11/2013 | Buchbinder et al. |
| 2013/0304198 A1 | 11/2013 | Solem |
| 2013/0304200 A1 | 11/2013 | McLean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |
| 2013/0317603 A1 | 11/2013 | McLean et al. |
| 2013/0325110 A1 | 12/2013 | Khalil et al. |
| 2013/0325114 A1 | 12/2013 | McLean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0345797 A1 | 12/2013 | Dahlgren et al. |
| 2013/0345803 A1 | 12/2013 | Bergheim, III |
| 2014/0005778 A1 | 1/2014 | Buchbinder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0121763 A1 | 5/2014 | Duffy et al. |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Jonsson et al. |
| 2014/0172084 A1 | 6/2014 | Callas et al. |
| 2014/0172085 A1 | 6/2014 | Quadri et al. |
| 2014/0172086 A1 | 6/2014 | Quadri et al. |
| 2014/0179993 A1 | 6/2014 | Alexander et al. |
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0194920 A1 | 7/2014 | Krahbichler |
| 2014/0194969 A1 | 7/2014 | Headley |
| 2014/0194976 A1 | 7/2014 | Starksen et al. |
| 2014/0200397 A1 | 7/2014 | Raman et al. |
| 2014/0200649 A1* | 7/2014 | Essinger ............... A61F 2/2436 623/1.12 |
| 2014/0200657 A1 | 7/2014 | Maurer et al. |
| 2014/0200662 A1 | 7/2014 | Eftel et al. |
| 2014/0214159 A1 | 7/2014 | Vidlund et al. |
| 2014/0219524 A1 | 8/2014 | Takeguchi et al. |
| 2014/0222040 A1 | 8/2014 | Park et al. |
| 2014/0222135 A1 | 8/2014 | Forster et al. |
| 2014/0222138 A1 | 8/2014 | Machold et al. |
| 2014/0225946 A1 | 8/2014 | Quinn et al. |
| 2014/0228942 A1 | 8/2014 | Krahbichler |
| 2014/0228946 A1 | 8/2014 | Chau et al. |
| 2014/0242056 A1 | 8/2014 | Karandikar et al. |
| 2014/0242086 A1 | 8/2014 | Lal et al. |
| 2014/0243560 A1 | 8/2014 | Lorenz et al. |
| 2014/0243860 A1 | 8/2014 | Morris et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Magee et al. |
| 2014/0276782 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |
| 2014/0277404 A1 | 9/2014 | Wilson et al. |
| 2014/0277405 A1 | 9/2014 | Wilson et al. |
| 2014/0277406 A1 | 9/2014 | Arcidi |
| 2014/0277407 A1 | 9/2014 | Dale et al. |
| 2014/0277408 A1 | 9/2014 | Folan |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0277412 A1 | 9/2014 | Bortlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0309727 A1 | 10/2014 | Lamelas et al. |
| 2014/0309730 A1 | 10/2014 | Alon et al. |
| 2014/0309731 A1 | 10/2014 | Quadri et al. |
| 2014/0309732 A1 | 10/2014 | Solem |

(56) References Cited

U.S. PATENT DOCUMENTS

| | | |
|---|---|---|
| 2014/0316516 A1 | 10/2014 | Vidlund et al. |
| 2014/0324164 A1 | 10/2014 | Gross et al. |
| 2014/0358222 A1 | 12/2014 | Gorman, III et al. |
| 2014/0358224 A1 | 12/2014 | Tegels et al. |
| 2014/0364944 A1 | 12/2014 | Lutter et al. |
| 2014/0371843 A1 | 12/2014 | Wilson et al. |
| 2014/0371844 A1 | 12/2014 | Dale et al. |
| 2014/0371846 A1 | 12/2014 | Wilson et al. |
| 2014/0379074 A1 | 12/2014 | Spence et al. |
| 2014/0379076 A1 | 12/2014 | Vidlund et al. |
| 2015/0004165 A1 | 1/2015 | Yue et al. |
| 2015/0005874 A1 | 1/2015 | Vidlund et al. |
| 2015/0005875 A1 | 1/2015 | Tuval et al. |
| 2015/0012069 A1 | 1/2015 | Puskas |
| 2015/0018353 A1 | 1/2015 | Kim et al. |
| 2015/0018940 A1 | 1/2015 | Quill et al. |
| 2015/0025311 A1 | 1/2015 | Kadan et al. |
| 2015/0025623 A1 | 1/2015 | Granada et al. |
| 2015/0032127 A1 | 1/2015 | Gammie et al. |
| 2015/0045878 A1 | 2/2015 | Rowe |
| 2015/0057738 A1 | 2/2015 | Hepke et al. |
| 2015/0066138 A1 | 3/2015 | Alexander et al. |
| 2015/0066140 A1 | 3/2015 | Quadri et al. |
| 2015/0094802 A1 | 4/2015 | Buchbinder et al. |
| 2015/0094803 A1 | 4/2015 | Navia |
| 2015/0100116 A1 | 4/2015 | Mohl et al. |
| 2015/0112427 A1 | 4/2015 | Schweich, Jr. et al. |
| 2015/0112429 A1 | 4/2015 | Khairkhahan et al. |
| 2015/0112433 A1 | 4/2015 | Schweich, Jr. et al. |
| 2015/0119978 A1 | 4/2015 | Tegels et al. |
| 2015/0119981 A1 | 4/2015 | Khairkhahan et al. |
| 2015/0119982 A1 | 4/2015 | Quill et al. |
| 2015/0127091 A1 | 5/2015 | Cecere et al. |
| 2015/0127096 A1 | 5/2015 | Rowe et al. |
| 2015/0134055 A1 | 5/2015 | Spence et al. |
| 2015/0139911 A1 | 5/2015 | Santamore et al. |
| 2015/0141855 A1 | 5/2015 | Inoue |
| 2015/0142101 A1 | 5/2015 | Coleman et al. |
| 2015/0142103 A1 | 5/2015 | Vidlund |
| 2015/0142105 A1 | 5/2015 | Bolling et al. |
| 2015/0150678 A1 | 6/2015 | Brecker |
| 2015/0157458 A1 | 6/2015 | Thambar et al. |
| 2015/0157459 A1 | 6/2015 | Macoviak et al. |
| 2015/0164637 A1 | 6/2015 | Khairkhahan et al. |
| 2015/0164639 A1 | 6/2015 | Starksen et al. |
| 2015/0164641 A1 | 6/2015 | Annest |
| 2015/0173897 A1 | 6/2015 | Raanani et al. |
| 2015/0173898 A1 | 6/2015 | Drasler et al. |
| 2015/0173900 A1 | 6/2015 | Hauser et al. |
| 2015/0190229 A1 | 7/2015 | Seguin |
| 2015/0196390 A1 | 7/2015 | Ma et al. |
| 2015/0196393 A1 | 7/2015 | Vidlund et al. |
| 2015/0202043 A1 | 7/2015 | Zakai et al. |
| 2015/0209137 A1 | 7/2015 | Quadri et al. |
| 2015/0209139 A1 | 7/2015 | Granada et al. |
| 2015/0216655 A1 | 8/2015 | Lane et al. |
| 2015/0216661 A1 | 8/2015 | Hacohen et al. |
| 2015/0223802 A1 | 8/2015 | Tegzes |
| 2015/0223934 A1 | 8/2015 | Vidlund et al. |
| 2015/0223935 A1 | 8/2015 | Subramanian et al. |
| 2015/0230920 A1 | 8/2015 | Alfieri et al. |
| 2015/0230921 A1 | 8/2015 | Chau et al. |
| 2015/0238312 A1 | 8/2015 | Lashinski |
| 2015/0238313 A1 | 8/2015 | Spence et al. |
| 2015/0238314 A1 | 8/2015 | Bortlein et al. |
| 2015/0238729 A1 | 8/2015 | Jenson et al. |
| 2015/0250590 A1 | 9/2015 | Gries et al. |
| 2015/0257877 A1 | 9/2015 | Hernandez |
| 2015/0257878 A1 | 9/2015 | Lane et al. |
| 2015/0257879 A1 | 9/2015 | Bortlein et al. |
| 2015/0257881 A1 | 9/2015 | Bortlein et al. |
| 2015/0257882 A1 | 9/2015 | Bortlein et al. |
| 2015/0272734 A1 | 10/2015 | Sheps et al. |
| 2015/0272737 A1 | 10/2015 | Dale et al. |
| 2015/0305861 A1 | 10/2015 | Annest |
| 2015/0305864 A1 | 10/2015 | Quadri et al. |
| 2015/0313739 A1 | 11/2015 | Hummen et al. |
| 2015/0320553 A1 | 11/2015 | Chau et al. |
| 2015/0327999 A1 | 11/2015 | Board et al. |
| 2015/0328000 A1 | 11/2015 | Ratz et al. |
| 2015/0342733 A1 | 12/2015 | Alkhatib et al. |
| 2015/0351906 A1 | 12/2015 | Hammer et al. |
| 2015/0351908 A1 | 12/2015 | Keranen et al. |
| 2015/0359628 A1 | 12/2015 | Keranen |
| 2015/0359629 A1 | 12/2015 | Ganesan et al. |
| 2015/0359631 A1 | 12/2015 | Sheahan et al. |
| 2015/0366666 A1 | 12/2015 | Khairkhahan et al. |
| 2015/0374495 A1 | 12/2015 | Ruyra Baliarda et al. |
| 2016/0000562 A1 | 1/2016 | Siegel |
| 2016/0000564 A1 | 1/2016 | Buchibnder et al. |
| 2016/0000983 A1 | 1/2016 | Mohl et al. |
| 2016/0008129 A1 | 1/2016 | Siegel |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0030171 A1 | 2/2016 | Quijano et al. |
| 2016/0038246 A1 | 2/2016 | Wang et al. |
| 2016/0038280 A1 | 2/2016 | Morriss et al. |
| 2016/0038283 A1 | 2/2016 | Divekar et al. |
| 2016/0038286 A1 | 2/2016 | Yellin et al. |
| 2016/0074160 A1 | 3/2016 | Christianson et al. |
| 2016/0106539 A1 | 4/2016 | Buchbinder et al. |
| 2016/0113764 A1 | 4/2016 | Sheahan et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0151156 A1 | 6/2016 | Seguin et al. |
| 2016/0151552 A1 | 6/2016 | Solem |
| 2016/0157999 A1 | 6/2016 | Lane et al. |
| 2016/0158000 A1 | 6/2016 | Granada et al. |
| 2016/0158001 A1 | 6/2016 | Wallace et al. |
| 2016/0158002 A1 | 6/2016 | Wallace et al. |
| 2016/0158003 A1 | 6/2016 | Wallace et al. |
| 2016/0184095 A1 | 6/2016 | Spence et al. |
| 2016/0206280 A1 | 7/2016 | Vidlund et al. |
| 2016/0206424 A1 | 7/2016 | Al-Jilaihawi et al. |
| 2016/0262881 A1 | 9/2016 | Schankereli et al. |
| 2016/0317290 A1 | 11/2016 | Chau et al. |
| 2017/0079790 A1 | 3/2017 | Vidlund et al. |
| 2017/0100248 A1 | 4/2017 | Tegels et al. |
| 2017/0100250 A1 | 4/2017 | Marsot et al. |
| 2017/0119526 A1 | 5/2017 | Luong et al. |
| 2017/0128198 A1 | 5/2017 | Cartledge et al. |
| 2017/0128205 A1 | 5/2017 | Tamir et al. |
| 2017/0128206 A1 | 5/2017 | Rafiee et al. |
| 2017/0128208 A1 | 5/2017 | Christianson et al. |
| 2017/0156860 A1 | 6/2017 | Lashinski |
| 2017/0165054 A1 | 6/2017 | Benson et al. |
| 2017/0165055 A1 | 6/2017 | Hauser et al. |
| 2017/0165064 A1* | 6/2017 | Nyuli ................ A61F 2/2418 |
| 2017/0172737 A1 | 6/2017 | Kuetting et al. |
| 2017/0181851 A1 | 6/2017 | Annest |
| 2017/0189177 A1 | 7/2017 | Schweich, Jr. et al. |
| 2017/0189179 A1 | 7/2017 | Ratz et al. |
| 2017/0189180 A1 | 7/2017 | Alkhatib |
| 2017/0189181 A1 | 7/2017 | Alkhatib et al. |
| 2017/0196688 A1 | 7/2017 | Christianson et al. |
| 2017/0231762 A1 | 8/2017 | Quadri et al. |
| 2017/0231763 A1 | 8/2017 | Yellin et al. |
| 2017/0258585 A1 | 9/2017 | Marquez et al. |
| 2017/0266001 A1 | 9/2017 | Vidlund et al. |
| 2017/0281345 A1 | 10/2017 | Yang et al. |
| 2017/0290659 A1 | 10/2017 | Ulmer et al. |
| 2017/0296338 A1 | 10/2017 | Cambell et al. |
| 2017/0296339 A1 | 10/2017 | Thambar et al. |
| 2017/0319333 A1 | 11/2017 | Tegels et al. |
| 2017/0325842 A1 | 11/2017 | Siegel |
| 2017/0325941 A1 | 11/2017 | Wallace et al. |
| 2017/0325945 A1 | 11/2017 | Dale et al. |
| 2017/0325948 A1 | 11/2017 | Wallace et al. |
| 2017/0325949 A1 | 11/2017 | Rodgers et al. |

(56) References Cited

U.S. PATENT DOCUMENTS

| | | |
|---|---|---|
| 2017/0325953 A1 | 11/2017 | Klima et al. |
| 2017/0325954 A1 | 11/2017 | Perszyk |
| 2017/0333186 A1 | 11/2017 | Spargias |
| 2017/0333188 A1 | 11/2017 | Carpentier et al. |
| 2017/0340440 A1 | 11/2017 | Ratz et al. |
| 2017/0348097 A1 | 12/2017 | Taft et al. |
| 2017/0348098 A1 | 12/2017 | Rowe et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0354499 A1 | 12/2017 | Granada et al. |
| 2017/0360426 A1 | 12/2017 | Hacohen et al. |
| 2017/0360549 A1 | 12/2017 | Lashinski et al. |
| 2017/0360558 A1 | 12/2017 | Ma |
| 2017/0360585 A1 | 12/2017 | White |
| 2017/0361065 A1 | 12/2017 | Legaspi et al. |

FOREIGN PATENT DOCUMENTS

| | | | |
|---|---|---|---|
| CN | 101291637 A | | 10/2008 |
| CN | 103491900 A | | 1/2014 |
| DE | 19605042 A1 | | 1/1998 |
| DE | 102006052564 B3 | | 12/2007 |
| EP | 186104 A2 | | 7/1986 |
| EP | 1512383 A2 | | 3/2005 |
| EP | 1545371 A2 | | 6/2005 |
| EP | 1551274 A2 | | 7/2005 |
| EP | 1629794 A2 | | 3/2006 |
| EP | 1646332 A2 | | 4/2006 |
| EP | 1702247 A2 | | 9/2006 |
| EP | 1734903 A1 | | 12/2006 |
| EP | 1891914 | | 2/2008 |
| EP | 2026280 A1 | | 2/2009 |
| EP | 2037829 A2 | | 3/2009 |
| EP | 2081519 A2 | | 7/2009 |
| EP | 2111190 A2 | | 10/2009 |
| EP | 2142143 A2 | | 1/2010 |
| EP | 2167742 A1 | | 3/2010 |
| EP | 2278944 A2 | | 2/2011 |
| EP | 2306821 A1 | | 4/2011 |
| EP | 2327429 A1 | | 6/2011 |
| EP | 2400924 | | 1/2012 |
| EP | 2400926 A2 | | 1/2012 |
| EP | 2410947 A1 | | 2/2012 |
| EP | 2416739 A2 | | 2/2012 |
| EP | 2419050 | | 2/2012 |
| EP | 2444031 A2 | | 4/2012 |
| EP | 2488126 A1 | | 8/2012 |
| EP | 2509538 A2 | | 10/2012 |
| EP | 2522307 A1 | | 11/2012 |
| EP | 2549955 A1 | | 1/2013 |
| EP | 2549956 A1 | | 1/2013 |
| EP | 2566416 A1 | | 3/2013 |
| EP | 2586492 A1 | | 5/2013 |
| EP | 2618784 A2 | | 7/2013 |
| EP | 2623068 A1 | | 8/2013 |
| EP | 2626012 A2 | | 8/2013 |
| EP | 2626013 A2 | | 8/2013 |
| EP | 2629699 A1 | | 8/2013 |
| EP | 2633457 A1 | | 9/2013 |
| EP | 2637659 A1 | | 9/2013 |
| EP | 2641569 A1 | | 9/2013 |
| EP | 2644158 | | 10/2013 |
| EP | 2654624 A1 | | 10/2013 |
| EP | 2656794 A1 | | 10/2013 |
| EP | 2656795 A1 | | 10/2013 |
| EP | 2656795 A1 | | 10/2013 |
| EP | 2656796 A1 | | 10/2013 |
| EP | 2656796 A1 | | 10/2013 |
| EP | 2667823 A1 | | 12/2013 |
| EP | 2670358 A2 | | 12/2013 |
| EP | 2670358 A2 | | 12/2013 |
| EP | 2676640 A1 | | 12/2013 |
| EP | 2688041 A2 | | 1/2014 |
| EP | 2693984 A2 | | 2/2014 |
| EP | 2697721 A2 | | 2/2014 |
| EP | 2713953 A1 | | 4/2014 |
| EP | 2714068 A2 | | 4/2014 |
| EP | 2723272 A2 | | 4/2014 |
| EP | 2723273 A2 | | 4/2014 |
| EP | 2723277 A1 | | 4/2014 |
| EP | 2739214 A2 | | 6/2014 |
| EP | 2741711 A2 | | 6/2014 |
| EP | 2750630 A1 | | 7/2014 |
| EP | 2750631 A1 | | 7/2014 |
| EP | 2755562 A1 | | 7/2014 |
| EP | 2755602 A1 | | 7/2014 |
| EP | 2757962 A1 | | 7/2014 |
| EP | 2777616 A1 | | 9/2014 |
| EP | 2777617 A1 | | 9/2014 |
| EP | 2782523 A1 | | 10/2014 |
| EP | 2785282 A1 | | 10/2014 |
| EP | 2786817 | | 10/2014 |
| EP | 2790609 A1 | | 10/2014 |
| EP | 2793751 A1 | | 10/2014 |
| EP | 2809263 A2 | | 12/2014 |
| EP | 2810620 A1 | | 12/2014 |
| EP | 2814428 A1 | | 12/2014 |
| EP | 2814429 A1 | | 12/2014 |
| EP | 2819617 A1 | | 1/2015 |
| EP | 2819618 A1 | | 1/2015 |
| EP | 2819619 A1 | | 1/2015 |
| EP | 2717803 | | 2/2015 |
| EP | 2833836 A1 | | 2/2015 |
| EP | 2838475 A1 | | 2/2015 |
| EP | 2839815 | | 2/2015 |
| EP | 2844190 | | 3/2015 |
| EP | 2849680 A2 | | 3/2015 |
| EP | 2849681 A1 | | 3/2015 |
| EP | 2852354 A2 | | 4/2015 |
| EP | 2854719 | | 4/2015 |
| EP | 2870933 | | 5/2015 |
| EP | 2873011 A1 | | 5/2015 |
| EP | 2875797 A1 | | 5/2015 |
| EP | 2760375 | | 6/2015 |
| EP | 2882374 A1 | | 6/2015 |
| EP | 2886082 | | 6/2015 |
| EP | 2886083 A1 | | 6/2015 |
| EP | 2886084 A1 | | 6/2015 |
| EP | 2895111 A2 | | 7/2015 |
| EP | 2901966 A1 | | 8/2015 |
| EP | 2907479 A1 | | 8/2015 |
| EP | 2911594 A2 | | 9/2015 |
| EP | 2945572 A1 | | 11/2015 |
| EP | 2948094 A1 | | 12/2015 |
| EP | 2948102 A1 | | 12/2015 |
| EP | 2964152 A1 | | 1/2016 |
| EP | 2967847 A1 | | 1/2016 |
| EP | 2967859 A1 | | 1/2016 |
| EP | 2967860 A1 | | 1/2016 |
| EP | 2967866 A2 | | 1/2016 |
| EP | 2968847 A1 | | 1/2016 |
| EP | 2976043 A1 | | 1/2016 |
| EP | 2981208 | | 2/2016 |
| EP | 2982336 A1 | | 2/2016 |
| EP | 2999433 A1 | | 3/2016 |
| EP | 3003187 A1 | | 4/2016 |
| EP | 3003219 A1 | | 4/2016 |
| EP | 3003220 A1 | | 4/2016 |
| EP | 3010447 A1 | | 4/2016 |
| EP | 3013281 A1 | | 5/2016 |
| EP | 3017792 A1 | | 5/2016 |
| EP | 3021792 A2 | | 5/2016 |
| EP | 3023117 A1 | | 5/2016 |
| EP | 3027143 A1 | | 6/2016 |
| EP | 3033048 A2 | | 6/2016 |
| EP | 3037064 A1 | | 6/2016 |
| EP | 3079633 | | 10/2016 |
| EP | 3229736 | | 11/2016 |
| EP | 2470119 B1 | | 5/2017 |
| EP | 2999436 A4 | | 5/2017 |
| EP | 3184081 | | 6/2017 |
| EP | 3191027 | | 7/2017 |
| EP | 2611389 | | 8/2017 |

(56) References Cited

FOREIGN PATENT DOCUMENTS

| | | |
|---|---|---|
| EP | 3082656 | 8/2017 |
| EP | 3206628 | 8/2017 |
| EP | 2010103 | 9/2017 |
| EP | 2509538 B1 | 9/2017 |
| EP | 3223751 | 10/2017 |
| EP | 3027144 | 11/2017 |
| EP | 3110368 | 11/2017 |
| EP | 3110369 | 11/2017 |
| EP | 3132773 | 11/2017 |
| EP | 3245980 | 11/2017 |
| EP | 3250154 | 12/2017 |
| EP | 3256074 | 12/2017 |
| EP | 3256077 | 12/2017 |
| EP | 3258883 | 12/2017 |
| EP | 3270825 | 1/2018 |
| EP | 3273910 | 1/2018 |
| JP | 6504516 | 5/1994 |
| JP | H10258124 A | 9/1998 |
| JP | 2002509756 A | 4/2002 |
| JP | 2005280917 A | 10/2005 |
| JP | 2008528117 A | 7/2008 |
| JP | 2008541863 A | 11/2008 |
| JP | 2009195712 A | 9/2009 |
| JP | 2010518947 A | 6/2010 |
| JP | 5219518 B2 | 6/2013 |
| WO | WO-1992017118 A1 | 10/1992 |
| WO | WO-1995016407 A1 | 6/1995 |
| WO | WO-1999004730 A1 | 2/1999 |
| WO | WO-1999039648 A1 | 8/1999 |
| WO | WO-1999049799 A1 | 10/1999 |
| WO | WO-2001010343 | 2/2001 |
| WO | WO-2002003892 A1 | 1/2002 |
| WO | WO-2002028421 A1 | 4/2002 |
| WO | WO-2002039908 A2 | 5/2002 |
| WO | WO-2003043685 A2 | 5/2003 |
| WO | WO-2004084746 A2 | 10/2004 |
| WO | WO-2004093728 A2 | 11/2004 |
| WO | WO-2004096097 A2 | 11/2004 |
| WO | WO-2004112657 A1 | 12/2004 |
| WO | WO-2005002466 A2 | 1/2005 |
| WO | WO-2005007219 A2 | 1/2005 |
| WO | WO-2005009285 A2 | 2/2005 |
| WO | WO-2005009506 A2 | 2/2005 |
| WO | WO-2005087140 A1 | 9/2005 |
| WO | WO-2006041877 A2 | 4/2006 |
| WO | WO-2006063199 A2 | 6/2006 |
| WO | WO-2007008371 A2 | 1/2007 |
| WO | WO-2007067820 A2 | 6/2007 |
| WO | 2007098232 A2 | 8/2007 |
| WO | WO-2008022077 A2 | 2/2008 |
| WO | WO-2008028569 A1 | 3/2008 |
| WO | WO-2008035337 A2 | 3/2008 |
| WO | 2008046593 A2 | 4/2008 |
| WO | 2008103722 | 8/2008 |
| WO | WO-2008103497 A2 | 8/2008 |
| WO | WO-2008129405 A2 | 10/2008 |
| WO | WO-2009045338 A1 | 4/2009 |
| WO | 2009091509 | 7/2009 |
| WO | WO-2010006627 A1 | 1/2010 |
| WO | WO-2010008549 A1 | 1/2010 |
| WO | WO-2010057262 A1 | 5/2010 |
| WO | WO-2010080594 A2 | 7/2010 |
| WO | WO-2010098857 A1 | 9/2010 |
| WO | WO-2010099032 A2 | 9/2010 |
| WO | 2010121076 | 10/2010 |
| WO | WO-2010117680 A1 | 10/2010 |
| WO | 2011025981 | 3/2011 |
| WO | WO-2011047168 A1 | 4/2011 |
| WO | WO-2011051043 A1 | 5/2011 |
| WO | WO-2011057087 A1 | 5/2011 |
| WO | WO-2011072084 A2 | 6/2011 |
| WO | WO-2011106137 A1 | 9/2011 |
| WO | WO-2011106544 A1 | 9/2011 |
| WO | WO-2011111047 A2 | 9/2011 |
| WO | WO-2011137531 A1 | 11/2011 |
| WO | WO-2011139747 A1 | 11/2011 |
| WO | WO-2012011018 A1 | 1/2012 |
| WO | WO-2012011108 A2 | 1/2012 |
| WO | WO-2012027487 A2 | 3/2012 |
| WO | WO-2012035279 A1 | 3/2012 |
| WO | WO-2012040655 A2 | 3/2012 |
| WO | 2012052718 | 4/2012 |
| WO | WO-2012047644 A2 | 4/2012 |
| WO | WO-2012055498 A1 | 5/2012 |
| WO | WO-2012087842 A1 | 6/2012 |
| WO | WO-2012095455 A1 | 7/2012 |
| WO | 2012106602 A2 | 8/2012 |
| WO | WO-2012102928 A1 | 8/2012 |
| WO | WO-2012106602 A2 | 8/2012 |
| WO | WO-2012118508 A1 | 9/2012 |
| WO | WO-2012118816 A1 | 9/2012 |
| WO | WO-2012118894 A2 | 9/2012 |
| WO | WO-2012177942 A2 | 12/2012 |
| WO | WO-2013021374 A2 | 2/2013 |
| WO | WO-2013021375 A2 | 2/2013 |
| WO | WO-2013028387 A2 | 2/2013 |
| WO | WO-2013059743 A1 | 4/2013 |
| WO | WO-2013059747 A1 | 4/2013 |
| WO | WO-2013114214 A2 | 8/2013 |
| WO | WO-2013120181 A1 | 8/2013 |
| WO | WO-2013123059 A1 | 8/2013 |
| WO | WO-2013128432 A1 | 9/2013 |
| WO | WO-2013130641 A1 | 9/2013 |
| WO | WO-2013131925 A1 | 9/2013 |
| WO | WO-2013140318 A1 | 9/2013 |
| WO | WO-2013148017 A1 | 10/2013 |
| WO | WO-2013148018 A1 | 10/2013 |
| WO | WO-2013148019 A1 | 10/2013 |
| WO | WO-2013150512 A1 | 10/2013 |
| WO | WO-2013152161 A1 | 10/2013 |
| WO | WO-2013158613 A1 | 10/2013 |
| WO | WO-2013169448 A1 | 11/2013 |
| WO | WO-2013175468 A2 | 11/2013 |
| WO | WO-2013176583 A2 | 11/2013 |
| WO | WO-2013188077 A1 | 12/2013 |
| WO | WO-2013192107 A1 | 12/2013 |
| WO | WO-2014036113 A1 | 3/2014 |
| WO | WO-2014043527 A2 | 3/2014 |
| WO | WO-2014047111 A1 | 3/2014 |
| WO | WO-2014047325 A1 | 3/2014 |
| WO | WO-2014055981 A1 | 4/2014 |
| WO | WO-2014059432 A2 | 4/2014 |
| WO | WO-2014064694 A2 | 5/2014 |
| WO | WO-2014066365 A1 | 5/2014 |
| WO | WO-2014089424 A1 | 6/2014 |
| WO | WO-2014093861 A1 | 6/2014 |
| WO | WO-2014111918 A1 | 7/2014 |
| WO | WO-2014114794 A2 | 7/2014 |
| WO | WO-2014114795 A1 | 7/2014 |
| WO | WO-2014114796 A1 | 7/2014 |
| WO | WO-2014114798 A1 | 7/2014 |
| WO | WO-2014116502 A1 | 7/2014 |
| WO | WO-2014121280 A2 | 8/2014 |
| WO | WO-2014128705 A1 | 8/2014 |
| WO | WO-2014134277 A1 | 9/2014 |
| WO | WO-2014138194 A1 | 9/2014 |
| WO | WO-2014138284 A1 | 9/2014 |
| WO | WO-2014138482 A1 | 9/2014 |
| WO | WO-2014138868 A1 | 9/2014 |
| WO | WO-2014144100 A2 | 9/2014 |
| WO | WO-2014144937 A2 | 9/2014 |
| WO | WO-2014145338 A1 | 9/2014 |
| WO | WO-2014147336 A1 | 9/2014 |
| WO | WO-2014152306 A1 | 9/2014 |
| WO | WO-2014152375 A2 | 9/2014 |
| WO | WO-2014152503 A1 | 9/2014 |
| WO | WO-2014153544 A1 | 9/2014 |
| WO | WO-2014158617 A1 | 10/2014 |
| WO | WO-2014162181 A2 | 10/2014 |
| WO | WO-2014162306 A2 | 10/2014 |
| WO | WO-2014163705 A1 | 10/2014 |
| WO | WO-2014168655 A1 | 10/2014 |
| WO | WO-2014179391 A2 | 11/2014 |
| WO | WO-2014181336 A1 | 11/2014 |

(56) References Cited

FOREIGN PATENT DOCUMENTS

| | | |
|---|---|---|
| WO | WO-2014189974 A1 | 11/2014 |
| WO | 2014200764 A1 | 12/2014 |
| WO | WO-2014191994 A1 | 12/2014 |
| WO | WO-2014194178 A1 | 12/2014 |
| WO | WO-2014201384 A1 | 12/2014 |
| WO | WO-2014201452 A1 | 12/2014 |
| WO | WO-2014205064 A1 | 12/2014 |
| WO | WO-2014207699 A1 | 12/2014 |
| WO | WO-2014210124 A1 | 12/2014 |
| WO | WO-2014210299 A1 | 12/2014 |
| WO | WO-2015009503 A2 | 1/2015 |
| WO | WO-2015020971 A1 | 2/2015 |
| WO | 2015031898 A2 | 3/2015 |
| WO | WO-2015028986 A1 | 3/2015 |
| WO | 2015061558 A2 | 4/2015 |
| WO | WO-2015051430 A1 | 4/2015 |
| WO | WO-2015052663 A1 | 4/2015 |
| WO | WO-2015057407 A1 | 4/2015 |
| WO | WO-2015057735 A1 | 4/2015 |
| WO | WO-2015057995 A2 | 4/2015 |
| WO | WO-2015061378 A1 | 4/2015 |
| WO | WO-2015061431 A1 | 4/2015 |
| WO | WO-2015061463 A1 | 4/2015 |
| WO | WO-2015061533 A1 | 4/2015 |
| WO | WO-2015075128 A1 | 5/2015 |
| WO | WO-2015081775 A1 | 6/2015 |
| WO | WO-2015089334 A1 | 6/2015 |
| WO | WO-2015092554 A2 | 6/2015 |
| WO | WO-2015120122 A2 | 8/2015 |
| WO | WO-2015125024 A2 | 8/2015 |
| WO | WO-2015127264 A1 | 8/2015 |
| WO | WO-2015127283 A1 | 8/2015 |
| WO | WO-2015128739 A2 | 9/2015 |
| WO | WO-2015128741 A2 | 9/2015 |
| WO | WO-2015128747 A2 | 9/2015 |
| WO | WO-2015132667 A1 | 9/2015 |
| WO | WO-2015132668 A1 | 9/2015 |
| WO | WO-2015135050 A1 | 9/2015 |
| WO | WO-2015142648 A1 | 9/2015 |
| WO | WO-2015142834 A1 | 9/2015 |
| WO | WO-2015148241 A1 | 10/2015 |
| WO | 2015179181 | 11/2015 |
| WO | WO-2015171190 A1 | 11/2015 |
| WO | WO-2015171743 A2 | 11/2015 |
| WO | WO-2015191604 | 12/2015 |
| WO | WO-2015191839 A1 | 12/2015 |
| WO | WO-2015195823 A1 | 12/2015 |
| WO | 2016005803 A2 | 1/2016 |
| WO | WO-2016011185 A1 | 1/2016 |
| WO | WO-2016020918 A1 | 2/2016 |
| WO | WO-2016027272 A1 | 2/2016 |
| WO | WO-2016059533 A1 | 4/2016 |
| WO | WO-2016065158 A1 | 4/2016 |
| WO | WO-2016073741 A1 | 5/2016 |
| WO | WO-2016083551 A1 | 6/2016 |
| WO | WO-2016093877 A1 | 6/2016 |
| WO | WO-2016097337 A1 | 6/2016 |
| WO | WO-2016108181 A1 | 7/2016 |
| WO | 2016133950 | 8/2016 |
| WO | WO-2017062640 | 4/2017 |
| WO | 2017087701 | 5/2017 |
| WO | 2017096157 | 6/2017 |
| WO | 2017100927 | 6/2017 |
| WO | 2017101232 | 6/2017 |
| WO | 2017117388 | 7/2017 |
| WO | 2017127939 | 8/2017 |
| WO | 2017136287 | 8/2017 |
| WO | 2017136596 | 8/2017 |
| WO | 2017165810 | 9/2017 |
| WO | 2017192960 | 11/2017 |
| WO | 2017196511 | 11/2017 |
| WO | 2017196909 | 11/2017 |
| WO | 2017196977 | 11/2017 |
| WO | 2017197064 | 11/2017 |
| WO | 2017197065 | 11/2017 |
| WO | 2017189040 | 12/2017 |
| WO | 2017218671 | 12/2017 |
| WO | 2018017886 | 1/2018 |

OTHER PUBLICATIONS

International Search Report and Written Opinion dated Jul. 11, 2018 for PCT Application No. PCT/US2018/027990, 15 pages.
International Search Report and Written Opinion dated Jun. 28, 2018 for PCT Application No. PCT/US2018/027983, 15 pages.
International Search Report and Written Opinion dated Aug. 3, 2018 for PCT Application No. PCT/US2018035086, 15 pages.
International Search Report and Written Opinion dated Aug. 9, 2018 for PCT Application No. PCT/US2018/035081, 11 pages.
Bernard et al., "Aortic Valve Area Evolution After Percutaneous Aortic Valvuloplasty," European Heart Journal, Jul. 1990, vol. 11 (2), pp. 98-107.
BlueCross BlueShield of Northern Carolina Corporate Medical Policy "Balloon valvuloplasty, Percutaneous", (Jun. 1994).
Cimino et al., "Physics of Ultrasonic Surgery Using Tissue Fragmentation: Part I and Part II", Ultrasound in Medicine and Biogyl, Jun. 1996, vol. 22 (1), pp. 89-100, and pp. 101-117.
Cimino, "Ultrasonic Surgery: Power Quantification and Efficiency Optimization", Aesthetic Surgery Journal, Feb. 2001, pp. 233-241.
Cowell et al., "A Randomized Trial of Intensive Lipid-Lowering Therapy in Calcific Aortic Stenosis," NEJM, Jun. 2005, vol. 352 (23), pp. 2389-2397.
De Korte et al., "Characterization of Plaque Components and Vulnerability with Intravascular Ultrasound Elastography", Phys. Med. Biol., Feb. 2000, vol. 45, pp. 1465-1475.
European Search Report dated Mar. 13, 2015 for European Application. No. 05853460.3.
Feldman, "Restenosis Following Successful Balloon Valvuloplasty: Bone Formation in Aortic Valve Leaflets", Cathet Cardiovasc Diagn, May 1993, vol. 29 (1), pp. 1-7.
Fitzgerald et al., "Intravascular Sonotherapy Decreased Neointimal Hyperplasia After Stent Implantation in Swine", Circulation, Feb. 2001, vol. 103, pp. 1828-1831.
Freeman et al., "Ultrasonic Aortic Valve Decalcification: Serial Doppler Echocardiographic Follow Up", J Am Coll Cardiol., Sep. 1990, vol. 16 (3), pp. 623-630.
Greenleaf et al., "Selected Methods for Imaging Elastic Properties of Biological Tissues", Annu. Rev. Biomed. Eng., Apr. 2003, vol. 5, pp. 57-78.
Gunn et al., "New Developments in Therapeutic Ultrasound-Assisted Coronary Angioplasty", Curr Interv Cardiol Rep., Dec. 1990, vol. 1 (4), pp. 281-290.
Guzman et al., "Bioeffects Caused by Changes in Acoustic Cavitation Bubble Density and Cell Concentration: A Unified Explanation Based on Cell-to-Bubble Ratio and Blast Radius", Ultrasound in Med. & Biol., Mar. 2003, vol. 29 (8), pp. 1211-1222.
Hallgrimsson et al., "Chronic Non-Rheumatic Aortic Valvular Disease: a Population Study Based on Autopsies", J Chronic Dis., Jun. 1979, vol. 32 (5), pp. 355-363.
Isner et al., "Contrasting Histoarchitecture of Calcified Leaflets from Stenotic Bicuspid Versus Stenotic Tricuspid Aortic Valves", J Am Coll Cardiol., Apr. 1990, vol. 15 (5), p. 1104-1108.
Lung et al., "A Prospective Survey of Patients with Valvular Heart Disease in Europe: The Euro Heart Survey on Valvular Heart Disease", Euro Heart Journal, Mar. 2003, vol. 24, pp. 1231-1243.
McBride et al "Aortic Valve Decalcification", J Thorac Cardiovas-Surg, Jul. 1990, vol. 100, pp. 36-42.
Miller et al., "Lysis and Sonoporation of Epidermoid and Phagocytic Monolayer Cells by Diagnostic Ultrasound Activation of Contrast Agent Gas Bodies", Ultrasound in Med. & Biol., May 2007, vol. 27 (8), pp. 1107-1113.
Mohler, "Mechanisms of Aortic Valve Calcificaion", Am J Cardiol, Dec. 2004, vol. 94 (11), pp. 1396-1402.
Otto et al., "Three-Year Outcome After Balloon Aortic Valvuloplasty. Insights into Prognosis of Valvular Aortic Stenosis", Circulation, Feb. 1994, vol. 89, pp. 642-650.

(56) References Cited

OTHER PUBLICATIONS

Passik et al., "Temporal Changes in the Causes of Aortic Stenosis: A Surgical Pathologic Study of 646 Cases", Mayo Clin Proc, Feb. 1987, vol. 62, pp. 19-123.
Quaden et al., "Percutaneous Aortic Valve Replacement: Resection Before Implantation", Eur J Cardiothorac Surg, Jan. 2005, vol. 27, pp. 836-840.
Riebman et al., "New Concepts in the Management of Patients with Aortic Valve Disease", Abstract, Valvular Heart Disease, JACC, Mar. 2004, p. 34A.
Rosenschein et al., "Percutaneous Transluminal Therapy of Occluded Saphenous Vein Grafts" Circulation, Jan. 1999, vol. 99, pp. 26-29.
Sakata et al., "Percutaneous Balloon Aortic Valvuloplasty: Antegrade Transseptal vs. Conventional Retrograde Transarterial Approach", Catheter Cardiovasc Interv., Mar. 2005, vol. 64 (3), pp. 314-321.
Sasaki et al., "Scanning Electron Microscopy and Fourier Transformed Infrared Spectroscopy Analysis of Bone Removal Using Er:YAG and CO2 Lasers", J Periodontol., Jun. 2002, vol. 73 (6), pp. 643-652.
Search Report and Written Opinion dated Dec. 10, 2012 for PCT Application No. PCT/US2012/043636.
Search Report and Written Opinion dated Dec. 6, 2016 for PCT Application No. PCT/US2016/047831.
Search Report and Written Opinion dated Apr. 19, 2014 PCT Application No. PCT/US2012/061215.
Search Report and Written Opinion dated Apr. 19, 2014 PCT Application No. PCT/US2012/061219.
Search Report and Written Opinion dated Mar. 2, 2015 for PCT Application No. PCT/US2014/029549.
Search Report and Written Opinion dated May 1, 2012 for PCT Application No. PCT/US2011/065627.
Search Report and Written Opinion dated May 22, 2007 for PCT Application No. PCT/US2005/044543.
Search Report and Written Opinion dated Oct. 20, 2014 for PCT Application No. PCT/US2014/038849.
Search Report and Written Opinion dated Sep. 4, 2014 for PCT Application No. PCT/US2014/014704.
The CoreValve System Medtronic, 2012, 4 Pages.
Van Den Brand et al., "Histological Changes in the Aortic Valve after Balloon Dilation: Evidence for a Delayed Healing Process", Br Heart J, Jun. 1992,vol. 67, pp. 445-459.
Verdaadadonk et al., "The Mechanism of Action of the Ultrasonic Tissue Resectors Disclosed Using High-Speed and Thermal Imaging Techniques", SPIE, Jan. 1999, vol. 3594, pp. 221-231.
Voelker et al., "Inoperative Valvuloplasty in Calcific Aortic Stenosis: a Study Comparing the Mechanism of a Novel Expandable Device with Conventional Balloon Dilation", Am Heart J., Nov. 1991, vol. 122 (5), pp. 1327-1333.
Waller et al., "Catheter Balloon Valvuloplasty of Stenotic Aortic Valves. Part II: Balloon Valvuloplasty During Life Subsequent Tissue Examination", Clin Cardiol., Nov. 1991, vol. 14 (11), pp. 924-930.
Wang, "Balloon Aortic Valvuloplasty", Prog Cardiovasc Dis., Jul.-Aug. 1997, vol. 40 (1), pp. 27-36.
Wilson et al., "Elastography—The movement Begins", Phys. Med. Biol., Jun. 2000, vol. 45, pp. 1409-1421.
Yock et al, "Catheter-Based Ultrasound Thrombolysis", Circulation, Mar. 1997, vol. 95 (6), pp. 1411-1416.
U.S. Appl. No. 16/288,679, filed Feb. 28, 2019, naming inventor Deem et al.

\* cited by examiner

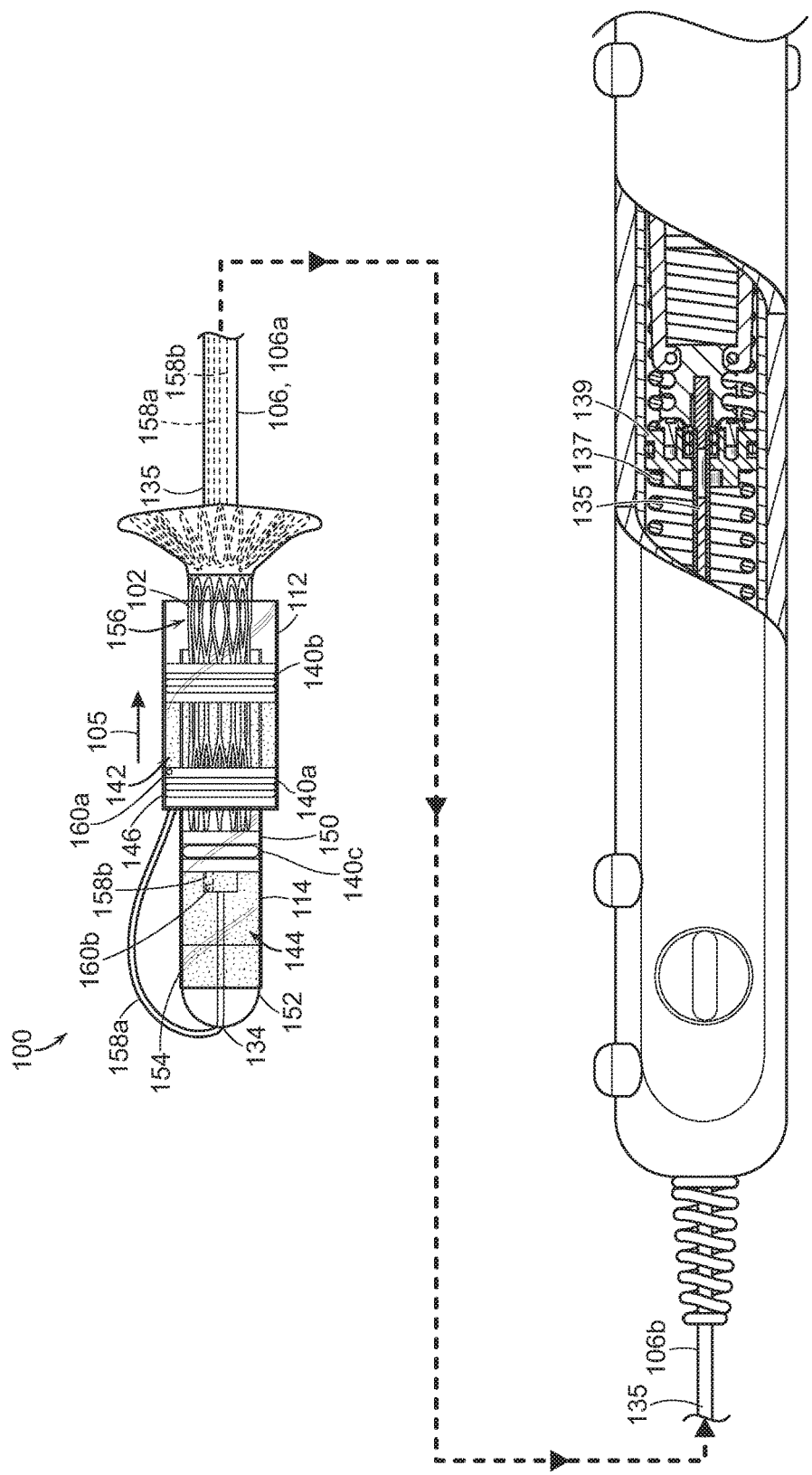

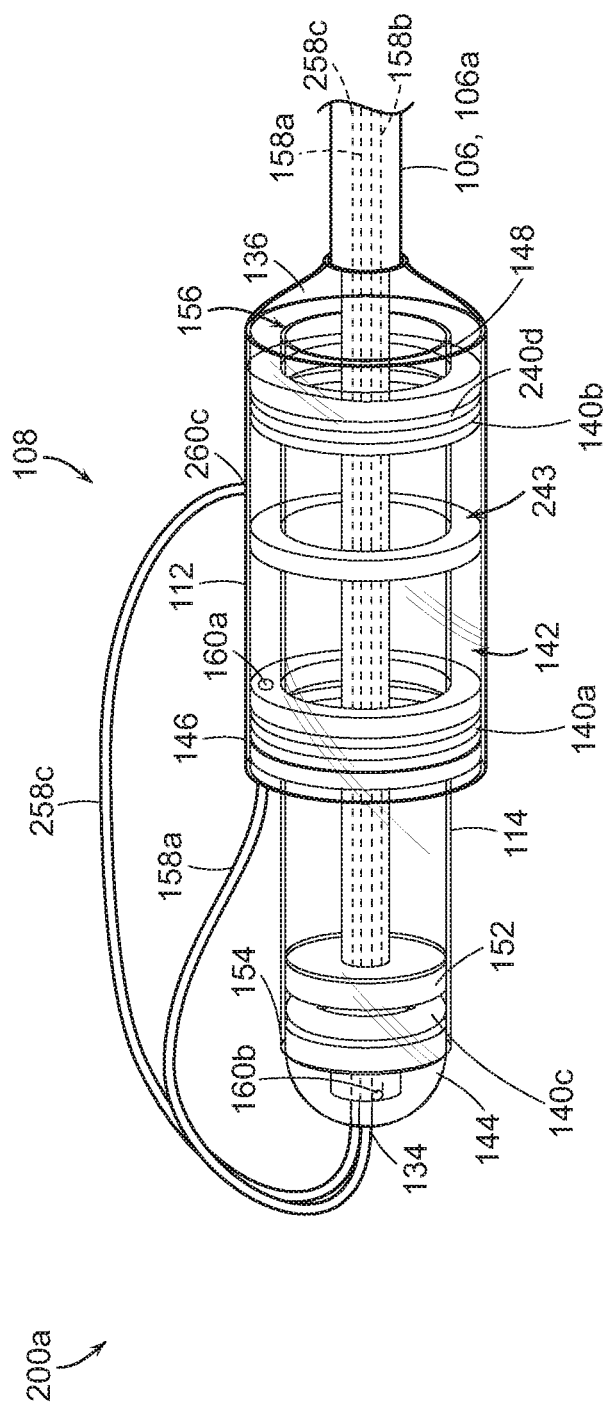

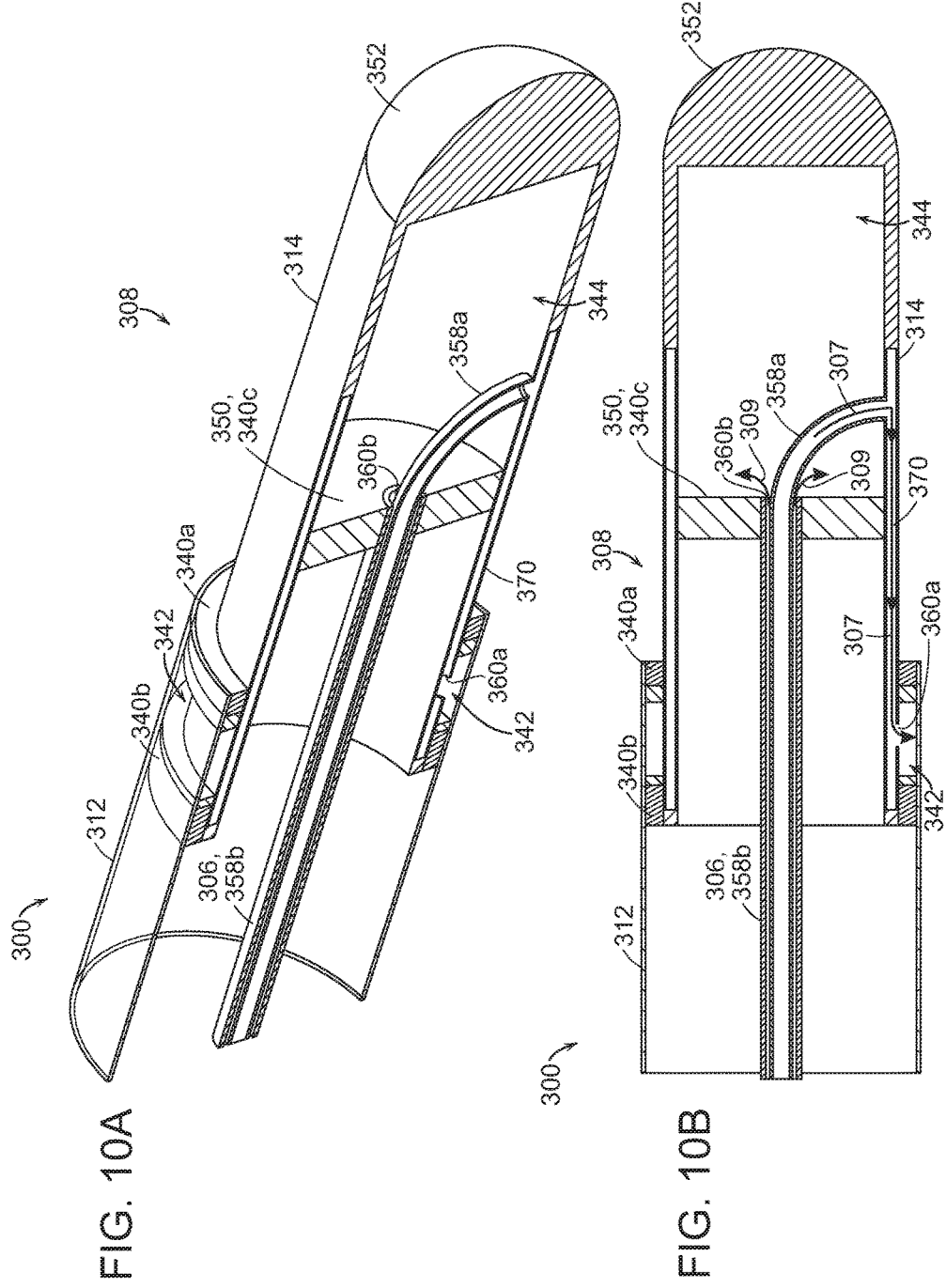

DELIVERY SYSTEMS WITH TELESCOPING CAPSULES FOR DEPLOYING PROSTHETIC HEART VALVE DEVICES AND ASSOCIATED METHODS

TECHNICAL FIELD

The present technology relates generally to systems for delivering prosthetic heart valve devices. In particular, several embodiments of the present technology are related to delivery systems with telescoping capsules for percutaneously delivering prosthetic heart valve devices and associated methods.

BACKGROUND

Heart valves can be affected by several conditions. For example, mitral valves can be affected by mitral valve regurgitation, mitral valve prolapse and mitral valve stenosis. Mitral valve regurgitation is abnormal leaking of blood from the left ventricle into the left atrium caused by a disorder of the heart in which the leaflets of the mitral valve fail to coapt into apposition at peak contraction pressures. The mitral valve leaflets may not coapt sufficiently because heart diseases often cause dilation of the heart muscle, which in turn enlarges the native mitral valve annulus to the extent that the leaflets do not coapt during systole. Abnormal backflow can also occur when the papillary muscles are functionally compromised due to ischemia or other conditions. More specifically, as the left ventricle contracts during systole, the affected papillary muscles do not contract sufficiently to effect proper closure of the leaflets.

Mitral valve prolapse is a condition when the mitral leaflets bulge abnormally up in to the left atrium. This can cause irregular behavior of the mitral valve and lead to mitral valve regurgitation. The leaflets may prolapse and fail to coapt because the tendons connecting the papillary muscles to the inferior side of the mitral valve leaflets (chordae tendineae) may tear or stretch. Mitral valve stenosis is a narrowing of the mitral valve orifice that impedes filling of the left ventricle in diastole.

Mitral valve regurgitation is often treated using diuretics and/or vasodilators to reduce the amount of blood flowing back into the left atrium. Surgical approaches (open and intravascular) for either the repair or replacement of the valve have also been used to treat mitral valve regurgitation. For example, typical repair techniques involve cinching or resecting portions of the dilated annulus. Cinching, for example, includes implanting annular or peri-annular rings that are generally secured to the annulus or surrounding tissue. Other repair procedures suture or clip the valve leaflets into partial apposition with one another.

Alternatively, more invasive procedures replace the entire valve itself by implanting mechanical valves or biological tissue into the heart in place of the native mitral valve. These invasive procedures conventionally require large open thoracotomies and are thus very painful, have significant morbidity, and require long recovery periods. Moreover, with many repair and replacement procedures, the durability of the devices or improper sizing of annuloplasty rings or replacement valves may cause additional problems for the patient. Repair procedures also require a highly skilled cardiac surgeon because poorly or inaccurately placed sutures may affect the success of procedures.

Less invasive approaches to aortic valve replacement have been implemented in recent years. Examples of pre-assembled, percutaneous prosthetic valves include, e.g., the CoreValve Revalving® System from Medtronic/Corevalve Inc. (Irvine, Calif., USA) and the EdwardsSapien® Valve from Edwards Lifesciences (Irvine, Calif., USA). Both valve systems include an expandable frame and a tri-leaflet bio-prosthetic valve attached to the expandable frame. The aortic valve is substantially symmetric, circular, and has a muscular annulus. The expandable frames in aortic applications have a symmetric, circular shape at the aortic valve annulus to match the native anatomy, but also because tri-leaflet prosthetic valves require circular symmetry for proper coaptation of the prosthetic leaflets. Thus, aortic valve anatomy lends itself to an expandable frame housing a replacement valve since the aortic valve anatomy is substantially uniform, symmetric, and fairly muscular. Other heart valve anatomies, however, are not uniform, symmetric or sufficiently muscular, and thus transvascular aortic valve replacement devises may not be well suited for other types of heart valves.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. The headings provided herein are for convenience only.

FIGS. 8A-8D are a series of illustrations showing a distal portion of the delivery system of FIGS. 6-7B deploying and resheathing a prosthetic heart valve device in accordance with embodiments of the present technology.

FIG. 9A is a side isometric view of a distal portion of a delivery system configured in accordance with embodiments of the present technology.

FIG. 10A is a partial cut-away isometric view of a distal portion of a delivery system configured in accordance with a further embodiment of the present technology.

FIG. 10B is a cross-sectional view of the distal portion of the delivery system of FIG. 10A.

DETAILED DESCRIPTION

Figure 1:
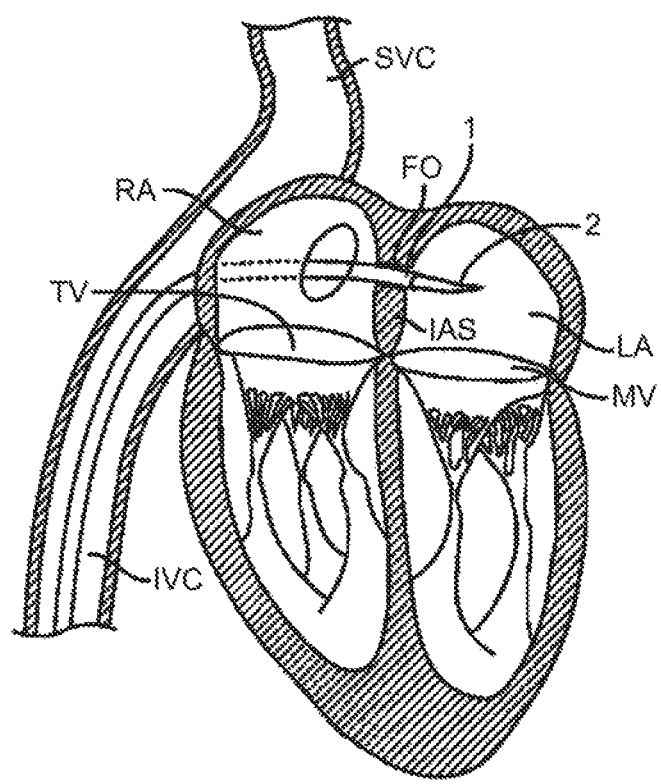
FIG. 1 is a schematic, cross-sectional illustration of the heart showing an antegrade approach to the native mitral valve from the venous vasculature in accordance with various embodiments of the present technology.

The present technology is generally directed to delivery systems with telescoping capsules for deploying prosthetic heart valve devices and associated methods. Specific details of several embodiments of the present technology are described herein with reference to FIGS. 1-26. Although many of the embodiments are described with respect to devices, systems, and methods for delivering prosthetic heart valve devices to a native mitral valve, other applications and other embodiments in addition to those described herein are within the scope of the present technology. For example, at least some embodiments of the present technology may be useful for delivering prosthetics to other valves, such as the tricuspid valve or the aortic valve. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

With regard to the terms "distal" and "proximal" within this description, unless otherwise specified, the terms can reference relative positions of portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a location where blood flows into the device (e.g., inflow region), and distal can refer to a downstream position or a location where blood flows out of the device (e.g., outflow region).

Overview

Several embodiments of the present technology are directed to delivery systems and mitral valve replacement devices that address the unique challenges of percutaneously replacing native mitral valves and are well-suited to be recaptured in a percutaneous delivery device after being partially deployed for repositioning or removing the device. Compared to replacing aortic valves, percutaneous mitral valve replacement faces unique anatomical obstacles that render percutaneous mitral valve replacement significantly more challenging than aortic valve replacement. First, unlike relatively symmetric and uniform aortic valves, the mitral valve annulus has a non-circular D-shape or kidney-like shape, with a non-planar, saddle-like geometry often lacking symmetry. The complex and highly variable anatomy of mitral valves makes it difficult to design a mitral valve prosthesis that conforms well to the native mitral annulus of specific patients. As a result, the prosthesis may not fit well with the native leaflets and/or annulus, which can leave gaps that allows backflow of blood to occur. For example, placement of a cylindrical valve prosthesis in a native mitral valve may leave gaps in commissural regions of the native valve through which perivalvular leaks may occur.

Current prosthetic valves developed for percutaneous aortic valve replacement are unsuitable for use in mitral valves. First, many of these devices require a direct, structural connection between the stent-like structure that contacts the annulus and/or leaflets and the prosthetic valve. In several devices, the stent posts which support the prosthetic valve also contact the annulus or other surrounding tissue. These types of devices directly transfer the forces exerted by the tissue and blood as the heart contracts to the valve support and the prosthetic leaflets, which in turn distorts the valve support from its desired cylindrical shape. This is a concern because most cardiac replacement devices use tri-leaflet valves, which require a substantially symmetric, cylindrical support around the prosthetic valve for proper opening and closing of the three leaflets over years of life. As a result, when these devices are subject to movement and forces from the annulus and other surrounding tissues, the prostheses may be compressed and/or distorted causing the prosthetic leaflets to malfunction. Moreover, a diseased mitral annulus is much larger than any available prosthetic aortic valve. As the size of the valve increases, the forces on the valve leaflets increase dramatically, so simply increasing the size of an aortic prosthesis to the size of a dilated mitral valve annulus would require dramatically thicker, taller leaflets, and might not be feasible.

In addition to its irregular, complex shape, which changes size over the course of each heartbeat, the mitral valve annulus lacks a significant amount of radial support from surrounding tissue. Compared to aortic valves, which are completely surrounded by fibro-elastic tissue that provides sufficient support for anchoring a prosthetic valve, mitral valves are bound by muscular tissue on the outer wall only. The inner wall of the mitral valve anatomy is bound by a thin vessel wall separating the mitral valve annulus from the inferior portion of the aortic outflow tract. As a result, significant radial forces on the mitral annulus, such as those imparted by an expanding stent prostheses, could lead to collapse of the inferior portion of the aortic tract. Moreover, larger prostheses exert more force and expand to larger dimensions, which exacerbates this problem for mitral valve replacement applications.

The chordae tendineae of the left ventricle may also present an obstacle in deploying a mitral valve prosthesis. Unlike aortic valves, mitral valves have a maze of cordage under the leaflets in the left ventricle that restrict the movement and position of a deployment catheter and the replacement device during implantation. As a result, deploying, positioning and anchoring a valve replacement device on the ventricular side of the native mitral valve annulus is complicated.

Embodiments of the present technology provide systems, methods and apparatus to treat heart valves of the body, such as the mitral valve, that address the challenges associated with the anatomy of the mitral valve and provide for repositioning and removal of a partially deployed device. The apparatus and methods enable a percutaneous approach using a catheter delivered intravascularly through a vein or artery into the heart, or through a cannula inserted through the heart wall. For example, the apparatus and methods are particularly well-suited for trans-septal and trans-apical approaches, but can also be trans-atrial and direct aortic delivery of a prosthetic replacement valve to a target location in the heart. Additionally, the embodiments of the devices and methods as described herein can be combined with many known surgeries and procedures, such as known methods of accessing the valves of the heart (e.g., the mitral valve or triscuspid valve) with antegrade or retrograde approaches, and combinations thereof.

The systems and methods described herein facilitate delivery of a prosthetic heart valve device using trans-septal delivery approaches to a native mitral valve and allow resheathing of the prosthetic heart valve device after partial deployment of the device to reposition and/or remove the device. The delivery systems can include a telescoping delivery capsule that has a first housing and a second housing slidably disposed within at least a portion of the first housing. During deployment, the first housing moves in a distal direction over the second housing to release a portion of the prosthetic heart valve device, and then the first and second housings move together in a distal direction to fully deploy the prosthetic heart valve device. This telescoping arrangement of the first and second housings requires the delivery capsule to traverse a short overall longitudinal distance relative to the device positioned therein for device deployment and, therefore, facilitates deployment within the constraints of native anatomy surrounding the mitral valve. In addition, when in the initial delivery state, the disclosed telescoping delivery capsules can have a short overall length relative to the length of the prosthetic heart valve device stored therein, which facilitates delivery along tightly curved paths necessary to access the native mitral valve via trans-septal delivery. The disclosed delivery systems can also be used to delivery other medical devices to other target sites with native anatomy that benefits from a compact delivery capsule and reduced longitudinal translation for deployment.

Access to the Mitral Valve

To better understand the structure and operation of valve replacement devices in accordance with the present technology, it is helpful to first understand approaches for implanting the devices. The mitral valve or other type of atrioventricular valve can be accessed through the patient's vasculature in a percutaneous manner. By percutaneous it is meant that a location of the vasculature remote from the heart is accessed through the skin, typically using a surgical cut down procedure or a minimally invasive procedure, such as using needle access through, for example, the Seldinger technique. The ability to percutaneously access the remote vasculature is well known and described in the patent and medical literature. Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a cannula via a trans-apical approach. Depending on the approach, the interventional tools and supporting catheter(s) may be advanced to the heart intravascularly and positioned adjacent the target cardiac valve in a variety of manners, as described herein.

FIG. 1 illustrates a stage of a trans-septal approach for implanting a valve replacement device. In a trans-septal approach, access is via the inferior vena cava IVC or superior vena cava SVC, through the right atrium RA, across the inter-atrial septum IAS, and into the left atrium LA above the mitral valve MV. As shown in FIG. 1, a catheter 1 having a needle 2 moves from the inferior vena cava IVC into the right atrium RA. Once the catheter 1 reaches the anterior side of the inter-atrial septum IAS, the needle 2 advances so that it penetrates through the septum, for example at the fossa ovalis FO or the foramen ovale into the left atrium LA. At this point, a guidewire replaces the needle 2 and the catheter 1 is withdrawn.

Figure 2:
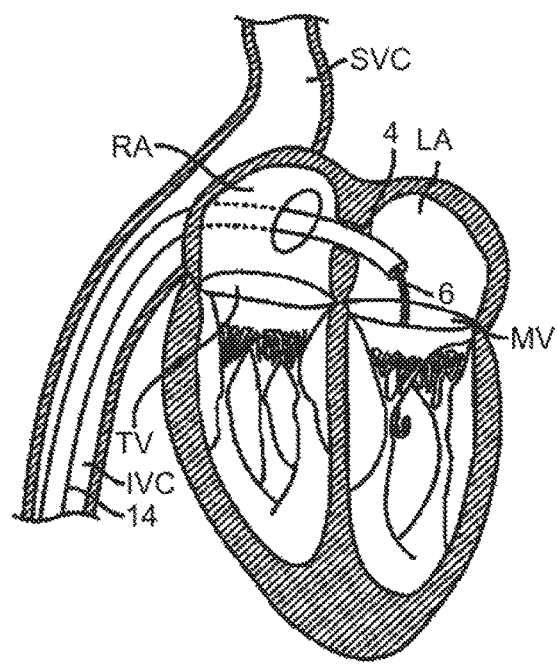
FIG. 2 is a schematic, cross-sectional illustration of the heart showing access through the inter-atrial septum (IAS) maintained by the placement of a guide catheter over a guidewire in accordance with various embodiments of the present technology.

FIG. 2 illustrates a subsequent stage of a trans-septal approach in which guidewire 6 and guide catheter 4 pass through the inter-atrial septum IAS. The guide catheter 4 provides access to the mitral valve for implanting a valve replacement device in accordance with the technology.

In an alternative antegrade approach (not shown), surgical access may be obtained through an intercostal incision, preferably without removing ribs, and a small puncture or incision may be made in the left atrial wall. A guide catheter passes through this puncture or incision directly into the left atrium, sealed by a purse string-suture.

The antegrade or trans-septal approach to the mitral valve, as described above, can be advantageous in many respects. For example, antegrade approaches will usually enable more precise and effective centering and stabilization of the guide catheter and/or prosthetic valve device. The antegrade approach may also reduce the risk of damaging the chordae tendinae or other subvalvular structures with a catheter or other interventional tool. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 3:
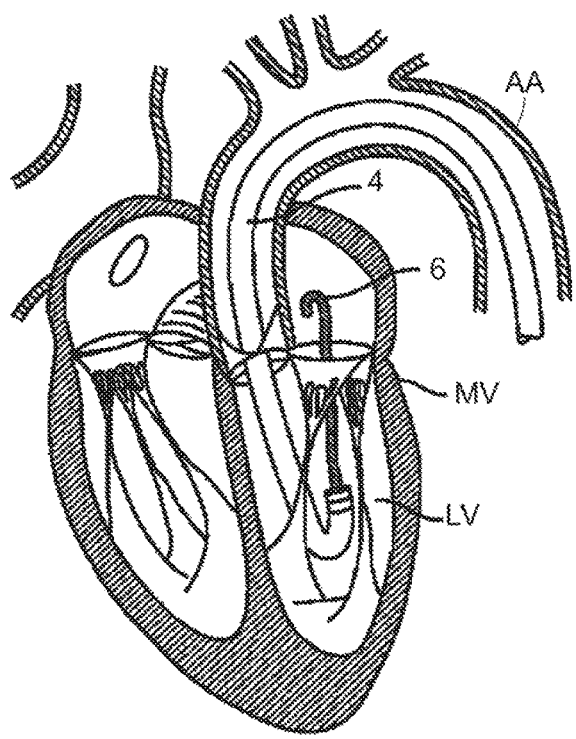
FIGS. 3 and 4 are schematic, cross-sectional illustrations of the heart showing retrograde approaches to the native mitral valve through the aortic valve and arterial vasculature in accordance with various embodiments of the present technology.
Figure 4:
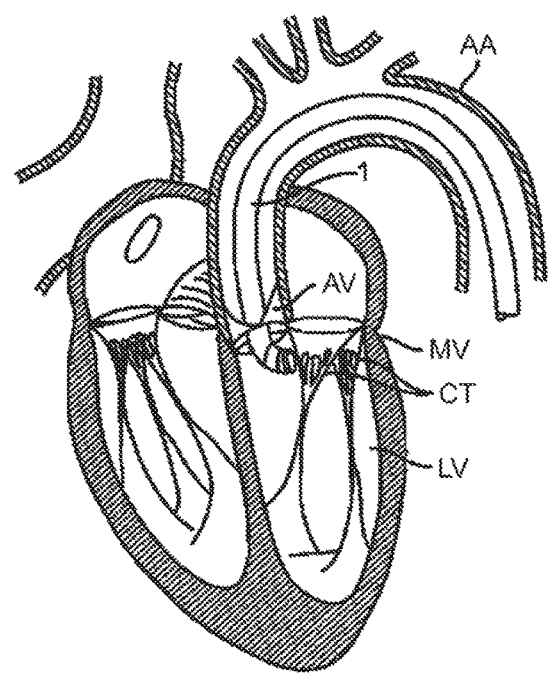

FIGS. 3 and 4 show examples of a retrograde approaches to access the mitral valve. Access to the mitral valve MV may be achieved from the aortic arch AA, across the aortic valve AV, and into the left ventricle LV below the mitral valve MV. The aortic arch AA may be accessed through a conventional femoral artery access route or through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, preferably intercostally without removing ribs, and placing a guide catheter through a puncture in the aorta itself. The guide catheter 4 affords subsequent access to permit placement of the prosthetic valve device, as described in more detail herein. Retrograde approaches advantageously do not need a trans-septal puncture. Cardiologists also more commonly use retrograde approaches, and thus retrograde approaches are more familiar.

Figure 5:
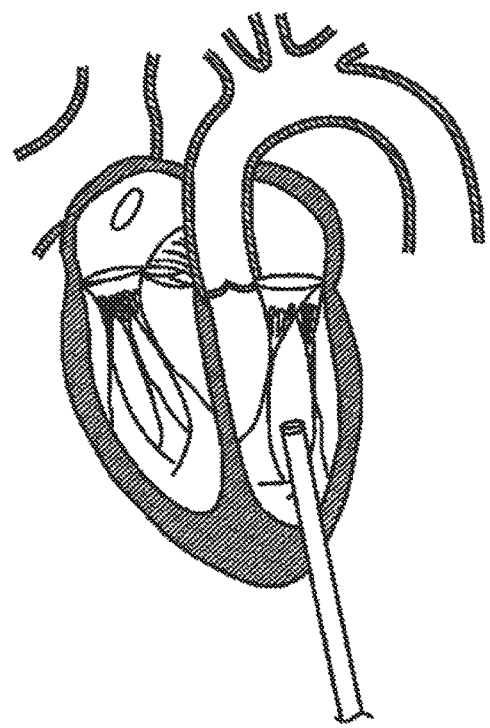
FIG. 5 is a schematic, cross-sectional illustration of the heart showing an approach to the native mitral valve using a trans-apical puncture in accordance with various embodiments of the present technology.

FIG. 5 shows a trans-apical approach via a trans-apical puncture. In this approach, access to the heart is via a thoracic incision, which can be a conventional open thoracotomy or sternotomy, or a smaller intercostal or sub-xyphoid incision or puncture. An access cannula is then placed through a puncture in the wall of the left ventricle at or near the apex of the heart. The catheters and prosthetic devices of the invention may then be introduced into the left ventricle through this access cannula. The trans-apical approach provides a shorter, straighter, and more direct path to the mitral or aortic valve. Further, because it does not involve intravascular access, the trans-apical approach does not require training in interventional cardiology to perform the catheterizations required in other percutaneous approaches.

Selected Embodiments of Delivery Systems for Prosthetic Heart Valve Devices

Figure 6:
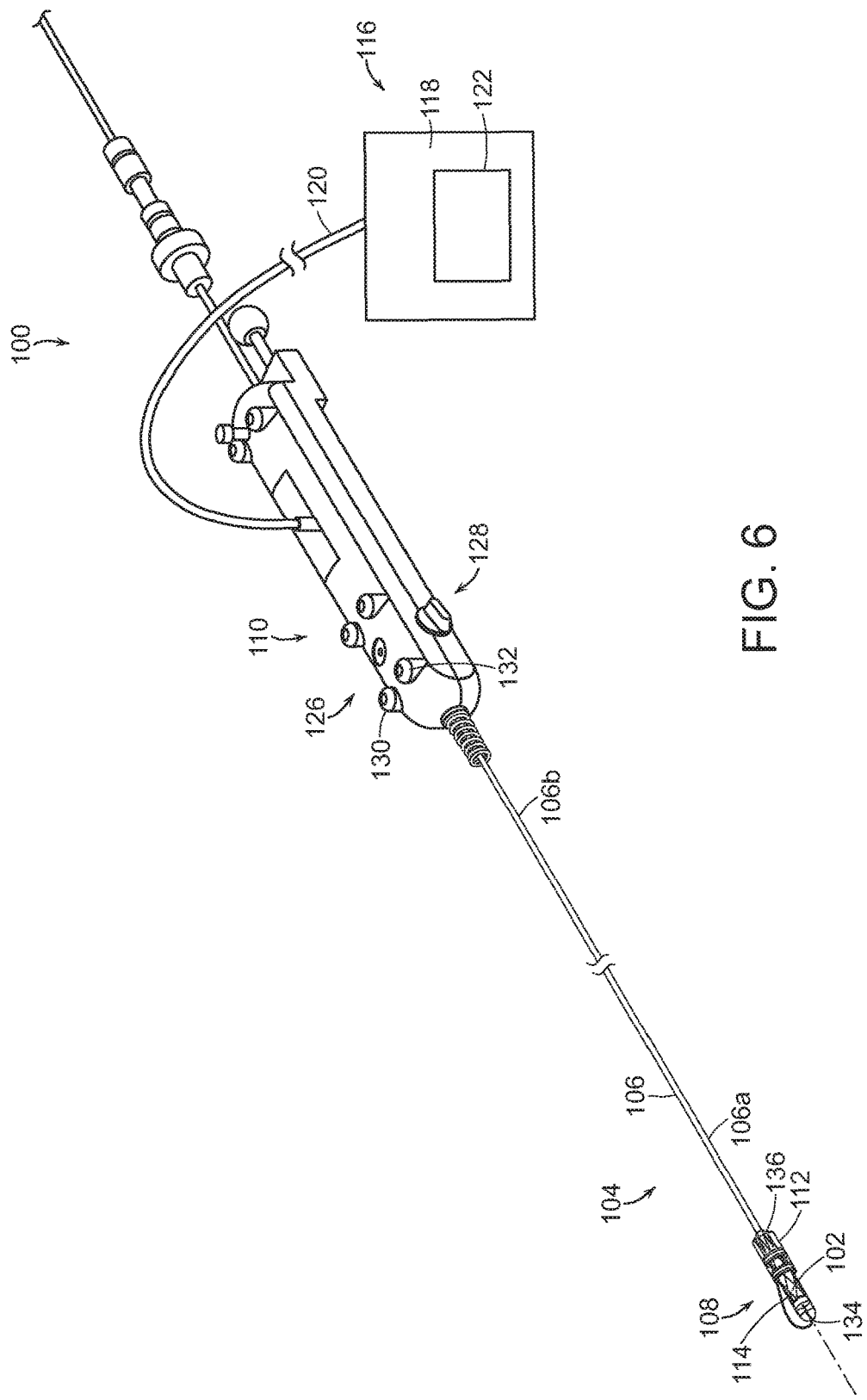
FIG. 6 is an isometric view of a delivery system for a prosthetic heart valve device configured in accordance with an embodiment of the present technology.

FIG. 6 is an isometric view of a delivery system 100 for a prosthetic heart valve device 102 ("device 102"; shown schematically in broken lines) configured in accordance with an embodiment of the present technology. The delivery system 100 includes a catheter 104 having an elongated catheter body 106 ("catheter body 106") with a distal portion 106a carrying a delivery capsule 108 and a proximal portion 106b coupled to a control unit or handle assembly 110. The delivery capsule 108 can move between a containment configuration for holding the device 102 in an unexpanded state during delivery of the device 102 and a deployment configuration in which the device 102 is at least partially expanded from the capsule 108. As described in further detail below, the delivery capsule 108 includes a first housing 112 and a second housing 114 slidably disposed within at least a portion of the first housing 112. During a first deployment stage, the first housing 112 moves in a distal direction over the second housing 114 to release a first portion of the device 102 from the delivery capsule 108, and during a second deployment stage the second housing 114 and the first housing 112 move together in a distal direction to release a second portion of the device 102 from the delivery capsule 108 (e.g., fully release the device 102 from the delivery capsule 108). After partial deployment of the device 102, the telescoping delivery capsule 108 can optionally resheathe at least a portion of the device 102 by urging the first housing 112 and/or the second housing 114 in a proximal direction back over at least a portion of the device 102. The partial or full resheathing of the device 102 allows for repositioning of the device 102 relative to the native mitral valve after a portion of the device 102 has been expanded and contacted tissue of the native valve.

The handle assembly 110 can include a control assembly 126 to initiate deployment of the device 102 from the telescoping delivery capsule 108 at the target site. The control assembly 126 may include rotational elements, buttons, levers, and/or other actuators that allow a clinician to control rotational position of the delivery capsule 108, as well as the deployment and/or resheathing mechanisms of the delivery system 100. For example, the illustrated control assembly 126 includes a first actuator 130 operably coupled to the first housing 112 via the catheter body 106 to control distal and proximal movement of the first housing 112 and a second actuator 132 operably coupled to the second housing 114 via the catheter body 106 to control proximal and distal movement of the second housing 114. In other embodiments, a single actuator, more than two actuators, and/or other features can be used to initiate movement of the first and second housings 112 and 114. The handle assembly 110 can also include a steering mechanism 128 that provides steering capability (e.g., 360 degree rotation of the delivery capsule 108, 180 degree rotation of the delivery capsule 108, 3-axis steering, 2-axis steering, etc.) for delivering the delivery capsule 108 to a target site (e.g., to a native mitral valve). The steering mechanism 128 can be used to steer the catheter 104 through the anatomy by bending the distal portion 106a of the catheter body 106 about a transverse axis. In other embodiments, the handle assembly 110 may include additional and/or different features that facilitate delivering the device 102 to the target site. In certain embodiments, the catheter 104 can be configured to travel over a guidewire 124, which can be used to guide the delivery capsule 108 into the native mitral valve.

As shown in FIG. 6, the system 100 can also include a fluid assembly 116 configured to supply fluid to and receive fluid from the catheter 104 to hydraulically move the first and second housings 112 and 114 and thereby deploy the device 102. The fluid assembly 116 includes a fluid source 118 and a fluid line 120 fluidically coupling the fluid source 118 to the catheter 104. The fluid source 118 may include a flowable substance (e.g., water, saline, etc.) contained in one or more reservoirs. The fluid line 120 can include one or more hoses, tubes, multiple fluid lines within a hose or tube, or other components (e.g., connectors, valves, etc.) through which the flowable substance can pass from the fluid source 118 to the catheter 104 and/or through which the flowable substance can drain from the catheter 104 to the fluid source 118. The fluid assembly 116 can also include one or more pressurization devices (e.g., a pump), fluid connectors, fittings, valves, and/or other fluidic components that facilitate moving the fluid to and/or from the fluid source 118. As explained in further detail below, the movement of the flowable substance to and from the fluid assembly 116 can be used to deploy the device 102 from the delivery capsule 108 and/or resheathe the device 102 after at least partial deployment. In other embodiments, mechanical means, such as tethers and springs, can be used to move the delivery capsule 108 between the deployment and containment configurations. In further embodiments, both fluidic and mechanical means can initiate deployment and resheathing.

In certain embodiments, the fluid assembly 116 may comprise a controller 122 that controls the movement of fluid to and from the catheter 104. The controller 122 can include, without limitation, one or more computers, central processing units, processing devices, microprocessors, digital signal processors (DSPs), and/or application-specific integrated circuits (ASICs). To store information, for example, the controller 122 can include one or more storage elements, such as volatile memory, non-volatile memory, read-only memory (ROM), and/or random access memory (RAM). The stored information can include pumping programs, patient information, and/or other executable programs. The controller 122 can further include a manual input device (e.g., a keyboard, a touch screen, etc.) and/or an automated input device (e.g., a computer, a data storage device, servers, network, etc.). In still other embodiments, the controller 122 may include different features and/or have a different arrangement for controlling the flow of fluid into and out of the fluid source 118.

The delivery capsule 108 includes the first housing 112 and the second housing 114, which can each contain at least a portion of the device 102 in the containment configuration. The second housing 114 can have an opening 134 at its distal end portion through which the guidewire 124 can be threaded to allow for guidewire delivery to the target site. As shown in FIG. 6, the distal end portion of the second housing 114 may also have an atraumatic shape (e.g., a partially spherical shape, a frusto-conical shape, blunt configuration, rounded configuration, etc.) to facilitate atraumatic delivery of the delivery capsule 108 to the target site. In certain embodiments, the delivery capsule 108 includes a proximal cap 136 that extends proximally from the first housing 112 to seal or enclose the device 102 within the delivery capsule 108. In some embodiments, the proximal cap 136 is omitted and the proximal portion of the delivery capsule 108 is left open. In these embodiments, the proximal end portion of the delivery capsule 108 (e.g., the proximal end portion of the first housing 112) can include rounded proximal edges, a tapered portion, and/or a soft or pliable material (e.g., a polymer) positioned at the proximal end to facilitate atraumatic retraction of the delivery capsule 108 through the body. The first housing 112, the second housing 114, and/or the proximal cap 136 can be made of metal (e.g., stainless steel), polymers, plastic, composites, combinations thereof, and/or other materials capable of holding the device 102 during trans-septal and/or trans-apical delivery to the target site (e.g., the mitral valve).

As discussed above, the first housing 112 slides or otherwise moves relative to the second housing 114 in a telescoping manner to release a portion of the device 102 from the delivery capsule 108 and, optionally, resheathe the device 102 after partial deployment. In certain embodiments, the first and second housings 112 and 114 are hydraulically actuated via the handle assembly 110 and/or the fluid assembly 116. In hydraulically-actuated embodiments, the delivery capsule 108 includes a first fluid chamber configured to receive a flowable material from the fluid assembly 116 to move the first housing 112 relative to the second housing 114. The delivery capsule 108 can further include a second fluid chamber configured to receive a flowable material from the fluid assembly 116 to move the first and second housing 112 and 114 as a unit. During the first deployment stage, a clinician can use the first actuator 130 and/or other suitable control means to deliver fluid (e.g., water or saline) from the fluid source 118 to the first fluid chamber to move the first housing 112 in a distal direction over the second housing 114 to release a first portion of the device 102 from the delivery capsule 108. During the second deployment stage, the clinician can use the second actuator 132 and/or other suitable control means to deliver fluid from the fluid source 118 to the second fluid chamber such that the first and second housings 112 and 114 move together in the distal direction to release a second portion of the device 102 from the delivery capsule 108 until the device 102 is partially or fully unsheathed from the delivery capsule 108. The first actuator 130, the second actuator 132, and/or other features can also be used to remove fluid from the first and second fluid chambers to allow for resheathing of the device 102 or close the delivery capsule 108. In other embodiments, the first housing 112 and/or the second housing 114 can be moved distally and proximally for unsheathing and resheathing using mechanical means, such as wire tethers.

The ability of the first housing 112 to move relative to the second housing 114 in a telescoping manner to deploy the device 102 results in a delivery capsule 108 that is relatively compact in length (e.g., a length of 40 mm or less) and that requires relatively short overall longitudinal translation (e.g., 50 mm or less, 40 mm or less, etc.) to deploy the device 102. For example, the telescoping delivery capsule 108 inherently requires less longitudinal translation for deployment than if the delivery capsule 108 were defined by a single housing that moves distally or proximally to deploy the device 102, or two separate housings that move in opposite directions to deploy the device 102. This shorter longitudinal translation in solely the distal direction facilitates trans-septal delivery of the device 102 to a native mitral valve of a human patient. For a typical patient with functional mitral valve regurgitation ("FMR"), the distance across the left atrium is estimated to be about 50 mm and the length of the left ventricle is estimated to be about 70 mm. During trans-septal delivery of the device 102, the delivery capsule 108 can extend through the opening in the septal wall between the right and left atria and be positioned in or proximate to the mitral valve annulus by bending the distal portion 106a of the catheter body 106 from the left atrium into the mitral valve. The compact size of the delivery capsule 108 facilitates positioning the delivery capsule 108 into the left atrium and making the turn into the native mitral valve without being limited by the anatomical sizing of the right atrium. During device deployment, the telescoping delivery capsule 108 does not require any portion of the delivery capsule 108 to extend in a proximal direction into the left atrium of the heart, and the telescoping arrangement of the first and second housings 112 and 114 results in a short overall longitudinal translation (relative to the axial length of the device 102) of the housings 112, 114 into the left ventricle of the heart, much less than typical length of the left ventricle. Thus, the telescoping delivery capsule 108 avoids the typical constraints associated with trans-septal delivery and the associated anatomy proximate to the target site in the mitral valve.

Figure 7A:
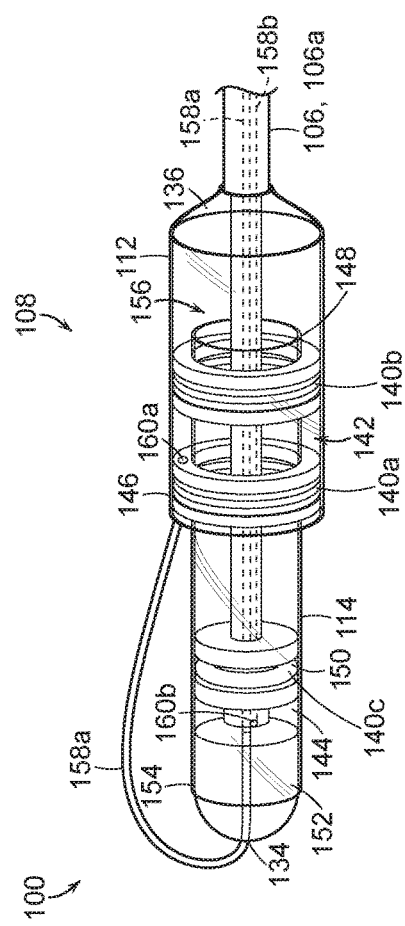
FIG. 7A is an enlarged side isometric view of a distal portion of the delivery system of FIG. 6 configured in accordance with embodiments of the present technology.
Figure 7B:
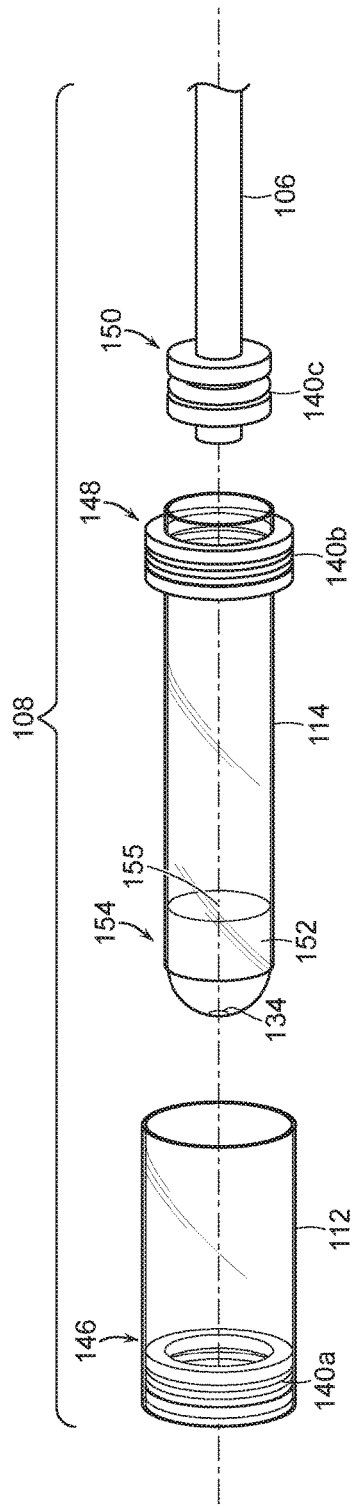
FIG. 7B is an exploded view of a delivery capsule of the delivery system of FIG. 7A.

FIG. 7A is an enlarged side isometric view of the delivery capsule 108 of the delivery system 100 of FIG. 6 configured in accordance with embodiments of the present technology, and FIG. 7B is an exploded view of the delivery capsule 108 of FIG. 7A. The delivery capsule 108 includes the first housing 112 partially overlapping and movable relative to the second housing 114. The first and second housings 112 and 114 are shown as transparent for illustrative purposes in FIGS. 7A and 7B; however, the first and second housings 112 and 114 may be made from opaque materials, including metals, polymers, plastics, composites, and/or combinations thereof. In certain embodiments, the first housing 112 has a length of about 20-30 mm, the second housing has a length of about 20-30 mm, and the first and second housings 112 and 114 overlap in such a manner that the overall longitudinal length of the delivery capsule 108 is 50 mm or less (e.g., 45 mm, 40 mm, etc.) when in the initial containment or delivery state. In various embodiments, such as when the delivery capsule 108 is configured to retain a prosthetic mitral valve device, the first housing 112 may have an outer diameter of about 11.58 mm and an inner diameter of about 10.82 mm, and the second housing 114 may have an outer diameter of about 9.53 mm and an inner diameter of about 9.02 mm. In other embodiments, the first and second housings 112 and 114 have different dimensions suitable for storing and delivering the medical device contained therein.

The delivery capsule 108 further includes a plurality of sealing members (identified individually as first through third sealing members 140a-c, respectively; referred to collectively as "sealing members 140"), such as sealing sleeves and/or O-rings, that can fluidically seal portions of the delivery capsule to define a first fluid chamber 142, a second fluid chamber 144, and/or portions thereof. The sealing members 140 can be sleeves, O-rings, O-rings positioned within sleeves, and/or other sealing features that are fixedly attached to the first housing 112, the second housing 114, and/or other portions of the delivery capsule 108 via bonding, laser welding, and/or other mechanisms for securing the sealing members 140 in position on portions of the delivery capsule 108. In certain embodiments, for example, the first and second housings 112 and 114 can include sleeves or flanges formed in or on the surfaces of the housings 112, 114 (e.g., using 3D printing) and configured to receive O-rings and/or other sealing features. As shown in FIGS. 7A and 7B, the first sealing member 140a can be fixedly attached to the first housing 112, extend between an inner surface of a distal portion 146 of the first housing 112 and an outer surface of the second housing 114, and be slidable relative to the second housing 114. The second sealing member 140b can be fixedly attached to the second housing 114 and extend between an outer surface of a proximal portion 148 of the second housing and the inner surface of the first housing 112. Thus, the first fluid chamber 142 can be defined at a distal end by the first sealing member 140a, at a proximal end by the second sealing member 140b, and the portions of an inner surface of the first housing 112 and an outer surface of the second housing 114 that extend between the first and second sealing members 140a and 140b. During deployment, the first sealing member 140a slides distally along the outer surface of the second housing 114 as the first fluid chamber 142 is pressurized with fluid to move the first housing 112 in a distal direction over a portion of the second housing 114.

The second fluid chamber 144 is positioned within the second housing 114 and can be defined at a proximal end by the third sealing member 140c. As shown in FIG. 7A, for example, the delivery capsule 108 can further include a platform 150 that extends outwardly from the distal end portion of the elongated body 106 and/or other shaft extending into the delivery capsule 108, and the third sealing member 140c can extend from the platform 150 (e.g., from a surface on or a recess within the platform 150) to the inner surface of the second housing 114 to fluidically seal the second fluid chamber 144 at a proximal end from other portions of the delivery capsule 108. In other embodiments, the platform 150 can itself seal against the inner surface of the second housing 114 to fluidically seal the proximal end of the second fluid chamber 144. As further shown in FIG. 7A, the second fluid chamber 144 can be defined at its distal end by a distal end feature 152 (e.g., a nose cone) at a distal end portion 154 of the second housing 114, or by another portion of or within the second housing 114. Thus, the second fluid chamber 144 is defined at its proximal end by a distal-facing portion of the platform 150 and/or the third sealing member 140c, at a distal end by the distal end feature 152 or (if the end feature 152 is omitted) an interior distal end of the second housing 114, and the wall of the second housing 114 extending therebetween. During deployment, the third sealing member 140c, in conjunction with the platform 150, slides along the inner surface of the second housing 114 as the second fluid chamber 144 is pressurized with fluid to move the second housing 114, together with the first housing 112 as a unit, in a distal direction.

The platform 150 is fixed relative to the body 106 and/or another shaft extending therethrough, and can be configured to support a distal end portion of a prosthetic heart valve device (e.g., the device 102 of FIG. 6) during delivery. For example, the platform 150 can be configured to maintain the device in a substantially constant axial position relative to the native anatomy (e.g., the mitral valve) as the first and second housings 112 and 114 move in a distal direction to unsheathe the device. In other embodiments, the platform 150 can be pulled or otherwise moved in a proximal direction to further unsheathe the device. The platform 150 can be formed integrally with the body 106, or the body 106 and the platform 150 can be separate components made from metal, polymers, plastic, composites, combinations thereof, and/or other suitable materials.

The end feature 152 at the distal portion 154 of the second housing 114 can be a nose cone or other element that provides stability to the distal end of the delivery capsule 108 and/or defines an atraumatic tip to facilitate intraluminal delivery of the capsule 108. The end feature 152 can be integrally formed at the distal end portion 154 of the second housing 114, a separate component fixedly attached thereto, or defined by the distal end of the second housing 114. As shown in FIGS. 7A and 7B, the end feature 152 may include a channel 155 extending through its length and in communication with the distal opening 134 through which various components of the system 100 can extend beyond the distal end portion 154 of the delivery capsule 108. For example, the channel 155 can be used to carry a guidewire (e.g., the guidewire 124 of FIG. 6), a fluid lumen (discussed in further detail below), and/or a small shaft through which the guidewire, fluid lumen, and/or other system components can extend. O-rings, valves or other sealing members can be positioned in or around the channel 155 and the components extending therethrough to fluidically seal the second chamber 144 at the distal end from the external environment. In other embodiments, the end feature 152 can include multiple channels that extend to separate distal openings.

As further shown in FIG. 7A, the delivery capsule 108 also includes a separate compartment 156 fluidically sealed from the first and second fluid chambers 142 and 144 and configured to house a prosthetic heart valve device (e.g., the device 102 of FIG. 6) in the unexpanded, containment state. The compartment 156 can be defined at a distal end by a proximal-facing surface of the platform 150, at a proximal end by the proximal cap 136 or the proximal end of the first housing 112, and the interior walls of the first and second housings 112 and 114 extending therebetween. In embodiments where the proximal cap 136 is omitted, the proximal portion of the compartment 156 is open to the surrounding environment (e.g., the vasculature). In various embodiments, the platform 150 can include engagement features that releasably couple to portions of the device to facilitate loading of the device into the delivery capsule 108 and secure the device to the delivery capsule 108 until final deployment to allow for resheathing. During deployment, the compartment 156 is opened to the native environment at the target site by the distal movement of the first and second housings 112 and 114 relative to the platform 150, and, optionally, by proximal movement of the proximal cap 136.

The delivery system 100 further includes fluid lines (identified individually as a first fluid line 158a and a second fluid line 158b; referred to collectively as "fluid lines 158") in fluid communication with the first and second fluid chambers 142 and 144 via fluid ports (identified individually as a first fluid port 160a and a second fluid port 160b; referred to collectively as "fluid ports 160"). As shown in FIG. 7A, the first fluid line 158a is in fluid communication with the first fluid chamber 142 via the first fluid port 160a, and the second fluid line 158b is in fluid communication with the second fluid chamber 144 via the second fluid port 160b. The fluid ports 160 can include valves or other features with openings that regulate fluid to flow into and/or out of the fluid chambers 142, 144. The fluid lines 158 extend from the first and second fluid chambers 142 and 144 through the elongated catheter body 106, and are placed in fluid communication with a fluid source (e.g., the fluid assembly 116 of FIG. 6) at the proximal portion 106b (FIG. 6) of the catheter body 106 such that the fluid lines 158 can deliver fluid to and, optionally, remove fluid from the first and second fluid chambers 142 and 144 independently of each other. In several embodiments, the first and second fluid chambers 142 and 144 each have a dedicated fluid line 158 extending through or defined by portions of the catheter body 106, or a single fluid line may extend through the catheter body 106 and a valve assembly can be used to selectively deliver fluid to the first and second fluid chambers 142 and 144.

At the distal portion 106a of the catheter body 106, the first fluid line 158a extends in a distal direction from the main catheter body 106, through the distal end of the second housing 114 (e.g., through the channel 155 of the end feature 152 and through the opening 134), outside the second housing 114, and into the first fluid port 160a in fluid communication with the first fluid chamber 142. In the embodiment illustrated in FIG. 7A, the first fluid line 158a extends through the first sealing member 140a and the first fluid port 160a is positioned on a proximal-facing surface of the first sealing member 140a in fluid communication with the first fluid chamber 142. In other embodiments, the first fluid line 158a can extend through the wall of the first housing 112 and/or another portion of the delivery capsule 108 to fluidly communicate with the first fluid chamber 142. The portion of the first fluid line 158a that extends beyond the distal end of the main catheter body 106 and outside of the second housing 114 can be an umbilical cord-type tube or lumen. Although FIG. 7A illustrates the tube spaced apart from the outer surface of the second housing 114, the fluid lumen can run tightly along the distal end feature 152 and the outer surface of the second housing 114. In other embodiments, the distal portion of the first fluid line 158a can be a corrugated tube that coils or otherwise retracts when it is not filled with fluid, and/or another type of tube or structure configured to transport fluid to the first fluid chamber 142.

As further shown in FIG. 7A, the second fluid line 158b can terminate at the second fluid port 160b positioned at the distal end of the main catheter body 106 to place the second fluid port 160b in fluid communication with the second fluid chamber 144. In other embodiments, the second fluid line 158b can terminate at a distal-facing surface of the platform 150 in fluid communication with the second fluid chamber 144, or the second fluid line 158b may extend in a distal direction beyond the distal end of the main catheter body 106 into the second fluid chamber 144. In further embodiments, the distal portion of the second fluid line 158b includes a tube (e.g., a corrugated tube, an umbilical cord-type lumen, etc.) that extends beyond the distal end of the main catheter body 106, through the distal end of the second housing 114, and loops back into fluid communication with the second fluid chamber 144 via a fluid port in the wall of the second housing 112 and/or another portion of the delivery capsule 108 in fluid communication with the second fluid chamber 144.

Figure 8A:
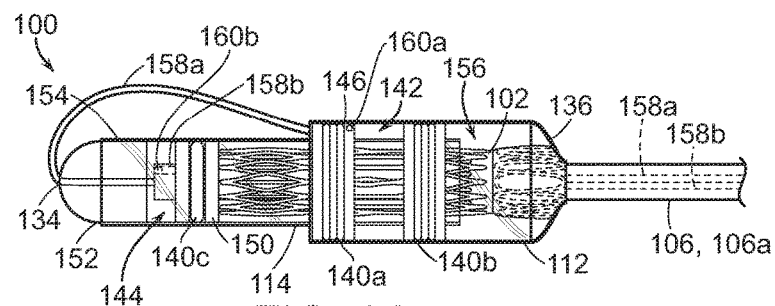

FIGS. 8A-8D are a series of illustrations showing the distal portion of the delivery system 100 of FIGS. 6-7B deploying and resheathing the device 102 via hydraulic actuation provided by filling and draining of the first and second fluid chambers 142 and 144. Although the following description is specific to deployment of prosthetic heart valve devices at a native mitral valve, the delivery capsule 108 can be used to deploy prosthetic valves, implants, and/or other medical devices in other portions of the body that may benefit from the short overall longitudinal translation and compact sizing provided by the telescoping delivery capsule 108. FIG. 8A illustrates the delivery capsule 108 in the initial delivery state with the device 102 constrained within the compartment 156 to allow for trans-luminal delivery of the device 102 to the target site. For a trans-septal approach to the native mitral valve, a clinician accesses the mitral valve from the venous system (e.g., via the transfemoral vein), navigates the delivery capsule 108 through the inferior vena cava into the right atrium, and passes the delivery capsule 108 through an aperture formed in the atrial septal wall into the left atrium. From the septal aperture, the clinician steers the distal portion of the delivery capsule 108 from its initial orientation, directed generally transverse to the inlet of the native mitral valve into axial alignment with the native mitral valve (e.g., a 90° turn) such that the distal portion of the delivery capsule 108 can pass through the native mitral annulus partially into the left ventricle. The compact axial length of the delivery capsule 108 (e.g., less than 50 mm) facilitates this turn from the septal wall into the native mitral valve within the anatomical constraints of the left atrium, which typically has a width of about 50 mm. Once the delivery capsule 108 is positioned at the desired site relative to the native mitral valve, the clinician can begin deployment of the device 102.

Figure 8B:
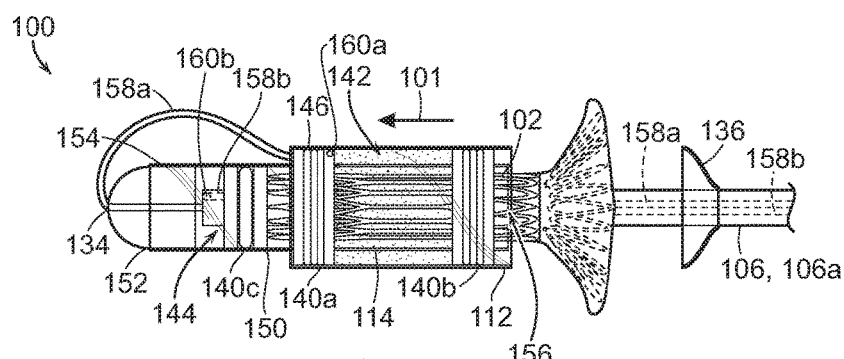

FIG. 8B illustrates the delivery capsule 108 during the first deployment stage during which the first fluid line 158a delivers fluid from the fluid assembly 116 (FIG. 6) to the first fluid chamber 142 via the first fluid port 160a. As fluid is added to the first fluid chamber 142, the increase in pressure within the first fluid chamber 142 causes the first sealing member 140a and the first housing 112 attached thereto to slide in a distal direction along the outer surface of the second housing 114 (as indicated by arrow 101). In certain embodiments, for example, the first sealing member 140a can be configured to move relative to the second housing 114 when the pressure within the first fluid chamber 142 exceeds a predetermined threshold, such as 4 atm to 8 atm. The total travel length of the first housing 112 in the distal direction during this first deployment stage can be at least 20 mm. In other embodiments, the first housing 112 may move smaller or greater distances depending on the size of the delivery capsule 108 and/or the device 102 positioned therein. The distal movement of the first housing 112 unsheathes a first portion of the device 102, such as a brim or atrial portion, allowing it to expand against surrounding native tissue and/or provide visualization for proper seating within the native valve. When the delivery capsule 108 includes a proximal cap, such as the proximal cap 136 shown in FIGS. 8A and 8B (not shown in FIGS. 8C and 8D for illustrative purposes), the distal movement of the first housing 112 separates the first housing 112 from the proximal cap 136 to expose the device 102. In other embodiments, the proximal cap 136 can be pulled in a proximal direction away from the first housing 112 before or during the first deployment stage.

Figure 8C:
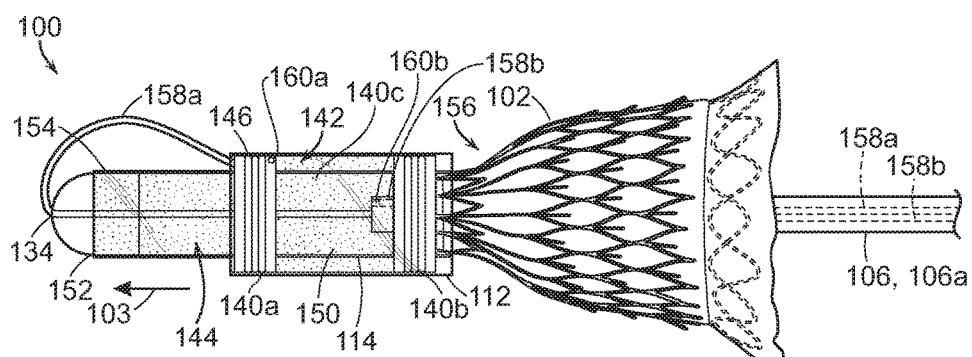

FIG. 8C illustrates the delivery capsule 108 during the second deployment stage during which the second fluid line 158b delivers fluid from the fluid assembly 116 (FIG. 6) to the second fluid chamber 144 via the second fluid port 160b. When the pressure within the second fluid chamber 144 exceeds a threshold level (e.g., 4-8 atm), the second housing 114 moves in a distal direction (as indicated by arrow 103) relative to the platform 150 and the associated third sealing member 140c as more fluid enters the second fluid chamber 144. Because the first fluid chamber 142 and the second fluid chamber 144 operate independently of each other, the first housing 112 moves with the second housing 114 as fluid fills or drains from the second fluid chamber 144. This distal movement of the second housing 114 partially or fully unsheathes the device 102 from the delivery capsule 108, while maintaining the brim or atrial portion of the device 102 at substantially the same axial position relative to the native annulus. In certain embodiments, the second housing 114 can translate 20-30 mm in the distal direction depending upon the length of the device 102. In other embodiments, filling the second fluid chamber 144 pushes platform 150 in proximal direction such that the platform 150 slides proximally along the inner surface of second housing 114 to deploy the remainder of the device 102. In this embodiment, the device 102 does not maintain its axial position during deployment. During the deployment procedure, the first and second deployment stages can be performed in separate and distinct time intervals as illustrated in FIGS. 8B and 8C to allow for dual-stage deployment of the device 102. In other embodiments, however, the first and second deployment stages can be simultaneous or at least partially overlapping such that the first and second fluid chambers 142 and 144 receive fluid at the same time.

In various embodiments, the delivery capsule 108 can also be configured to partially or fully resheathe the prosthetic heart valve device after partial deployment from the delivery capsule 108. FIG. 8D, for example, illustrates the delivery capsule 108 during a resheathing stage in which the delivery capsule 108 is driven back towards the delivery state by evacuating fluid from the first fluid chamber 142 via the first fluid line 158a and applying a proximally directed force on the first housing 112. For example, as shown in FIG. 8D, the first housing 112 may be operably coupled to a biasing device 137 (e.g., a spring) housed in the handle assembly 110 via a tether 135 and/or other coupling member that extends through the catheter body 106. The biasing device 137 can act on the first housing 112 (e.g., via the tether 135) to drive the first housing 112 in the proximal direction when fluid is removed from the first fluid chamber 142. In some embodiments, the biasing device 137 is omitted and the tether 135 itself can be manipulated at the handle assembly 110 (e.g., via an actuator) to retract the tether 135 in the proximal direction and draw the first housing 112 proximally. In various embodiments, the biasing device 137 can be positioned within the catheter body 106 (e.g., at the distal portion 106a of the catheter body 106) and/or associated with the delivery capsule 108 (e.g., as described in further detail below with respect to FIG. 9B) such that the biasing device 137 drives the first housing 112 proximally upon fluid removal. With the fluid evacuated from the first fluid chamber 142, the first sealing member 140a is allowed to slide in a proximal direction (as indicated by arrow 105) over the outer surface of the second housing 114 and move the first housing 112 back over at least a portion of the device 102 to place the resheathed portion of the device 102 back into the constrained, delivery state. For example, the first sealing member 140a can move in the proximal direction a desired distance and/or until the first sealing member 140a contacts the second sealing member 140b (e.g., about 20 mm). In some embodiments, resheathing can be initiated by removing fluid from the second fluid chamber 144, or removing the fluid from both the first and second fluid chambers 142 and 144 to allow the first housing 112 and/or second housing 114 to move back over the device 102. Similar to the first housing 112, the second housing 114 can be operably coupled to a mechanism that drives the second housing 114 in a proximal direction when fluid is evacuated from the second chamber 144, such as a tether, spring, and/or other biasing device. In some embodiments, a vacuum can be applied to the first fluid chamber 142 and/or the second fluid chamber 144 after the fluid has been evacuated from the chambers 142, 144 to facilitate moving the first housing 112 and/or the second housing 114 in the proximal direction. This resheathing ability allows the clinician to reposition the prosthetic heart valve device, in vivo, for redeployment within the mitral valve MV or remove the prosthetic heart valve device from the patient after partial deployment. Once the device 102 is fully deployed at the desired location, the first and second housings 112 and 114 can be drawn in a proximal direction through the deployed device 102, and the elongated catheter body 106 can be pulled proximally along the access path (e.g., through the aperture in the septal wall into the vasculature) for removal from the patient. After removing the catheter 104 (FIG. 6), the catheter 104 and the delivery capsule 108 can be discarded, or one or both components can be cleaned and used to deliver additional prosthetic devices.

The telescoping delivery capsule 108 and the delivery system 100 described above with respect to FIGS. 6-8D facilitate delivery via the trans-septal delivery approach due to the capsule's compact length, which can accommodate the turn from the aperture in the atrial septal wall into the native mitral valve necessary to position the device 102 in the native mitral valve without contacting the left atrial wall. In addition, the telescoping deployment provided by the first and second housings 112 and 114 results in short overall axial displacement of the delivery capsule 108 (relative to the length of the device 102) into the left ventricle during device deployment, and is thereby expected to avoid contact with portions of the left ventricle wall during deployment. By avoiding contact with the walls of the left ventricle and left atrium, the delivery system 100 also reduces the likelihood of arrhythmia during valve deployment. The hydraulic-actuation of the delivery capsule 108 provides controlled movement of the first and second housings 112 and 114 as the device 102 expands during unsheathing, and in certain embodiments allows the clinician to selectively suspend distal movement of the housings 112, 114 during any point of the deployment process to allow for repositioning and/or visualization. Further, the delivery capsule 108 may also be configured to at least substantially inhibit axial translation of the device 102 during deployment and resheathing (e.g., as shown in FIGS. 8A-8B) to facilitate accurate delivery to the target site.

In other embodiments, the telescoping delivery capsule 108 can operate in the opposite manner with respect to the distal portion 106a of the catheter body 106 such that the telescoping housings 112, 114 are configured to retract in a proximal direction to deploy the device 102 from the delivery capsule 108 and move in a distal direction to resheathe the device 102. Such an embodiment would be suitable to deliver the device 102 to the mitral valve from the left ventricle using a trans-apical approach (e.g., via an opening formed in the apical portion of the left ventricle). For example, the hydraulic actuation mechanism can move the first and second housings 112 and 114 in a proximal direction in a telescoping manner toward the distal portion 106a of the catheter body 106 to unsheathe the device 102. Once the device 102 is fully deployed within the mitral valve, the retracted delivery capsule 108 (with the first housing 112 at least partially overlapping the second housing 114) can be pulled in a proximal direction through the left ventricle and the apical aperture to remove the delivery system 100.

FIG. 9A is a side isometric view of a distal portion of a delivery system 200a configured in accordance with embodiments of the present technology. The delivery system 200a includes various features at least generally similar to the features of the delivery system 100 described above with reference to FIGS. 6-8D. For example, the delivery system 200a includes two telescoping housings 112, 114 that are hydraulically driven distally and proximally between a delivery state and a deployment state by moving fluid to and/or from the first fluid chamber 142 and the second fluid chamber 144. The delivery system 200a further includes a third or proximal fluid chamber 143 positioned in the annular space between the first and second housings 112 and 114. As shown in FIG. 9A, the delivery capsule 108 includes the first sliding sealing member 140a fixedly attached to the distal portion of the first housing 112, the internal second sealing member 140b fixedly attached to the second housing 114 between the first and second housings 112 and 114, and a proximal or fourth sliding sealing member 140d fixedly attached to the proximal portion of the first housing 112. Accordingly, the first fluid chamber 142 is between the distal-most or first sealing member 140a and the internal second sealing member 140b, and the third fluid chamber 143 is between the second sealing member 140b and the proximal sealing member 140d. The third fluid chamber 143 can be placed in fluid communication with a third fluid line 158c via a tube or other fluid-carrying features that extend outside of the second housing 114 and through the wall of the first housing 112 via a third fluid port 260c into fluid communication with the third fluid chamber 143 (e.g., similar to the distal portion of the first fluid line 158a). In other embodiments, the first fluid chamber 142 and/or the third fluid chamber 143 can be placed in fluid communication with the corresponding third fluid line 158c using other suitable means, such as fluid channels within the body of the delivery capsule 108.

During device deployment, the first fluid chamber 142 is pressurized with fluid, thereby causing the first sealing member 140a and the first housing 112 to slide distally until the proximal sealing member 140d comes into contact with the internal second sealing member 140b (e.g., about 20 mm). This unsheathes at least a portion of the device 102 from the delivery capsule 108. Further unsheathing can be performed by pressurizing the second fluid chamber 144 with fluid to hydraulically move the telescoped first and second housings 112 and 114 together in the distal direction to partially or completely unsheathe the device 102. In other embodiments, the telescoped first and second housings 112 and 114 are moved together in the distal direction using mechanical means. To retract the first housing 112, the first fluid chamber 142 is evacuated of fluid and the third fluid chamber 143 is pressurized with fluid via the third fluid line 158c. This causes the proximal sealing member 140d and the first housing 112 to slide proximally, e.g., until the first sealing member 140a stops against the internal second sealing member 140b. Accordingly, the supplemental third fluid chamber 143 can be used to facilitate resheathing of the device 102 and/or retraction of the delivery capsule 108 back to its delivery state. In some embodiments, the delivery capsule 108 can include additional fluid chambers that further facilitate device deployment and recapture, and/or the fluid chambers can be defined by different portions of the delivery capsule 108, while still being configured to hydraulically drive the first and second housings 112 and 114 distally and/or proximally relative to each other.

Figure 9B:
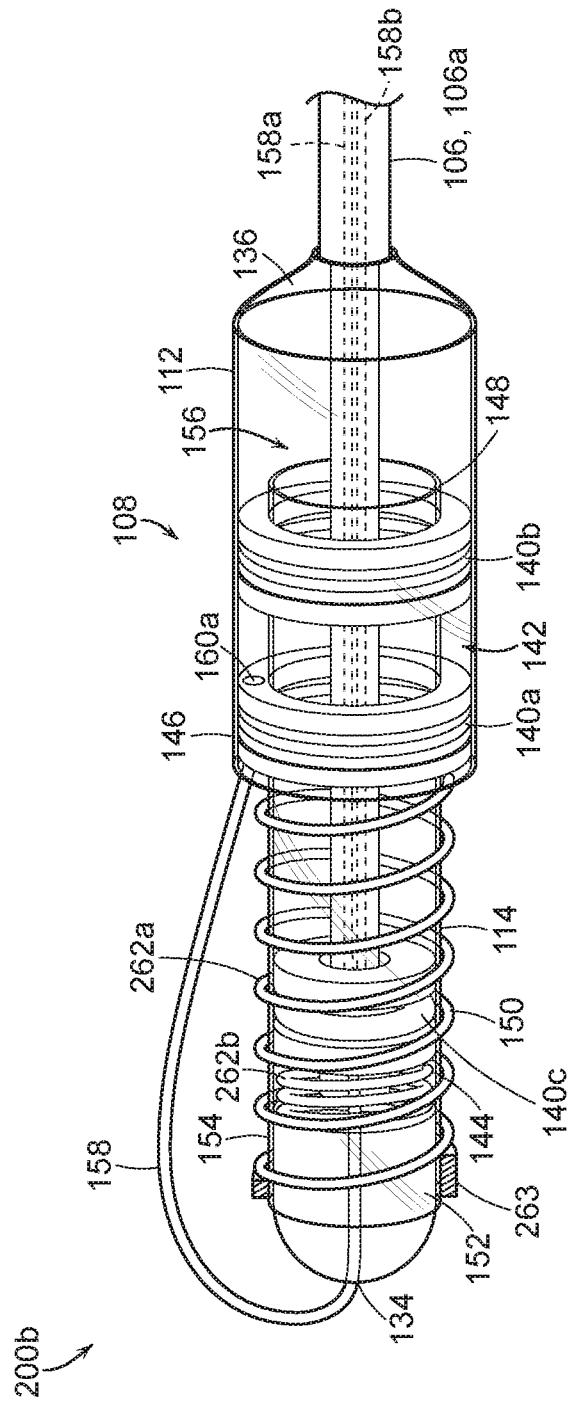
FIG. 9B is a side isometric view of a distal portion of a delivery system configured in accordance with embodiments of the present technology.

FIG. 9B is a side isometric view of a distal portion of a delivery system 200b in a delivery state configured in accordance with some embodiments of the present technology. The delivery system 200b includes various features at least generally similar to the features of the delivery system 100 described above with reference to FIGS. 6-8D. For example, the delivery system 200b includes two telescoping housings 112, 114 that are hydraulically driven distally and proximally between a delivery state and a deployment state by moving fluid to and from the first fluid chamber 142 and the second fluid chamber 144. The delivery system 200b further includes at least one biasing device (identified individually as a first biasing device 262a and a second biasing device 262b; referred to collectively as "biasing devices 262") that urges the first housing 112 and/or the second housing 114 toward the delivery state in the absence of fluid within the first and second fluid chambers 142 and 144. The biasing devices 262 can be springs (e.g., as shown in FIG. 9B) or other components that apply force on the housings 112, 114 when compressed or extended during device deployment.

As illustrated in FIG. 9B, the first biasing device 262a extends around a portion of the second housing 114 and acts on the distal end portion 146 of the first housing 112 when the first housing 112 moves toward the deployment state. An end stop component 263 or other feature can secure the distal end of the first biasing device 262a in place on the second housing 114. The first biasing device 262a compresses as the first housing 112 moves in the distal direction toward the deployment state, thereby applying a force on the first housing 112 in the proximal direction. In certain embodiments, the first biasing device 262a applies a constant proximally-directed force on the first housing 112 when the delivery capsule 108 is in the delivery state, and that force increases as the first housing 112 moves in the distal direction. In other embodiments, the first biasing device 262a is in a neutral state when the delivery capsule 108 is in the delivery state, and then applies a proximally-directed force to the first housing 112 as the first biasing device 262a compresses. This proximally-directed force may not be great enough to urge the first housing 112 closed when fluid is in the first fluid chamber 142, but after fluid removal from the first fluid chamber 142, the first biasing device 262a can push the first housing 112 in a proximal direction to resheathe a prosthetic device (e.g., the device 102 of FIGS. 6 and 8A-8D) positioned within the delivery capsule 108 and/or close the delivery capsule 108 for removal from the patient's body.

As further shown in FIG. 9B, the second biasing device 262b is positioned within the second housing 114 (e.g., within the second fluid chamber 144) such that it acts on the second housing 114 when the second housing 114 moves toward the deployment state. The second biasing device 262b can be coupled to the platform 150 at a proximal end of the second biasing device 262b, and to a distal portion of the second housing 114 or components therein (e.g., the distal end feature 152) at a distal end of the second biasing device 262b. When the second fluid chamber 144 fills with fluid and drives the distal end of the second housing 114 apart from the platform 150, the second biasing device 262b expands, thereby applying force on the first housing 112 and the platform 150 to pull the two components closer together. In certain embodiments, the second biasing device 262b applies a continual proximally-directed force on the second housing 114 when the delivery capsule 108 is in the delivery state, and that force increases as the second housing 114 moves in the distal direction. In other embodiments, the second biasing device 262b is in a neutral state when the delivery capsule 108 is in the delivery state, and then applies a proximally-directed force to the second housing 114 as the second biasing device 262b expands. When fluid is in the second fluid chamber 144, the biasing force is not of a magnitude to urge the second housing 114 toward the delivery state. However, after draining fluid from the second fluid chamber 144, the second biasing device 262b can pull the second housing 114 in a proximal direction and/or pull the second housing 114 and the platform 150 closer together (depending on the force required to slide the platform 150 relative to the second housing 114) to resheathe a device and/or close the delivery capsule 108.

The biasing devices 262 can also limit or substantially prevent distal movement of the housings 112, 114 attributable to the forces produced by an expanding prosthetic heart valve device (e.g., the device 102 of FIGS. 8A-8D). For example, hydraulic actuation can move the first housing 112 and/or the second housing 114 to unsheathe a portion of a prosthetic heart valve device, allowing the device to expand outwardly. Meanwhile, the biasing devices 262 can urge the housings 112, 114 toward the delivery state to counteract the distally-directed expansion forces of the device on the delivery capsule 108, and thereby prevent axial jumping. One, two, or more biasing devices 262 can be incorporated in any of the delivery capsules disclosed herein to urge the telescoping housings toward the deployment state. In some embodiments, the biasing devices 262 can be positioned elsewhere with respect to the delivery capsule 108 and/or the delivery system 200b and operably coupled to the first housing 112 and/or the second housing 114 to bias the housings 112, 114 toward the delivery configuration. For example, the second biasing device 262b can be positioned in a proximal portion of the delivery capsule 108 and operably coupled to the second housing 114 via a tether or other connector such that the second biasing device 262b acts on the second housing 114. As another example, the first biasing device 262a and/or the second biasing device 262b can be positioned in portions of the catheter body 106 and/or a handle assembly (the handle assembly 110 of FIG. 6), and connected to the first and second housings 112 and 114 via tethers or other connectors extending through the catheter body 106.

FIGS. 10A and 10B are a partial cut-away isometric view and a cross-sectional view, respectively, of a distal portion of a delivery system 300 configured in accordance with some embodiments of the present technology. The delivery system 300 includes various features at least generally similar to the features of the delivery systems 100, 200a, 200b described above with reference to FIGS. 6-9. For example, the delivery system 300 includes a telescoping delivery capsule 308 having a first housing 312, a second housing 314 slidably disposed within a portion of the first housing 312, and two fluid chambers (identified individually as a first fluid chamber 342 and a second fluid chamber 344) defined at least in part by sealing members 340 (identified individually as first through third sealing members 340a-c, respectively). More specifically, the first fluid chamber 342 is defined by the annular space between the first and second sealing members 340a and 340b, and the second fluid chamber 344 is defined by the portion of the second housing 314 between a platform 350 (including the third sealing member 340c) and a distal end portion 352. The first and second fluid chambers 342 and 344 are placed in fluid communication with a fluid source (e.g., the fluid assembly 116 of FIG. 6) via dedicated fluid lines 358 (identified individually as a first fluid line 358a and a second fluid line 358b).

In the embodiment illustrated in FIGS. 10A and 10B, the second fluid line 158b is a tube or shaft that extends through an elongated catheter body (not shown; e.g., the catheter body 106 of FIGS. 6-9) and affixes to the platform 350 where it terminates at a second fluid port 360b to deliver fluid to and/or remove fluid from the second fluid chamber 344 (as indicated by arrows 309). The first fluid line 358a includes a tube or channel that extends through the length of the second fluid line 358b, projects in a distal direction beyond the second port 358b and the platform 350, and then extends distally into the second fluid chamber 344 where the first fluid line 358a connects to one or more lumens 370 defined by the annular space in the wall of the second housing 114. The lumen 370 extends through the wall of the second housing 314 to the first fluid port 360a, which allows fluid to be delivered to and/or removed from the first fluid chamber 342 (as indicated by arrows 307). The portion of the first fluid line 358a that extends between the second fluid line 358b and the lumen 370 can be a flexible tube or corrugated lumen bonded to or otherwise sealed to the inlet of the lumen 370. Such flexible tubes or corrugated lumens allow the first fluid line 358b to bend, flex, and extend to maintain the connection with the lumen 370 as the platform 350 and the second housing 314 move relative to each other when the second fluid chamber 344 is filled or drained. In other embodiments, the first fluid line 358a and the second fluid line 358b run alongside each other, rather than concentrically, within an elongated catheter body or defined by separate portions of the catheter body.

In operation, fluid is delivered to the first fluid chamber 342 via the first fluid line 358a, which causes the first housing 312 to move in a distal direction over the second housing 314 to unsheathe a portion of a prosthetic heart valve device (e.g., the device 102 of FIGS. 7A-8D). In a subsequent or simultaneous step, fluid is delivered to the second fluid chamber 344 via the second fluid line 358b, causing the second housing 314 to move in the distal direction to further unsheathe the prosthetic heart valve device. During an optional resheathing stage, fluid can be removed from the first fluid chamber 342 via the first fluid line 358a and, optionally, the first fluid chamber 342 can be pressurized to move the first housing 312 in a proximal direction back over the prosthetic heart valve device. Further resheathing can be performed by draining and, optionally, applying a vacuum to the second fluid chamber 344.

Figure 10C:
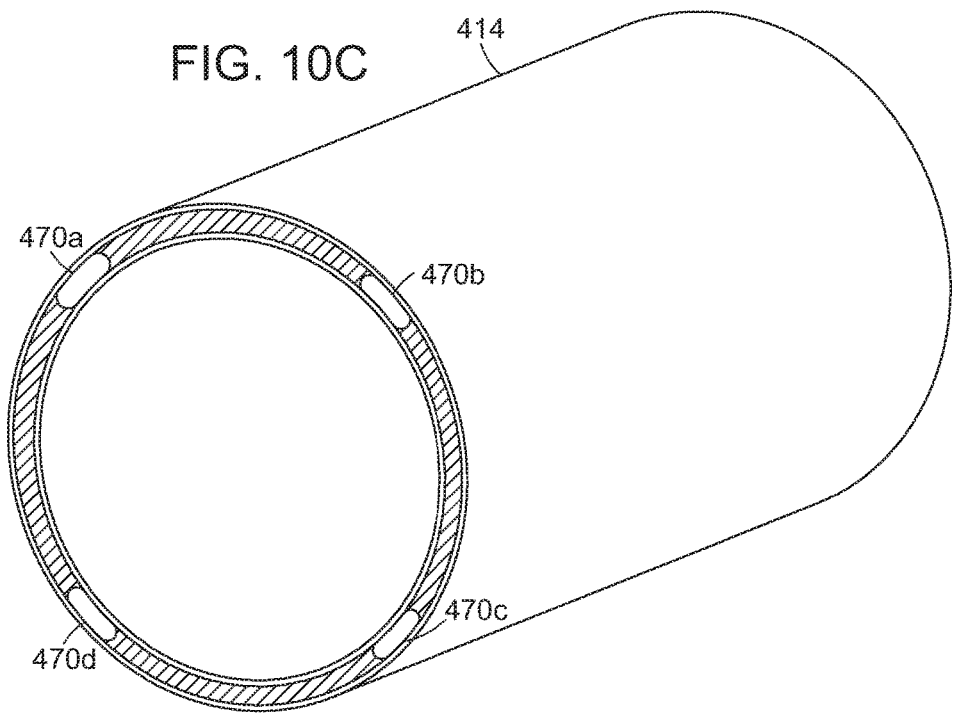
FIGS. 10C and 10D are isometric views of inner housing configurations for use with the delivery system of FIGS. 10A and 10B.
Figure 10D:
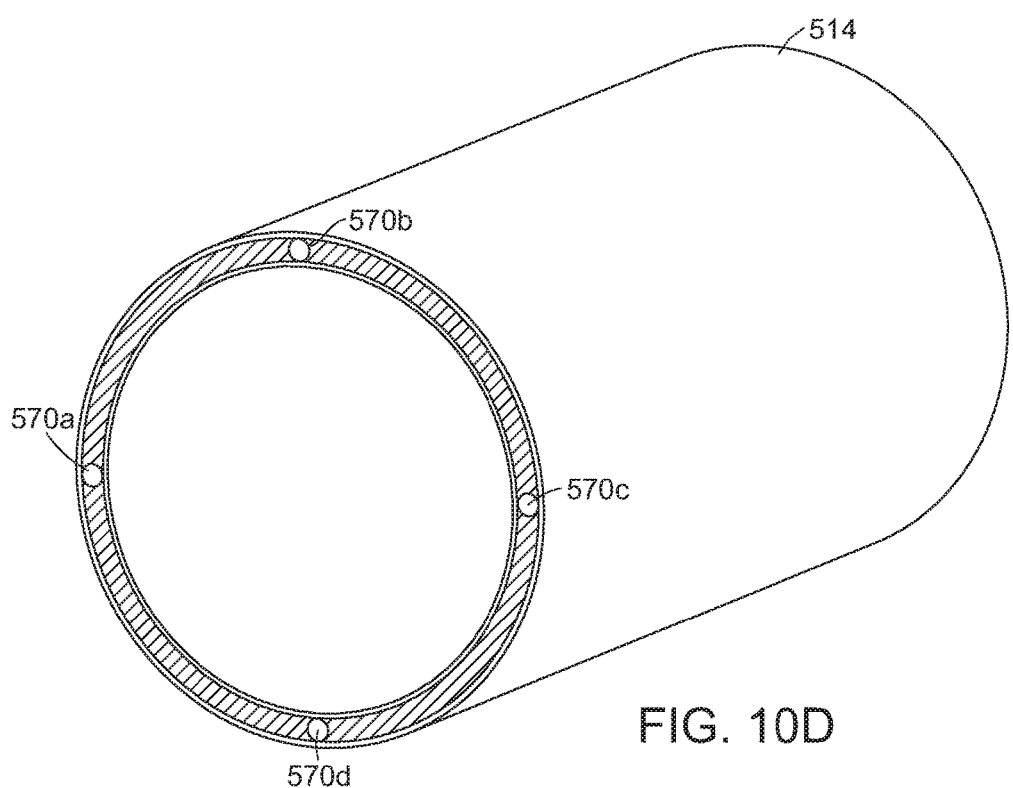

FIGS. 10C and 10D are cutaway isometric views of housing configurations for use with the delivery system 300 of FIGS. 10A and 10B. More specifically, FIGS. 10C and 10D illustrate different configurations of a second housing 414, 514 having lumens within the housing wall such that the second housing 414, 514 can define an end portion of a first fluid line (e.g., the first fluid line 358a of FIGS. 10A and 10B) in fluid communication with a first fluid chamber (e.g., the first fluid chamber 342 of FIGS. 10A and 10B). In some embodiments as illustrated in FIG. 10C, the second housing 414 includes four oblong or oval-shaped lumens (identified individually as first through fourth lumens 470*a-b*, respectively; referred to collectively as lumens 470) spaced equally about the circumference of the second housing 414 and extending through at least a portion of the wall of the second housing 414. In some embodiments as illustrated in FIG. 10D, the second housing 514 includes four circular lumens (identified individually as first through fourth lumens 570*a-b*, respectively; referred to collectively as lumens 570) spaced equally about the circumference of the second housing 514 and extending through at least a portion of the wall of the second housing 514. In some embodiments, each lumen 470, 570 has a first end coupled to a portion of the first fluid line (e.g., the first fluid line 358*a* of FIGS. 10A and 10B) extending from a proximal portion of a catheter body (e.g., the catheter bodies 106, 306 of FIGS. 6, 10A and 10B) via a flexible tube or other feature, and a second end that is placed in fluid communication with a first fluid chamber (e.g., the first fluid chamber 342 of FIGS. 10A and 10B) via individual fluid ports. In some embodiments, only one of the lumens 470, 570 is coupled to a portion of the first fluid line (e.g., the first fluid line 358*a* of FIGS. 10A and 10B) extending from a proximal portion of a catheter body (e.g., the catheter bodies 106, 306 of FIGS. 6, 10A and 10B) via a flexible tube or other feature, and the second housing 414, 514 includes additional internal lumens that connect the other lumens 470, 570 to each other such that the lumens 470, 570 can be placed in fluid communication with a first fluid chamber (e.g., the first fluid chamber 342 of FIGS. 10A and 10B) via individual fluid ports. In some embodiments, the second housing 414, 514 includes one, two, three, or more than four lumens 470, 570 spaced equidistance or at other desired locations around the circumference of the second housing 414, 514. In still further embodiments, the lumens 470, 570 may have different cross-sectional shapes suitable for carrying fluid. Any of the configurations of the second housings 314, 414, 514 described with reference to FIGS. 10A-10D can also replace the second housing 114 in the delivery systems 100, 200*a*, 200*b* described above with reference to FIGS. 6-9.

Figure 11A:
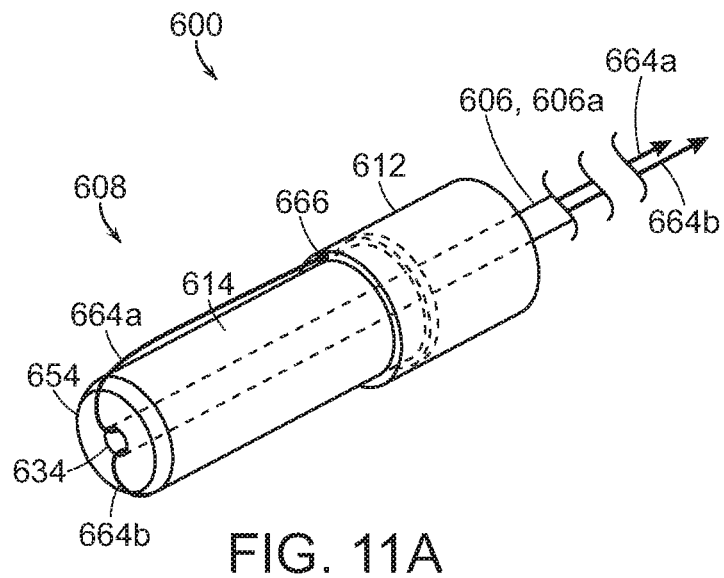
FIG. 11A is an isometric view of a distal portion of a delivery system configured in accordance with yet another embodiment of the present technology.
Figure 11B:
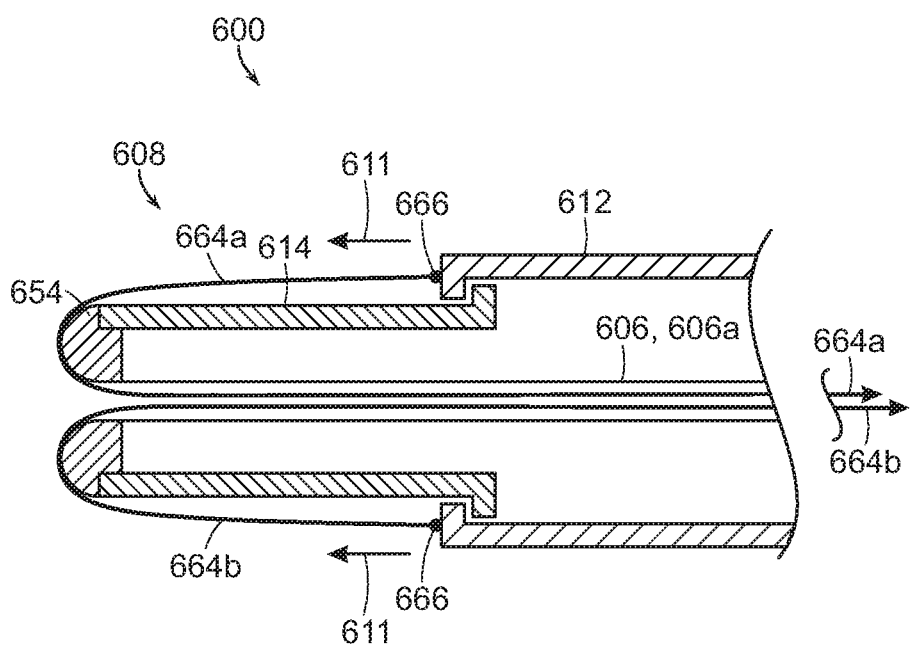
FIG. 11B is a cross-sectional view of the distal portion of the delivery system of FIG. 11B.

FIGS. 11A and 11B are isometric and cross-sectional views of a distal portion of a delivery system 600 configured in accordance with some embodiments of the present technology. The delivery system 600 includes various features at least generally similar to the features of the delivery systems 100, 200*a*, 200*b*, 300 described above with reference to FIGS. 6-10D. For example, the delivery system 600 includes an elongated catheter body 606 and a telescoping delivery capsule 608 at a distal end portion 606*a* of the catheter body 606. The delivery capsule 608 includes a first housing 612 and a second housing 614 slidably disposed within a portion of the first housing 612 such that, during deployment, the first housing 612 moves in a distal direction over the second housing 614 to release at least a portion of a prosthetic heart valve device (e.g., the device 102 of FIGS. 6 and 8A-8D) from the delivery capsule 608.

Rather than the hydraulically-actuated first and second housings described with reference to FIGS. 6-10D, the delivery capsule 608 of FIGS. 11A and 11B moves the first and second housings 612 and 614 using non-fluidic means. For example, the delivery system 600 includes a plurality of tether elements (identified individually as a first tether element 664*a* and a second tether element 664*b*; referred to collectively as "tether elements 664") coupled to a distal portion and/or other portion of the first housing 612 at corresponding attachment features 666 and configured to move the first housing 612 relative to the second housing 614. The tether elements 664 can be can be wires, sutures, cables, and/or other suitable structures for driving movement of the first housing 612, and the attachment features 666 can include adhesives, interlocking components, hooks, eyelets, and/or other suitable fasteners for joining one end portion of the tether elements 664 to the first housing 612. Although two tether elements 664 are shown in FIGS. 11A and 11B, the delivery system 600 can include a single tether element and/or more than two tether elements to drive movement of the first housing 612.

The tether elements 664 extend from the first housing 612 in a distal direction over a distal end portion 654 of the second housing 614 (e.g., a nose cone), into a distal opening 634 of the second housing 614, and in a proximal direction through the catheter body 606. At a proximal portion of the delivery system 600, proximal end portions of the tether elements 664 can be attached to actuators of a handle assembly (e.g., the handle assembly 110 of FIG. 6) and/or otherwise accessible to allow a clinician to pull or otherwise proximally retract the tether elements 664 (as indicated by the arrows associated with the proximal ends of the tether elements 664). During this proximal retraction of the tether elements 664, the distal end portion 654 of the second housing 614 serves as a pulley to change the direction of motion, and thereby move the first housing 612 in a distal direction (as indicated by arrows 611 of FIG. 11B). This causes the first housing 612 to slide over the second housing 614 such that at least a portion of the second housing 614 is telescoped within the first housing 612 and the prosthetic heart valve device is unsheathed from the first housing 612.

The remainder of the prosthetic heart valve device can be unsheathed from the delivery capsule 608 in a subsequent deployment step by moving the second housing 614 (together with the first housing 612) in a distal direction. For example, the second housing 614 can be driven in the distal direction using mechanical means (e.g., rods or pistons) to push the second housing 614 distally, or the second housing 614 can move via hydraulic means by moving fluid to one or more fluid chambers (e.g., similar to the fluid chambers described above with reference to FIGS. 6-10D). In other embodiments, a piston device and/or other feature can be used to push the prosthetic heart valve device in a proximal direction out from the second housing 614. Similar to the telescoping delivery capsules described above, the mechanically-activated delivery capsule 608 can have a compact size and a relatively short overall longitudinal translation to deploy the prosthetic heart valve device to facilitate transseptal delivery of the prosthetic heart valve device to the mitral valve. In other embodiments, the delivery capsule 608 can be used to facilitate the delivery of other types of devices to regions of the body that benefit from the short axial deployment paths provided by the telescoping housings 612, 614.

In various embodiments, the delivery capsule 608 can further be configured to allow for resheathing a partially deployed device and/or otherwise moving the delivery capsule 608 back toward its initial delivery state. A clinician pushes or otherwise moves the tether elements 664 in the distal direction (e.g., via an actuator on a proximally-positioned handle assembly), thereby moving the first housing 612 in a proximal direction. To accommodate such distal movement of the tether elements 664, each tether element 664 can be routed through an individual tube or channel that extends through the catheter body 606 and allows the clinician to both pull and push the tether elements 664, while inhibiting the tether elements 664 from buckling along the length of the catheter body 606 during proximal movement. In other embodiments, the tether elements 664 and/or portions thereof can be made from semi-rigid and/or rigid materials that avoid buckling when the tether elements 664 are not placed in tension.

Figure 12A:
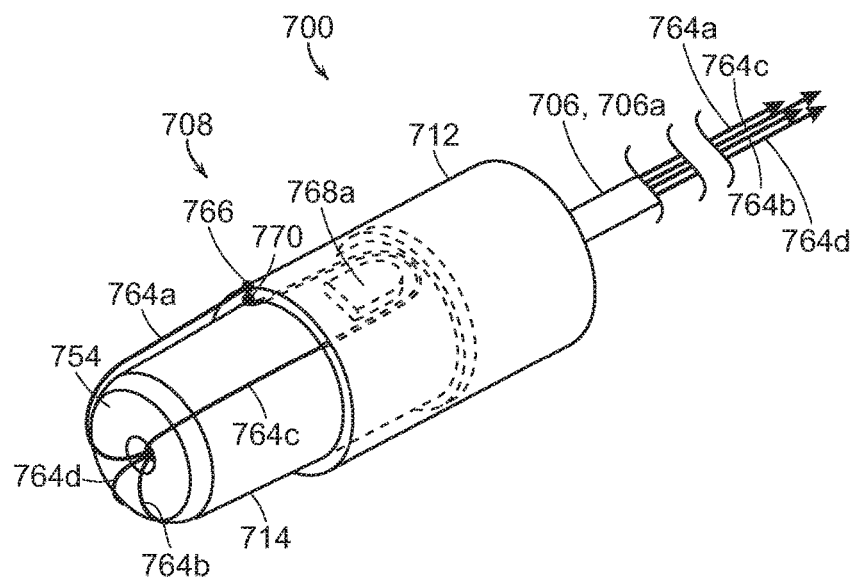
FIG. 12A is an isometric view of a distal portion of a delivery system configured in accordance with a still further embodiment of the present technology.
Figure 12B:
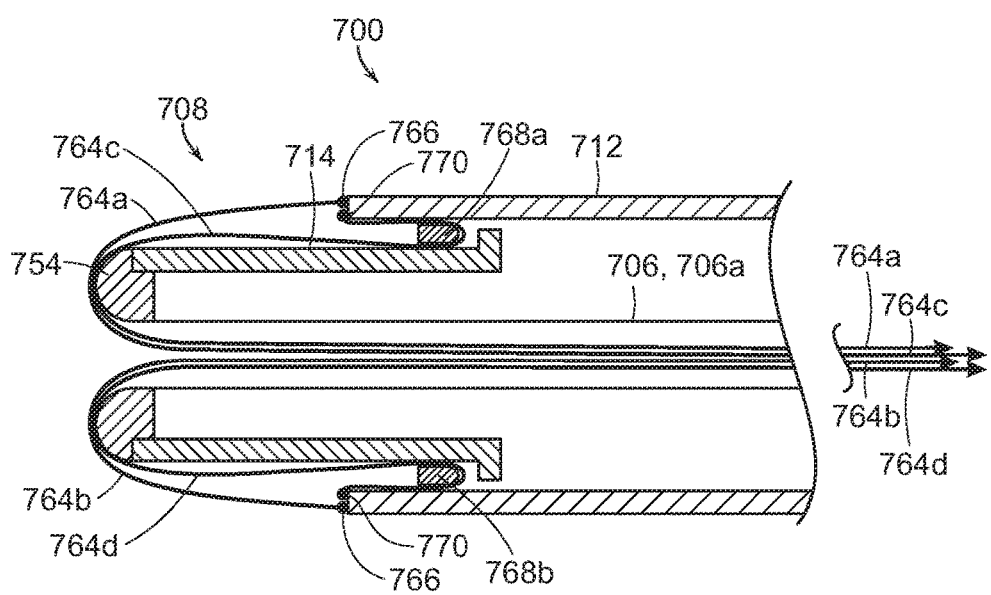
FIG. 12B is a cross-sectional view of the distal portion of the delivery system of FIG. 12B.

FIGS. 12A and 12B are isometric and cross-sectional views, respectively, of a distal portion of a delivery system 700 configured in accordance with some embodiments of the present technology. The delivery system 700 includes various features at least generally similar to the features of the mechanically-driven delivery system 600 described above with reference to FIGS. 11A and 11B. For example, the delivery system 700 includes an elongated catheter body 706, a delivery capsule 708 with telescoping first and second housings 712 and 714 at a distal end portion 706a of the catheter body 706, and a plurality of tether elements (identified individually as a first through fourth tether element 764a-764d, respectively; referred to collectively as "tether elements 764") coupled to portions of the first housing 712. The tether elements 764 mechanically drive the first housing 712 in both a distal direction to move the delivery capsule 708 toward an unsheathing or deployment state and a proximal direction to move the delivery capsule 708 back toward its initial delivery state (e.g., for resheathing the device). As described in further detail below, the delivery system 700 includes four tether elements 764—two dedicated unsheathing tether elements 764 that move the first housing 712 in the distal direction and two dedicated resheathing tether elements 764 that move the first housing 712 in the proximal direction. In other embodiments, however, the delivery system 700 can include a single tether element 764 or more than two tether elements 764 to initiate distal movement of the first housing 712. In further embodiments, the delivery system 700 can include a single tether element or more than two tether elements 764 to initiate proximal movement of the first housing 712.

The first and second tether elements 764a and 764b are configured to drive the first housing 712 in the distal direction to at least partially unsheathe a proximal heart valve device and/or other device stored within the delivery capsule 708. Similar to the tether elements 664 of FIGS. 11A and 11B, distal end portions of the first and second tether elements 764a and 764b are coupled to the first housing 712 at two corresponding attachment features 766, from which the first and second tether elements 764a and 764b extend in a distal direction over a distal end portion 754 of the second housing 714 (e.g., a nose cone), into a distal opening 734 of the second housing 714, and then in a proximal direction through the catheter body 706. At a proximal portion of the delivery system 700, a clinician can pull or otherwise proximally retract the first and second tether elements 764a and 764b (e.g., via actuators on the handle assembly 110 of FIG. 6) to move the first housing 712 in a distal direction over the second housing 714 and unsheathe at least a portion of the device from the first housing 712. The remainder of the device can be unsheathed from the delivery capsule 708 in a separate deployment step by moving the second housing 714 (together with the first housing 712) in a distal direction via mechanical or hydraulic actuation means and/or urging the device in a proximal direction out from the second housing 714 (e.g., via a piston device).

The third and fourth tether elements 764c and 764d are used to mechanically drive the first housing 712 in the proximal direction to at least partially resheathe the device and/or close the delivery capsule 708 for removal from the patient. Distal end portions of the third and fourth tether elements 764c and 764d are coupled to a distal end portion of the first housing 712 at two corresponding attachment features 770, such as adhesives, interlocking components, hooks, eyelets, and/or other suitable fasteners for joining one end portion of the tether elements 764 to the first housing 712. As shown in FIGS. 12A and 12B, the third and fourth tether elements 764c and 764d extend from the attachment features 770 in a proximal direction between the first and second housings 712 and 714 until they are routed around an arched feature (identified individually as a first arched feature 768a and a second arched feature 768b; referred to collectively as "arched features 768") of the second housing 714. The arched features 768 can be protrusions or channels projecting from the outer surface of the second housing 714 and/or in the wall of the second housing 714, and have a U-shaped or V-shaped surface that reverses the direction of the third and fourth tether elements 764c and 764d. In the illustrated embodiment, the second housing 714 includes two arched features 768 corresponding to the two tether elements 764c-d, but in other embodiments the second housing 714 can include a single arched feature 768 and/or more than two arched features 768 that are configured to reverse the direction of one or more tether elements 764. After reversing direction via the arched features 768, the third and fourth tether elements 764c and 764d extend in a distal direction over the distal end portion 754 of the second housing 714, into the distal opening 734, and then in a proximal direction through the catheter body 706. At the proximal portion of the delivery system 700, proximal end portions of the third and fourth tether elements 764c and 764d can be attached to actuators of a handle assembly (e.g., the handle assembly 110 of FIG. 6) and/or otherwise accessible to allow the clinician to pull or otherwise proximally retract the third and fourth tether elements 764c and 764d, which in turn moves the first housing 712 in the proximal direction. In this embodiment, the arched features 768 of the second housing 714 serve as pulleys to change the direction of motion of the third and fourth tether elements 764c and 764d, thereby moving the first housing 712 in the proximal direction when the third and fourth tether elements 764c and 764c are proximally retracted.

In operation, the clinician can at least partially unsheathe the device by proximally retracting the first and second tether elements 764a and 764b to move the first housing 712 in the distal direction toward the unsheathing state. The clinician can further unsheathe the device by moving the second housing 714 in the distal direction. If resheathing is desired to adjust position or remove the device from the patient, the clinician can proximally retract the third and fourth tether elements 764c and 764d to move the first housing 712 back over the device in the proximal direction to resheathe a portion of the device within the first housing 712. After full deployment of the device at the target site, proximal retraction of the third and fourth tether elements 764c and 764d can again be used to move the first housing 712 proximally such that the delivery capsule 708 is placed back into the delivery state for removal from the patient. Accordingly, the delivery system 700 uses proximal retraction of the tether elements 764 to mechanically drive the first housing 712 in both the distal and proximal directions. Similar to the telescoping delivery capsules described above, the delivery capsule 708 of FIGS. 12A and 12B provides deployment procedures that require only short overall longitudinal translation relative to the device size to facilitate trans-septal delivery of a prosthetic heart valve device to the mitral valve and/or deployment of medical devices to other target sites having constrained anatomical dimensions.

Selected Embodiments of Prosthetic Heart Valve Devices

The telescoping delivery systems 100, 200a, 200b, 300, 600 and 700 described above with reference to FIGS. 6-12B can be configured to deliver various prosthetic heart valve devices, such as prosthetic valve devices for replacement of the mitral valve and/or other valves (e.g., a bicuspid or tricuspid valve) in the heart of the patient. Examples of these prosthetic heart valve devices, system components, and associated methods are described in this section with reference to FIGS. 13A-26. Specific elements, substructures, advantages, uses, and/or other features of the embodiments described with reference to FIGS. 13A-26 can be suitably interchanged, substituted or otherwise configured with one another. Furthermore, suitable elements of the embodiments described with reference to FIGS. 13A-26 can be used as stand-alone and/or self-contained devices.

Figure 13A:
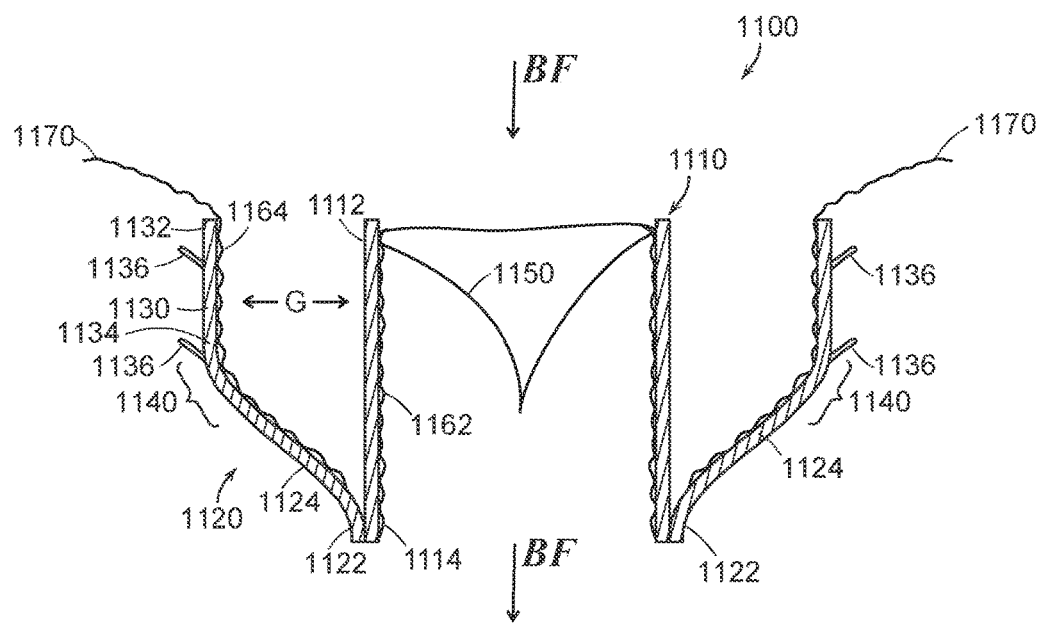
FIG. 13A is a cross-sectional side view and FIG. 13B is a top view schematically illustrating a prosthetic heart valve device in accordance with an embodiment of the present technology.
Figure 13B:
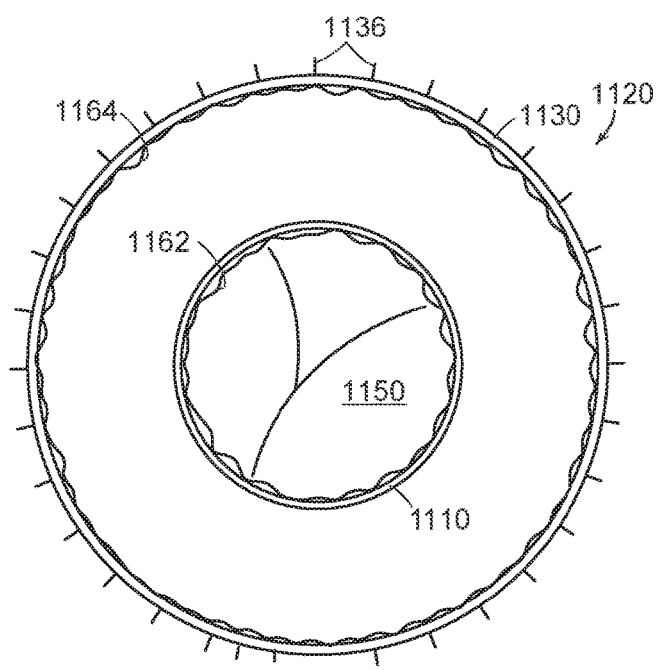

FIG. 13A is a side cross-sectional view and FIG. 13B is a top plan view of a prosthetic heart valve device ("device") 1100 in accordance with an embodiment of the present technology. The device 1100 includes a valve support 1110, an anchoring member 1120 attached to the valve support 1110, and a prosthetic valve assembly 1150 within the valve support 1110. Referring to FIG. 13A, the valve support 1110 has an inflow region 1112 and an outflow region 1114. The prosthetic valve assembly 1150 is arranged within the valve support 1110 to allow blood to flow from the inflow region 1112 through the outflow region 1114 (arrows BF), but prevent blood from flowing in a direction from the outflow region 1114 through the inflow region 1112.

In the embodiment shown in FIG. 13A, the anchoring member 1120 includes a base 1122 attached to the outflow region 1114 of the valve support 1110 and a plurality of arms 1124 projecting laterally outward from the base 1122. The anchoring member 1120 also includes a fixation structure 1130 extending from the arms 1124. The fixation structure 1130 can include a first portion 1132 and a second portion 1134. The first portion 1132 of the fixation structure 1130, for example, can be an upstream region of the fixation structure 1130 that, in a deployed configuration as shown in FIG. 13A, is spaced laterally outward apart from the inflow region 1112 of the valve support 1110 by a gap G. The second portion 1134 of the fixation structure 1130 can be a downstream-most portion of the fixation structure 1130. The fixation structure 1130 can be a cylindrical ring (e.g., straight cylinder or conical), and the outer surface of the fixation structure 1130 can define an annular engagement surface configured to press outwardly against a native annulus of a heart valve (e.g., a mitral valve). The fixation structure 1130 can further include a plurality of fixation elements 1136 that project radially outward and are inclined toward an upstream direction. The fixation elements 1136, for example, can be barbs, hooks, or other elements that are inclined only in the upstream direction (e.g., a direction extending away from the downstream portion of the device 1100).

Referring still to FIG. 13A, the anchoring member 1120 has a smooth bend 1140 between the arms 1124 and the fixation structure 1130. For example, the second portion 1134 of the fixation structure 1130 extends from the arms 1124 at the smooth bend 1140. The arms 1124 and the fixation structure 1130 can be formed integrally from a continuous strut or support element such that the smooth bend 1140 is a bent portion of the continuous strut. In other embodiments, the smooth bend 1140 can be a separate component with respect to either the arms 1124 or the fixation structure 1130. For example, the smooth bend 1140 can be attached to the arms 1124 and/or the fixation structure 1130 using a weld, adhesive or other technique that forms a smooth connection. The smooth bend 1140 is configured such that the device 1100 can be recaptured in a capsule or other container after the device 1100 has been at least partially deployed.

The device 1100 can further include a first sealing member 1162 on the valve support 1110 and a second sealing member 1164 on the anchoring member 1120. The first and second sealing members 1162, 1164 can be made from a flexible material, such as Dacron® or another type of polymeric material. The first sealing member 1162 can cover the interior and/or exterior surfaces of the valve support 1110. In the embodiment illustrated in FIG. 13A, the first sealing member 1162 is attached to the interior surface of the valve support 1110, and the prosthetic valve assembly 1150 is attached to the first sealing member 1162 and commissure portions of the valve support 1110. The second sealing member 1164 is attached to the inner surface of the anchoring member 1120. As a result, the outer annular engagement surface of the fixation structure 1130 is not covered by the second sealing member 1164 so that the outer annular engagement surface of the fixation structure 1130 directly contacts the tissue of the native annulus.

The device 1100 can further include an extension member 1170. The extension member 1170 can be an extension of the second sealing member 1164, or it can be a separate component attached to the second sealing member 1164 and/or the first portion 1132 of the fixation structure 1130. The extension member 1170 can be a flexible member that, in a deployed state (FIG. 13A), flexes relative to the first portion 1132 of the fixation structure 1130. In operation, the extension member 1170 guides the device 1100 during implantation such that the device 1100 is located at a desired elevation and centered relative to the native annulus. As described below, the extension member 1170 can include a support member, such as a metal wire or other structure, that can be visualized via fluoroscopy or other imaging techniques during implantation. For example, the support member can be a radiopaque wire.

Figure 14A:
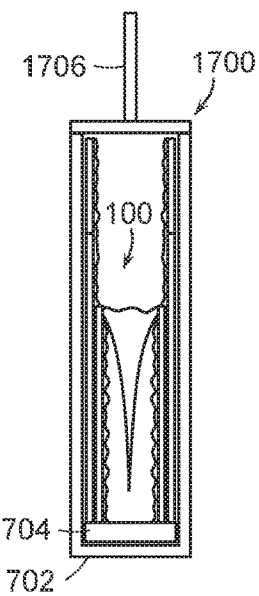
FIGS. 14A and 14B are cross-sectional side views schematically illustrating aspects of delivering a prosthetic heart valve device in accordance with an embodiment of the present technology.
Figure 14B:
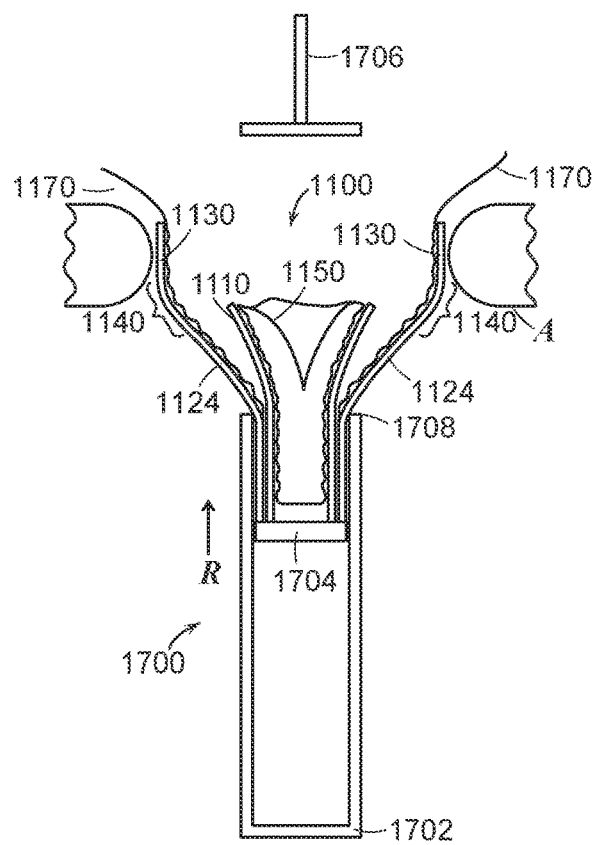

FIGS. 14A and 14B are cross-sectional views illustrating an example of the operation of the smooth bend 1140 between the arms 1124 and the fixation structure 1130 in the recapturing of the device 1100 after partial deployment. FIG. 14A schematically shows the device 1100 loaded into a capsule 1700 of a delivery system in a delivery state, and FIG. 14B schematically shows the device 1100 in a partially deployed state. Referring to FIG. 14A, the capsule 1700 has a housing 1702, a pedestal or support 1704, and a top 1706. In the delivery state shown in FIG. 14A, the device 1100 is in a low-profile configuration suitable for delivery through a catheter or cannula to a target implant site at a native heart valve.

Referring to FIG. 14B, the housing 1702 of the capsule 1700 has been moved distally such that the extension member 1170, fixation structure 1130 and a portion of the arms 1124 have been released from the housing 1702 in a partially deployed state. This is useful for locating the fixation structure 1130 at the proper elevation relative to the native valve annulus A such that the fixation structure 1130 expands radially outward into contact the inner surface of the native annulus A. However, the device 1100 may need to be repositioned and/or removed from the patient after being partially deployed. To do this, the housing 1702 is retracted (arrow R) back toward the fixation structure 1130. As the housing 1702 slides along the arms 1124, the smooth bend 1140 between the arms 1124 and the fixation structure 1130 allows the edge 1708 of the housing 1702 to slide over the smooth bend 1140 and thereby recapture the fixation structure 1130 and the extension member 1170 within the housing 1702. The device 1100 can then be removed from the patient or repositioned for redeployment at a better location relative to the native annulus A. Further aspects of prosthetic heart valve devices in accordance with the present technology and their interaction with corresponding delivery devices are described below with reference to FIGS. 15-26.

Figure 15:
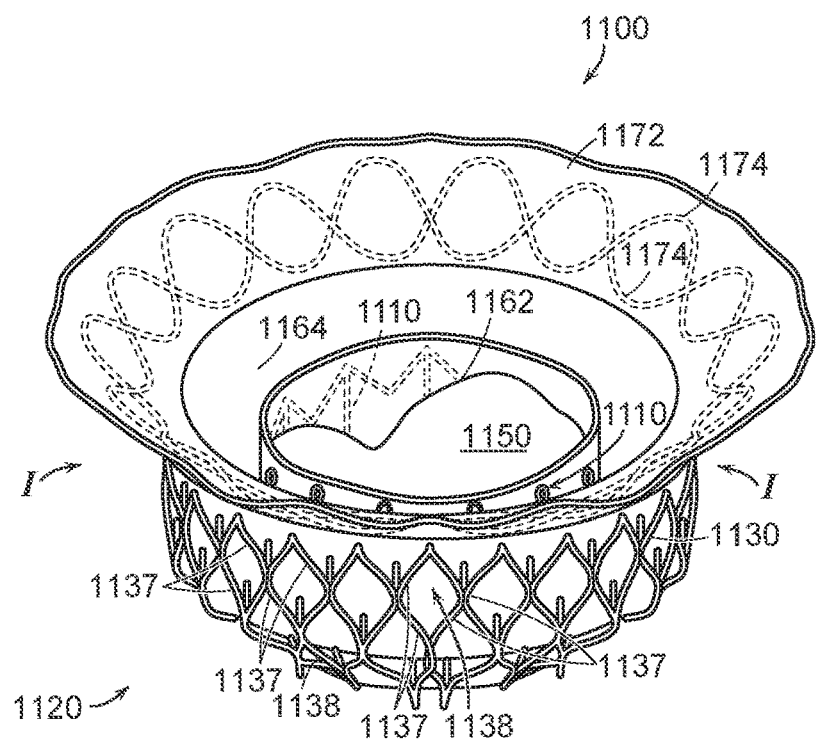
FIG. 15 is a top isometric view of a prosthetic heart valve device in accordance with an embodiment of the present technology.

FIG. 15 is a top isometric view of an example of the device 1100. In this embodiment, the valve support 1110 defines a first frame (e.g., an inner frame) and fixation structure 1130 of the anchoring member 1120 defines a second frame (e.g., an outer frame) that each include a plurality of structural elements. The fixation structure 1130, more specifically, includes structural elements 1137 arranged in diamond-shaped cells 1138 that together form at least a substantially cylindrical ring when freely and fully expanded as shown in FIG. 15. The structural elements 1137 can be struts or other structural features formed from metal, polymers, or other suitable materials that can self-expand or be expanded by a balloon or other type of mechanical expander.

In several embodiments, the fixation structure 1130 can be a generally cylindrical fixation ring having an outwardly facing engagement surface. For example, in the embodiment shown in FIG. 15, the outer surfaces of the structural elements 1137 define an annular engagement surface configured to press outwardly against the native annulus in the deployed state. In a fully expanded state without any restrictions, the walls of the fixation structure 1130 are at least substantially parallel to those of the valve support 1110. However, the fixation structure 1130 can flex inwardly (arrow I) in the deployed state when it presses radially outwardly against the inner surface of the native annulus of a heart valve.

The embodiment of the device 1100 shown in FIG. 15 includes the first sealing member 1162 lining the interior surface of the valve support 1110, and the second sealing member 1164 along the inner surface of the fixation structure 1130. The extension member 1170 has a flexible web 1172 (e.g., a fabric) and a support member 1174 (e.g., metal or polymeric strands) attached to the flexible web 1172. The flexible web 1172 can extend from the second sealing member 1164 without a metal-to-metal connection between the fixation structure 1130 and the support member 1174. For example, the extension member 1170 can be a continuation of the material of the second sealing member 1164. Several embodiments of the extension member 1170 are thus a malleable or floppy structure that can readily flex with respect to the fixation structure 1130. The support member 1174 can have a variety of configurations and be made from a variety of materials, such as a double-serpentine structure made from Nitinol.

Figure 16:
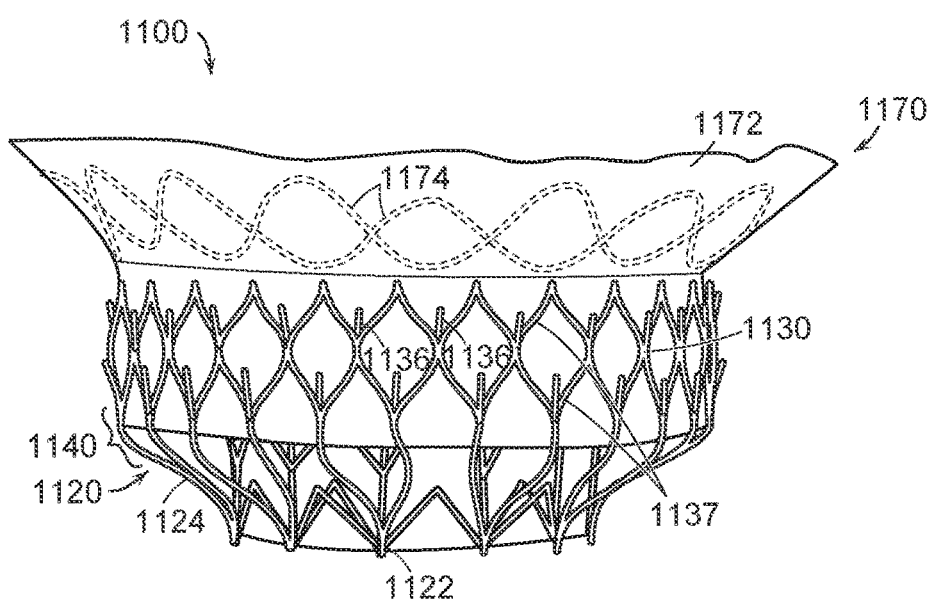
FIG. 16 is a side view and FIG. 17 is a bottom isometric view of the prosthetic heart valve device of FIG. 15.
Figure 17:
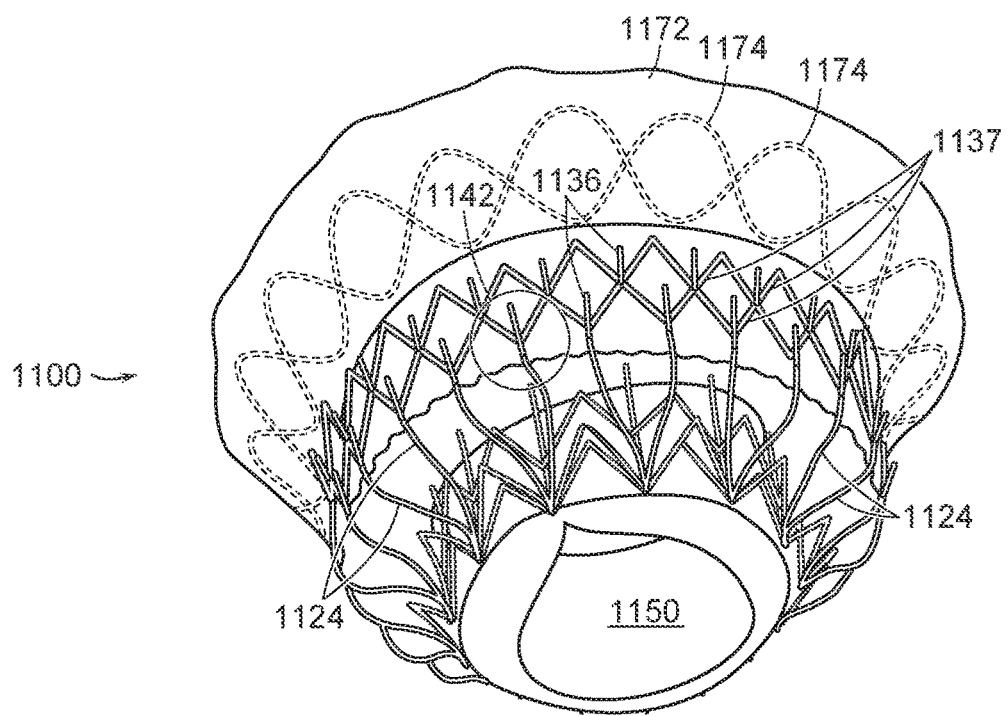

FIG. 16 is a side view and FIG. 17 is a bottom isometric view of the device 1100 shown in FIG. 15. Referring to FIG. 16, the arms 1124 extend radially outward from the base portion 1122 at an angle α selected to position the fixation structure 1130 radially outward from the valve support 1110 (FIG. 15) by a desired distance in a deployed state. The angle α is also selected to allow the edge 1708 of the delivery system housing 1702 (FIG. 14B) to slide from the base portion 1122 toward the fixation structure 1130 during recapture. In many embodiments, the angle α is 15°-75°, or more specifically 15°-60°, or still more specifically 30°-45°. The arms 1124 and the structural elements 1137 of the fixation structure 1130 can be formed from the same struts (i.e., formed integrally with each other) such that the smooth bend 1140 is a continuous, smooth transition from the arms 1124 to the structural elements 1137. This is expected to enable the edge 1708 of the housing 1702 to more readily slide over the smooth bend 1140 in a manner that allows the fixation structure 1130 to be recaptured in the housing 1702 of the capsule 1700 (FIG. 14B). Additionally, by integrally forming the arms 1124 and the structural elements 1137 with each other, it inhibits damage to the device 1100 at a junction between the arms 1124 and the structural elements 1137 compared to a configuration in which the arms 1124 and structural elements 1137 are separate components and welded or otherwise fastened to each other.

Referring to FIGS. 16 and 17, the arms 1124 are also separated from each other along their entire length from where they are connected to the base portion 1122 through the smooth bend 1140 (FIG. 16) to the structural elements 1137 of the fixation structure 1130. The individual arms 1124 are thus able to readily flex as the edge 1708 of the housing 1702 (FIG. 14B) slides along the arms 1124 during recapture. This is expected to reduce the likelihood that the edge 1708 of the housing 1702 will catch on the arms 1124 and prevent the device 1100 from being recaptured in the housing 1702.

In one embodiment, the arms 1124 have a first length from the base 1122 to the smooth bend 1140, and the structural elements 1137 of the fixation structure 1130 at each side of a cell 1138 (FIG. 15) have a second length that is less than the first length of the arms 1124. The fixation structure 1130 is accordingly less flexible than the arms 1124. As a result, the fixation structure 1130 is able to press outwardly against the native annulus with sufficient force to secure the device 1100 to the native annulus, while the arms 1124 are sufficiently flexible to fold inwardly when the device is recaptured in a delivery device.

In the embodiment illustrated in FIGS. 15-17, the arms 1124 and the structural elements 1137 are configured such that each arm 1124 and the two structural elements 1137 extending from each arm 1124 formed a Y-shaped portion 1142 (FIG. 17) of the anchoring member 1120. Additionally, the right-hand structural element 1137 of each Y-shaped portion 1142 is coupled directly to a left-hand structural element 1137 of an immediately adjacent Y-shaped portion 1142. The Y-shaped portions 1142 and the smooth bends 1140 are expected to further enhance the ability to slide the housing 1702 along the arms 1124 and the fixation structure 1130 during recapture.

Figure 18:
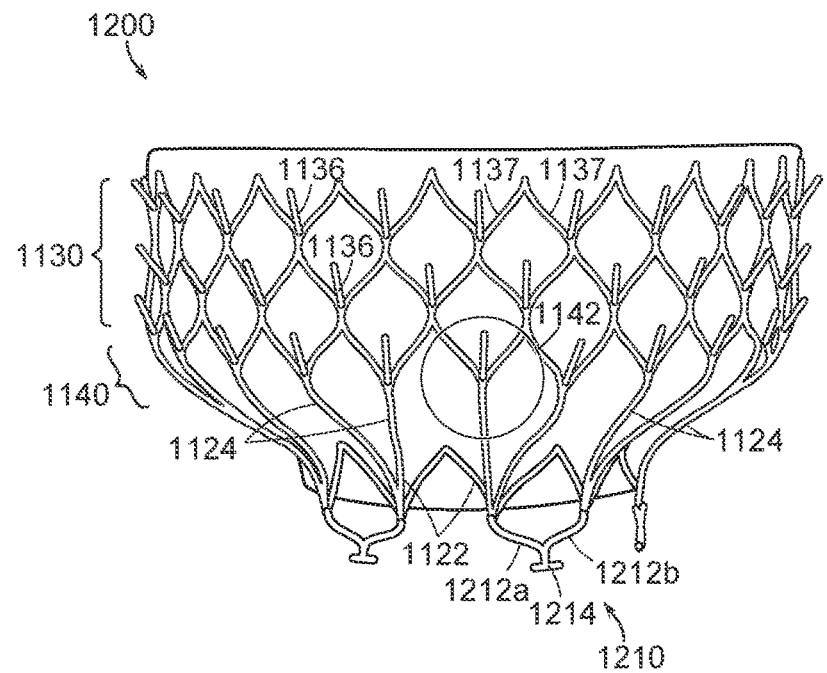
FIG. 18 is a side view and FIG. 19 is a bottom isometric view of a prosthetic heart valve device in accordance with an embodiment of the present technology.
Figure 19:
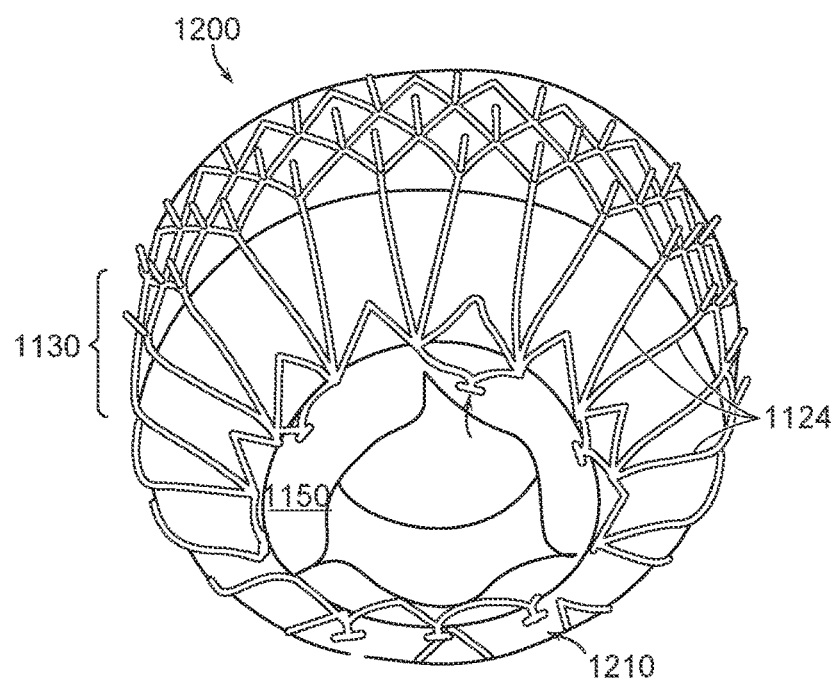

FIG. 18 is a side view and FIG. 19 is a bottom isometric view of a prosthetic heart valve device ("device") 1200 in accordance with another embodiment of the present technology. The device 1200 is shown without the extension member 1170 (FIGS. 15-17), but the device 1200 can further include the extension member 1170 described above. The device 1200 further includes extended connectors 1210 projecting from the base 1122 of the anchoring member 1120. Alternatively, the extended connectors 1210 can extend from the valve support 1110 (FIGS. 13A-17) in addition to or in lieu of extending from the base 1122 of the anchoring member 1120. The extended connectors 1210 can include a first strut 1212a attached to one portion of the base 1122 and a second strut 1212b attached to another portion of the base 1122. The first and second struts 1212a-b are configured to form a V-shaped structure in which they extend toward each other in a downstream direction and are connected to each other at the bottom of the V-shaped structure. The V-shaped structure of the first and second struts 1212a-b causes the extension connector 1210 to elongate when the device 1200 is in a low-profile configuration within the capsule 1700 (FIG. 14A) during delivery or partial deployment. When the device 1200 is fully released from the capsule 1700 (FIG. 14A) the extension connectors 1210 foreshorten to avoid interfering with blood flow along the left ventricular outflow tract.

The extended connectors 1210 further include an attachment element 1214 configured to releasably engage a delivery device. The attachment element 1214 can be a T-bar or other element that prevents the device 1200 from being released from the capsule 1700 (FIG. 14A) of a delivery device until desired. For example, a T-bar type attachment element 1214 can prevent the device 1200 from moving axially during deployment or partial deployment until the housing 1702 (FIG. 14A) moves beyond the portion of the delivery device engaged with the attachment elements 1214. This causes the attachment elements 1214 to disengage from the capsule 1700 (FIG. 14A) as the outflow region of the valve support 1110 and the base 1122 of the anchoring member 1120 fully expand to allow for full deployment of the device 1200.

Figure 20:
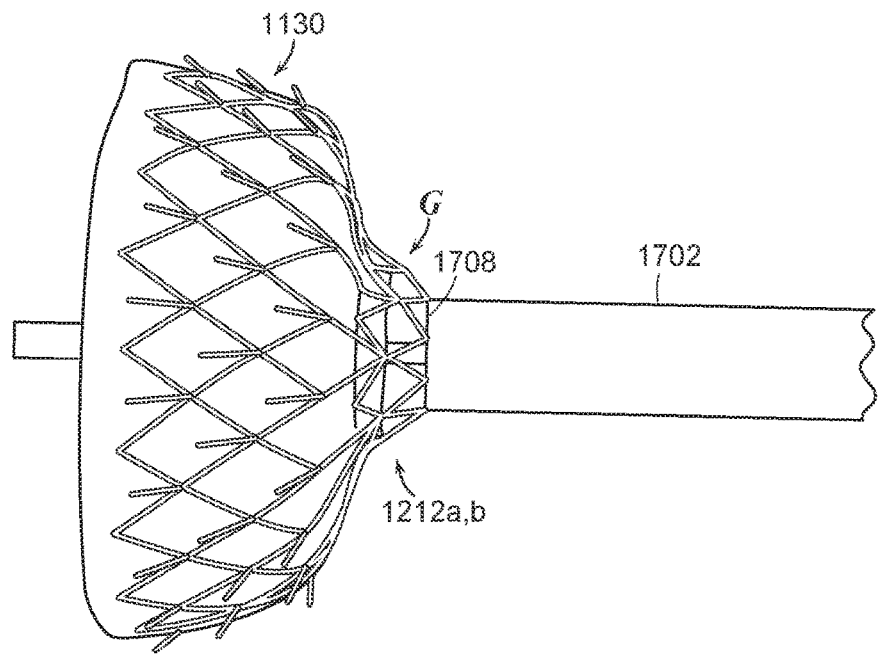
FIG. 20 is a side view and FIG. 21 is a bottom isometric view of the prosthetic heart valve device of FIGS. 18 and 19 at a partially deployed state with respect to a delivery device.
Figure 21:
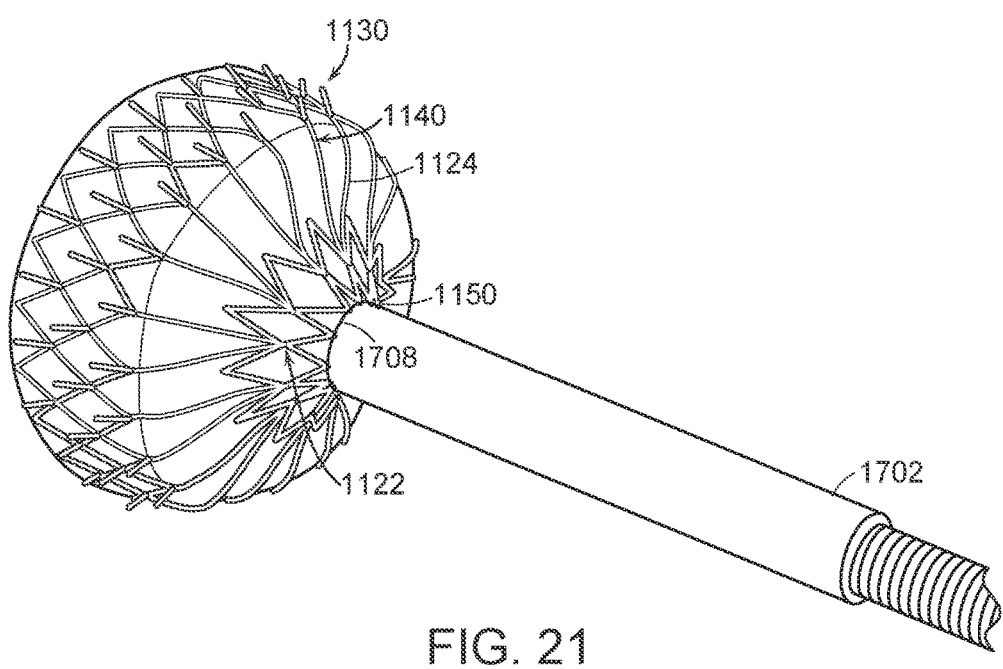

FIG. 20 is a side view and FIG. 21 is a bottom isometric view of the device 1200 in a partially deployed state in which the device 1200 is still capable of being recaptured in the housing 1702 of the delivery device 1700. Referring to FIG. 20, the device 1200 is partially deployed with the fixation structure 1130 substantially expanded but the attachment elements 1214 (FIG. 18) still retained within the capsule 1700. This is useful for determining the accuracy of the position of the device 1200 during implantation while retaining the ability to recapture the device 1200 in case it needs to be repositioned or removed from the patient. In this state of partial deployment, the elongated first and second struts 1212a-b of the extended connectors 1210 space the base 1122 of the anchoring member 1120 and the outflow region of the valve support 1110 (FIG. 13A) apart from the edge 1708 of the capsule 1700 by a gap G.

Referring to FIG. 21, the gap G enables blood to flow through the prosthetic valve assembly 1150 while the device 1200 is only partially deployed. As a result, the device 1200 can be partially deployed to determine (a) whether the device 1200 is positioned correctly with respect to the native heart valve anatomy and (b) whether proper blood flow passes through the prosthetic valve assembly 1150 while the device 1200 is still retained by the delivery system 1700. As such, the device 1200 can be recaptured if it is not in the desired location and/or if the prosthetic valve is not functioning properly. This additional functionality is expected to significantly enhance the ability to properly position the device 1200 and assess, in vivo, whether the device 1200 will operate as intended, while retaining the ability to reposition the device 1200 for redeployment or remove the device 1200 from the patient.

Figure 22:
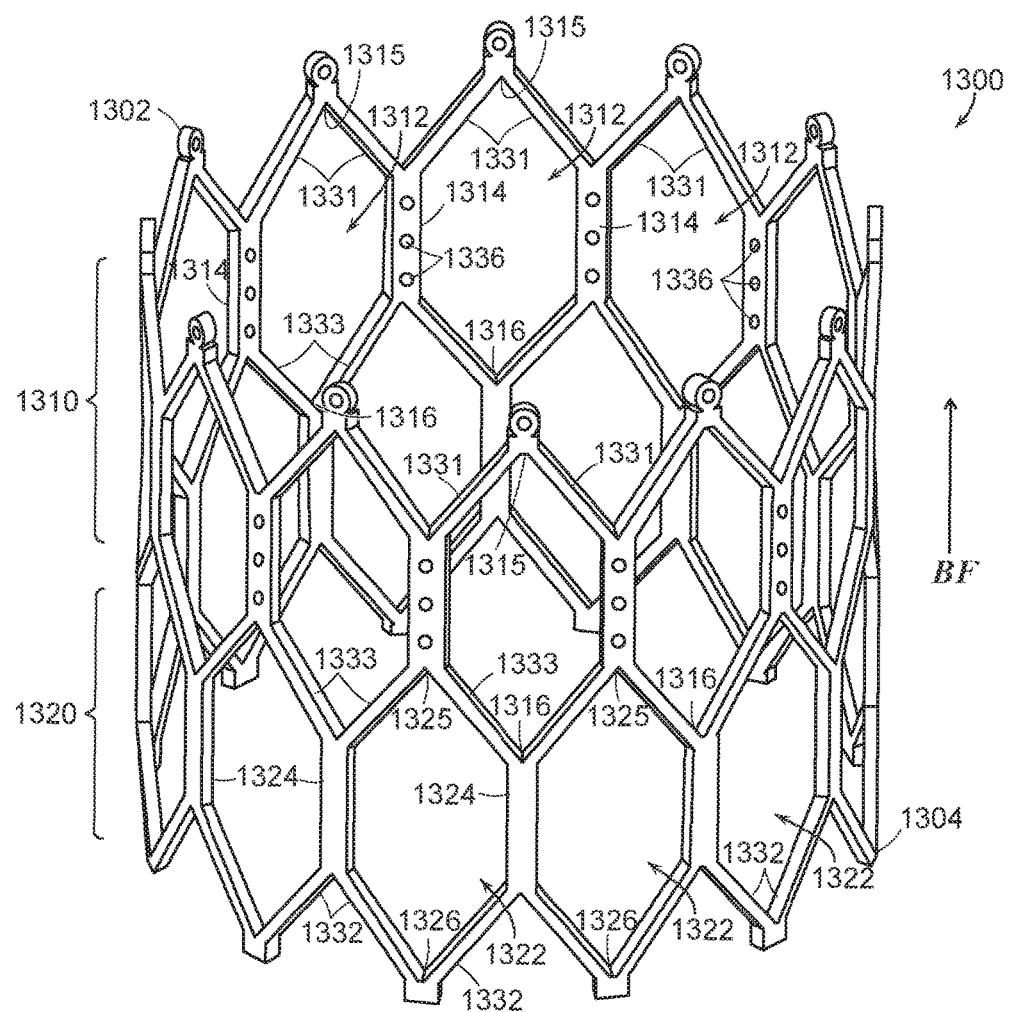
FIG. 22 is an isometric view of a valve support for use with prosthetic heart valve devices in accordance with the present technology.

FIG. 22 is an isometric view of a valve support 1300 in accordance with an embodiment of the present technology. The valve support 1300 can be an embodiment of the valve support 1110 described above with respect to FIGS. 13A-21. The valve support 1300 has an outflow region 1302, an inflow region 1304, a first row 1310 of first hexagonal cells 1312 at the outflow region 1302, and a second row 1320 of second hexagonal cells 1322 at the inflow region 1304. For purposes of illustration, the valve support shown in FIG. 22 is inverted compared to the valve support 1110 shown in FIGS. 13A-21 such that the blood flows through the valve support 1300 in the direction of arrow BF. In mitral valve applications, the valve support 1300 would be positioned within the anchoring member 1120 (FIG. 13A) such that the inflow region 1304 would correspond to orientation of the inflow region 1112 in FIG. 13A and the outflow region 1302 would correspond to the orientation of the outflow region 1114 in FIG. 13A.

Each of the first hexagonal cells 1312 includes a pair of first longitudinal supports 1314, a downstream apex 1315, and an upstream apex 1316. Each of the second hexagonal cells 1322 can include a pair of second longitudinal supports 1324, a downstream apex 1325, and an upstream apex 1326. The first and second rows 1310 and 1312 of the first and second hexagonal cells 1312 and 1322 are directly adjacent to each other. In the illustrated embodiment, the first longitudinal supports 1314 extend directly from the downstream apexes 1325 of the second hexagonal cells 1322, and the second longitudinal supports 1324 extend directly from the upstream apexes 1316 of the first hexagonal cells 1312. As a result, the first hexagonal cells 1312 are offset from the second hexagonal cells 1322 around the circumference of the valve support 1300 by half of the cell width.

In the embodiment illustrated in FIG. 22, the valve support 1300 includes a plurality of first struts 1331 at the outflow region 1302, a plurality of second struts 1332 at the inflow region 1304, and a plurality of third struts 1333 between the first and second struts 1331 and 1332. Each of the first struts 1331 extends from a downstream end of the first longitudinal supports 1314, and pairs of the first struts 1331 are connected together to form first downstream V-struts defining the downstream apexes 1315 of the first hexagonal cells 1312. In a related sense, each of the second struts 1332 extends from an upstream end of the second longitudinal supports 1324, and pairs of the second struts 1332 are connected together to form second upstream V-struts defining the upstream apexes 1326 of the second hexagonal cells 1322. Each of the third struts 1333 has a downstream end connected to an upstream end of the first longitudinal supports 1314, and each of the third struts 1333 has an upstream end connected to a downstream end of one of the second longitudinal supports 1324. The downstream ends of the third struts 1333 accordingly define a second downstream V-strut arrangement that forms the downstream apexes 1325 of the second hexagonal cells 1322, and the upstream ends of the third struts 1333 define a first upstream V-strut arrangement that forms the upstream apexes 1316 of the first hexagonal cells 1312. The third struts 1333, therefore, define both the first upstream V-struts of the first hexagonal cells 1312 and the second downstream V-struts of the second hexagonal cells 1322.

The first longitudinal supports 1314 can include a plurality of holes 1336 through which sutures can pass to attach a prosthetic valve assembly and/or a sealing member. In the embodiment illustrated in FIG. 22, only the first longitudinal supports 1314 have holes 1336. However, in other embodiments the second longitudinal supports 1324 can also include holes either in addition to or in lieu of the holes 1336 in the first longitudinal supports 1314.

Figure 23:
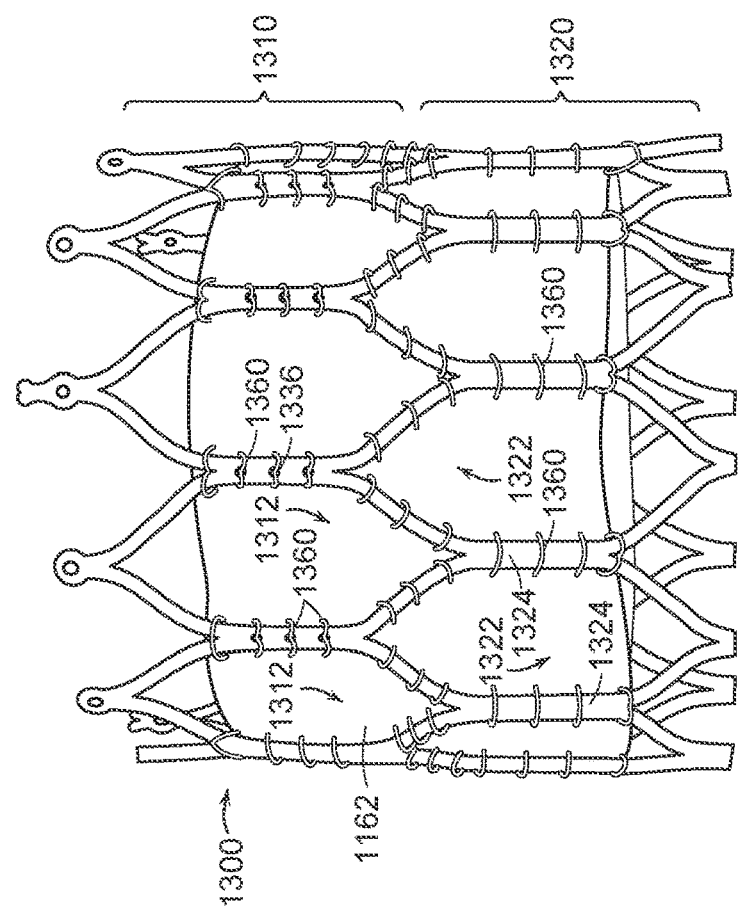
FIGS. 23 and 24 are side and bottom isometric views, respectively, of a prosthetic heart valve attached to the valve support of FIG. 22.
Figure 24:
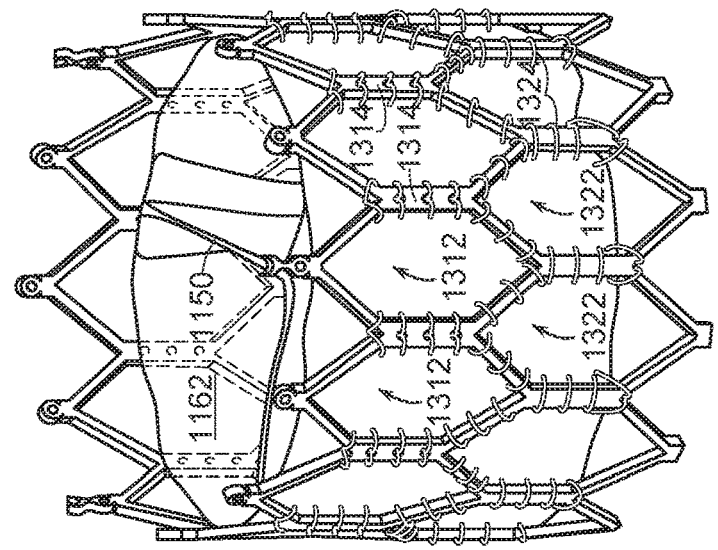

FIG. 23 is a side view and FIG. 24 is a bottom isometric view of the valve support 1300 with a first sealing member 1162 attached to the valve support 1300 and a prosthetic valve 1150 within the valve support 1300. The first sealing member 1162 can be attached to the valve support 1300 by a plurality of sutures 1360 coupled to the first longitudinal supports 1314 and the second longitudinal supports 1324. At least some of the sutures 1360 coupled to the first longitudinal supports 1314 pass through the holes 1336 to further secure the first sealing member 1162 to the valve support 1300.

Referring to FIG. 24, the prosthetic valve 1150 can be attached to the first sealing member 1162 and/or the first longitudinal supports 1314 of the valve support 1300. For example, the commissure portions of the prosthetic valve 1150 can be aligned with the first longitudinal supports 1314, and the sutures 1360 can pass through both the commissure portions of the prosthetic valve 1150 and the first sealing member 1162 where the commissure portions of the prosthetic valve 1150 are aligned with a first longitudinal support 1314. The inflow portion of the prosthetic valve 1150 can be sewn to the first sealing member 1162.

The valve support 1300 illustrated in FIGS. 22-24 is expected to be well suited for use with the device 1200 described above with reference to FIGS. 18-21. More specifically, the first struts 1331 cooperate with the extended connectors 1210 (FIGS. 18-21) of the device 1200 to separate the outflow portion of the prosthetic valve 1150 from the capsule 1700 (FIGS. 12A and 12B) when the device 1200 is in a partially deployed state. The first struts 1331, for example, elongate when the valve support 1300 is not fully expanded (e.g., at least partially contained within the capsule 1700) and foreshorten when the valve support is fully expanded. This allows the outflow portion of the prosthetic valve 1150 to be spaced further apart from the capsule 1700 in a partially deployed state so that the prosthetic valve 1150 can at least partially function when the device 1200 (FIGS. 18-21) is in the partially deployed state. Therefore, the valve support 1300 is expected to enhance the ability to assess whether the prosthetic valve 1150 is fully operational in a partially deployed state.

Figure 25:
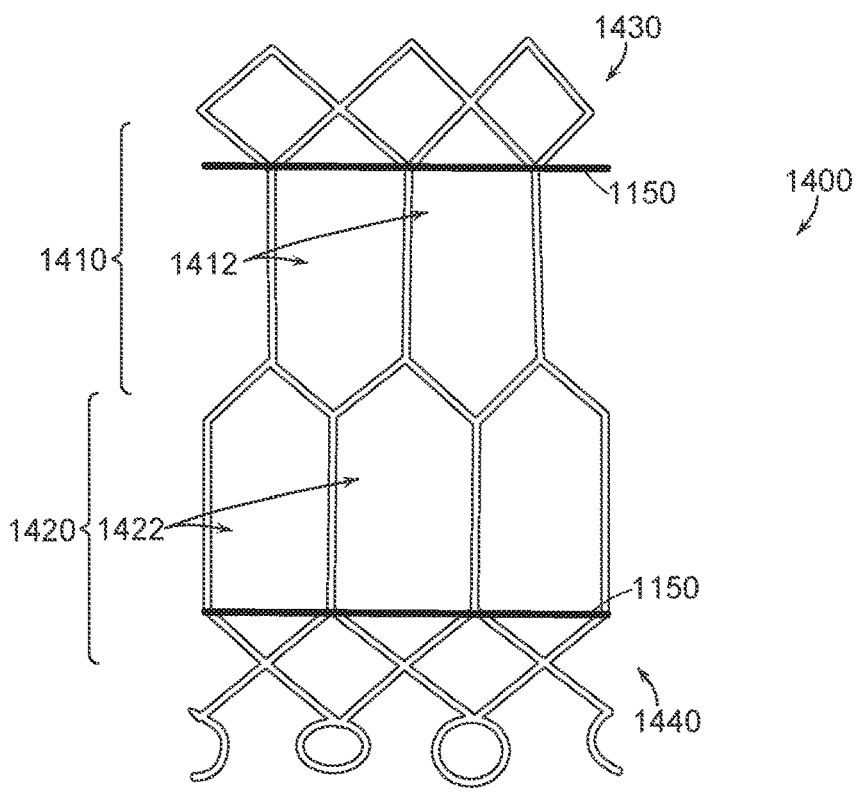
FIGS. 25 and 26 are side views schematically showing valve supports in accordance with additional embodiments of the present technology.
Figure 26:
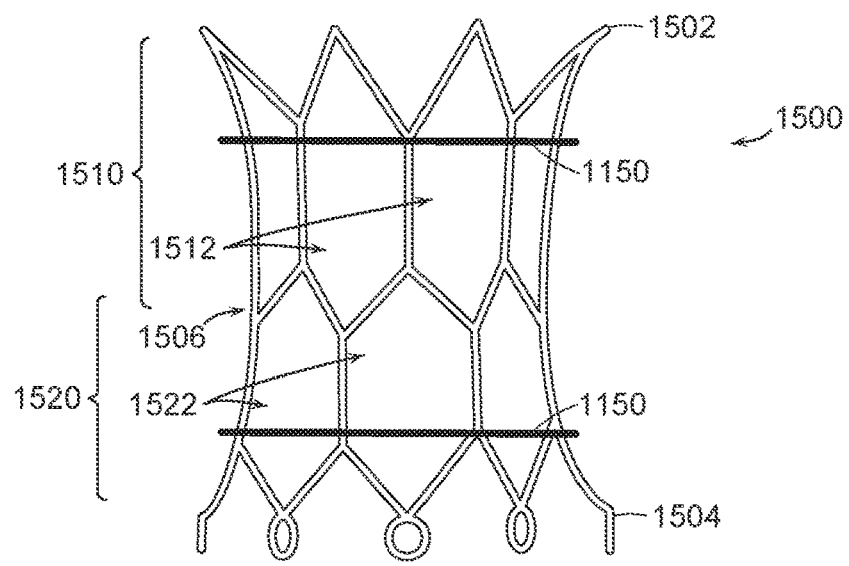

FIGS. 25 and 26 are schematic side views of valve supports 1400 and 1500, respectively, in accordance with other embodiments of the present technology. Referring to FIG. 25, the valve support 1400 includes a first row 1410 of first of hexagonal cells 1412 and a second row 1420 of second hexagonal cells 1422. The valve 1400 can further include a first row 1430 of diamond-shaped cells extending from the first hexagonal cells 1412 and a second row 1440 of diamond-shaped cells extending from the second hexagonal cells 1422. The additional diamond-shaped cells elongate in the low-profile state, and thus they can further space the prosthetic valve 1150 (shown schematically) apart from a capsule of a delivery device. Referring to FIG. 26, the valve support 1500 includes a first row 1510 of first hexagonal cells 1512 at an outflow region 1502 and a second row 1520 of second hexagonal cells 1522 at an inflow region 1504. The valve support 1500 is shaped such that an intermediate region 1506 (between the inflow and outflow regions 1502 and 1504) has a smaller cross-sectional area than that of the outflow region 1502 and/or the inflow region 1504. As such, the first row 1510 of first hexagonal cells 1512 flares outwardly in the downstream direction and the second row 1520 of second hexagonal cells 1522 flares outwardly in the upstream direction.

EXAMPLES

Several aspects of the present technology are set forth in the following examples.

1. A system for delivering a prosthetic heart valve device into a heart of a patient, the system comprising:
  an elongated catheter body; and
  a delivery capsule carried by the elongated catheter body and configured to move between a delivery state for holding the prosthetic heart valve device and a deployment state for at least partially deploying the prosthetic heart valve device, wherein the delivery capsule comprises—
    a first housing configured to contain at least a first portion of the prosthetic heart valve device;
    a second housing slidably associated with at least a portion of the first housing, wherein the second housing is configured to contain a second portion of the prosthetic heart valve device,
    wherein, during a first deployment stage, the first housing moves in a distal direction with respect to the second housing to release the first portion of the prosthetic heart valve device from the delivery capsule, and
    wherein, during a second deployment stage, the second housing and the first housing together move in a distal direction to release the second portion of the prosthetic heart valve device from the delivery capsule.

2. The system of example 1 wherein the delivery capsule further comprises:
  a first sealing member between a distal portion of the first housing and the second housing, wherein the first sealing member is slidable along the second housing;
  a second sealing member between a proximal portion of the second housing and the first housing;
  a first fluid chamber between the first and second sealing members; and
  a second fluid chamber defined at least in part by an inner surface of the second housing,
  wherein, during the first deployment stage, fluid is delivered to the first chamber to slide the first sealing member in the distal direction over the second housing, and
  wherein, during the second deployment stage, fluid is delivered to the second chamber such that the first and second housings move together in the distal direction.

3. The system of example 2, further comprising a platform extending from the elongated catheter body into the second housing, wherein the platform includes a distal end portion slidably sealed against an inner wall of the second housing and defines a proximal end of the second fluid chamber.

4. The system of example 2 or 3 wherein the first sealing member is a first sleeve extending inwardly from the first housing, and the second sealing member is a second sleeve extending outwardly from the second housing.

5. The system of any one of examples 2-4 wherein, after the second deployment stage, the first fluid chamber is configured to be evacuated of fluid while the second fluid chamber remains pressurized with fluid such that the first housing moves in a proximal direction.

6. The system of any one of examples 2-5, further comprising:
  a first fluid lumen extending through the elongated catheter body and in fluid communication with the first fluid chamber; and
  a second fluid lumen extending through the elongated catheter body in fluid communication with the second fluid chamber.

7. The system of example 6 wherein the first fluid lumen passes through the second housing and into a port in the first housing, wherein the port is in fluid communication with the first fluid chamber.

8. The system of example 6 wherein second housing has an inner channel in a wall of the second housing, and wherein the inner channel is in fluid communication with the first fluid chamber and defines a portion of the first fluid lumen.

9. The system of any one of examples 1-8 wherein the delivery capsule has an overall length of at most 50 mm.

10. The system of any one of examples 1-9 wherein the delivery capsule has an overall length of at most 40 mm.

11. The system of any one of examples 1-10 wherein the first housing and the second housing each have a length of at most 30 mm.

12. The system of any one of examples 1-11, further comprising:
  a first spring biasing the first housing toward the delivery state; and
  a second spring biasing the second housing toward the delivery state.

13. The system of example 1 wherein the second housing includes an arched feature on an outer surface of the second housing and positioned between the first and second housings, wherein the system further comprises:
  a first tether element attached to a first portion of the first housing, wherein the first tether element extends from the first housing, over a distal end portion of the second housing, into the second housing, and through the elongated catheter body;
  a second tether element attached to a second portion of the first housing, wherein the second tether element extends in a proximal direction around the arched feature, over the distal end portion of the second housing, into the second housing, and through though the elongated catheter body,
  wherein proximal retraction of the first tether element slides the first housing over the second housing in the distal direction to unsheathe at least a portion of the prosthetic heart valve device from the delivery capsule, and
  wherein proximal retraction of the second tether element slides the first housing over the second housing in a proximal direction to resheathe the prosthetic heart valve device.

14. A system for delivering a prosthetic heart valve device into a heart of a patient, the system comprising:
  an elongated catheter body; and
  a delivery capsule carried by the elongated catheter body and configured to be hydraulically driven between a delivery state for holding the prosthetic heart valve device and a deployment state for at least partially deploying the prosthetic heart valve device, wherein the delivery capsule comprises—
    a first housing configured to contain at least a first portion of the prosthetic heart valve device;
    a second housing slidably disposed within at least a portion of the first housing, wherein the second housing is configured to contain a second portion of the prosthetic heart valve device;
    a first fluid chamber defined at least in part by an inner surface of the first housing and an outer surface of the second housing; and a second fluid chamber defined at least in part by an inner surface of the second housing,
    wherein, during a first deployment stage, the first fluid chamber is configured to receive fluid that moves the first housing in a distal direction over the second housing to release the first portion of the prosthetic heart valve device from the delivery capsule, and
    wherein, during a second deployment stage, the second chamber is configured to receive fluid such that the first and second housings move together in the distal direction to release the second portion of the prosthetic heart valve device from the delivery capsule.

15. The system of example 14 wherein the delivery capsule further comprises:
  a first sealing member between a distal portion of the first housing and the second housing, wherein the first sealing member is slidable along the second housing; and
  a second sealing member between a proximal portion of the first housing and the second housing,
  wherein the first fluid chamber extends between the first and second sealing members.

16. The system of example 14 or 15, further comprising a platform extending from the elongated catheter body into the second housing, wherein the platform includes a distal end portion slidably sealed against an inner wall of the second housing, and wherein the distal end portion of the platform defines a proximal end of the second fluid chamber.

17. The system of any one of examples 14-16 wherein, during a resheathing phase, the first fluid chamber is configured to be evacuated of fluid while the second fluid chamber remains pressurized with fluid to allow the first housing to slide in a proximal direction over the second housing.

18. The system of any one of examples 14-17, further comprising:
  a first fluid lumen extending through the elongated catheter body and in fluid communication with the first fluid chamber; and
  a second fluid lumen extending through the elongated catheter body in fluid communication with the second fluid chamber.

19. The system of example 18 wherein the first fluid lumen passes into the second housing, outside the first and second housings, and into a port in the first housing, wherein the port is in fluid communication with the first fluid chamber.

20. The system of example 18 wherein the first lumen is defined in part by an inner channel of the second housing.

21. The system of any one of examples 14-20 wherein the first and second housings each have a length of 20-30 mm.

22. The system of any one of examples 14-21, further comprising:
  a first spring configured to urge the first housing toward the delivery state when the first fluid chamber is evacuated of fluid; and
  a second spring configured to urge the second housing toward the delivery state when the second fluid chamber is evacuated of fluid.

23. A method for delivering a prosthetic heart valve device to a native mitral valve of a heart of a human patient, the method comprising:
  positioning a delivery capsule at a distal portion of an elongated catheter body within the heart, the delivery capsule carrying the prosthetic heart valve device;
  delivering fluid to a first fluid chamber of the delivery capsule to slide a first housing in a distal direction over a portion of a second housing, thereby releasing a first portion of the prosthetic heart valve device from the delivery capsule; and
  delivering fluid to a second fluid chamber of the delivery capsule to move the second housing together with the first housing in the distal direction to release a second portion of the prosthetic heart valve device from the delivery capsule.

24. The method of example 23, further comprising evacuating fluid from the first fluid chamber while the second fluid chamber remains pressurized with fluid such that the first housing slides in a proximal direction over the second housing.

25. The method of example 23 or 24 wherein positioning the delivery capsule within the heart comprises delivering the delivery capsule across an atrial septum of the heart to a left atrium.

26. A method for delivering a prosthetic heart valve device to a native mitral valve of a heart of a human patient, the method comprising:
- delivering a delivery capsule at a distal portion of an elongated catheter body across an atrial septum of the heart to a left atrium of the heart, the delivery capsule having a first housing and a second housing slidably disposed within at least a portion of the first housing, wherein the first and second housing contain the prosthetic heart valve device in a delivery state;
- positioning the delivery capsule between native leaflets of the native mitral valve;
- moving the first housing in a distal direction over the second housing to release a first portion of the prosthetic heart valve device from the delivery capsule; and
- moving a second housing in the distal direction to release a second portion of the prosthetic heart valve device from the delivery capsule.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but that well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for delivering a prosthetic heart valve device into a heart of a patient, the system comprising:
- an elongated catheter body; and
- a delivery capsule carried by the elongated catheter body and configured to move between a delivery state for holding the prosthetic heart valve device and a deployment state for at least partially deploying the prosthetic heart valve device, wherein the delivery capsule comprises:
- a first housing configured to contain at least a first portion of the prosthetic heart valve device; and
- a second housing slidably associated with a portion of the first housing, wherein the second housing is configured to contain a second portion of the prosthetic heart valve device,
- wherein, during a first deployment stage, the first housing moves in a distal direction with respect to the second housing to release the first portion of the prosthetic heart valve device from the delivery capsule, and
- wherein, during a second deployment stage, the second housing and the first housing together move in a distal direction to release the second portion of the prosthetic heart valve device from the delivery capsule.

2. The system of claim 1 wherein the delivery capsule further comprises:
- a first sealing member between a distal portion of the first housing and the second housing, wherein the first sealing member is slidable along the second housing;
- a second sealing member between a proximal portion of the second housing and the first housing;
- a first fluid chamber between the first and second sealing members; and
- a second fluid chamber defined at least in part by an inner surface of the second housing,
- wherein, during the first deployment stage, fluid is delivered to the first chamber to slide the first sealing member in the distal direction over the second housing, and
- wherein, during the second deployment stage, fluid is delivered to the second chamber such that the first and second housings move together in the distal direction.

3. The system of claim 2, further comprising a platform extending from the elongated catheter body into the second housing, wherein the platform includes a distal end portion slidably sealed against an inner wall of the second housing and defines a proximal end of the second fluid chamber.

4. The system of claim 2 wherein the first sealing member is a first sleeve extending inwardly from the first housing, and the second sealing member is a second sleeve extending outwardly from the second housing.

5. The system of claim 2 wherein, after the second deployment stage, the first fluid chamber is configured to be evacuated of fluid while the second fluid chamber remains pressurized with fluid such that the first housing moves in a proximal direction.

6. The system of claim 2, further comprising:
- a first fluid lumen extending through the elongated catheter body and in fluid communication with the first fluid chamber; and
- a second fluid lumen extending through the elongated catheter body in fluid communication with the second fluid chamber.

7. The system of claim 6 wherein the first fluid lumen passes through the second housing and into a port in the first housing, wherein the port is in fluid communication with the first fluid chamber.

8. The system of claim 6 wherein second housing has an inner channel in a wall of the second housing, and wherein the inner channel is in fluid communication with the first fluid chamber and defines a portion of the first fluid lumen.

9. The system of claim 1 wherein the delivery capsule has an overall length of at most 50 mm.

10. The system of claim 1 wherein the delivery capsule has an overall length of at most 40 mm.

11. The system of claim 1 wherein the first housing and the second housing each have a length of at most 30 mm.

12. The system of claim 1, further comprising:
a first spring biasing the first housing toward the delivery state; and
a second spring biasing the second housing toward the delivery state.

13. The system of claim 1 wherein the second housing includes an arched feature on an outer surface of the second housing and positioned between the first and second housings, wherein the system further comprises:
a first tether element attached to a first portion of the first housing, wherein the first tether element extends from the first housing, over a distal end portion of the second housing, into the second housing, and through the elongated catheter body;
a second tether element attached to a second portion of the first housing, wherein the second tether element extends in a proximal direction around the arched feature, over the distal end portion of the second housing, into the second housing, and through though the elongated catheter body,
wherein proximal retraction of the first tether element slides the first housing over the second housing in the distal direction to unsheathe at least a portion of the prosthetic heart valve device from the delivery capsule, and
wherein proximal retraction of the second tether element slides the first housing over the second housing in a proximal direction to resheathe the prosthetic heart valve device.

14. A system for delivering a prosthetic heart valve device into a heart of a patient, the system comprising:
an elongated catheter body; and
a delivery capsule carried by the elongated catheter body and configured to be hydraulically driven between a delivery state for holding the prosthetic heart valve device and a deployment state for at least partially deploying the prosthetic heart valve device, wherein the delivery capsule comprises:
a first housing configured to contain at least a first portion of the prosthetic heart valve device;
a second housing slidably disposed within at least a portion of the first housing, wherein the second housing is configured to contain a second portion of the prosthetic heart valve device;
a first fluid chamber defined at least in part by an inner surface of the first housing and an outer surface of the second housing; and
a second fluid chamber defined at least in part by an inner surface of the second housing,
wherein, during a first deployment stage, the first fluid chamber is configured to receive fluid that moves the first housing in a distal direction over the second housing to release the first portion of the prosthetic heart valve device from the delivery capsule, and
wherein, during a second deployment stage, the second chamber is configured to receive fluid such that the first and second housings move together in the distal direction to release the second portion of the prosthetic heart valve device from the delivery capsule.

15. The system of claim 14 wherein the delivery capsule further comprises:
a first sealing member between a distal portion of the first housing and the second housing, wherein the first sealing member is slidable along the second housing; and
a second sealing member between a proximal portion of the first housing and the second housing,
wherein the first fluid chamber extends between the first and second sealing members.

16. The system of claim 14, further comprising a platform extending from the elongated catheter body into the second housing, wherein the platform includes a distal end portion slidably sealed against an inner wall of the second housing, and wherein the distal end portion of the platform defines a proximal end of the second fluid chamber.

17. The system of claim 14 wherein, during a resheathing phase, the first fluid chamber is configured to be evacuated of fluid while the second fluid chamber remains pressurized with fluid to allow the first housing to slide in a proximal direction over the second housing.

18. The system of claim 14, further comprising:
a first fluid lumen extending through the elongated catheter body and in fluid communication with the first fluid chamber; and
a second fluid lumen extending through the elongated catheter body in fluid communication with the second fluid chamber.

19. The system of claim 18 wherein the first fluid lumen passes into the second housing, outside the first and second housings, and into a port in the first housing, wherein the port is in fluid communication with the first fluid chamber.

20. The system of claim 18 wherein the first lumen is defined in part by an inner channel of the second housing.

21. The system of claim 14 wherein the first and second housings each have a length of 20-30 mm.

22. The system of claim 14, further comprising:
a first spring configured to urge the first housing toward the delivery state when the first fluid chamber is evacuated of fluid; and
a second spring configured to urge the second housing toward the delivery state when the second fluid chamber is evacuated of fluid.

* * * * *